US008663971B2

(12) United States Patent
Contreras et al.

(10) Patent No.: US 8,663,971 B2
(45) Date of Patent: *Mar. 4, 2014

(54) PROTEIN GLYCOSYLATION MODIFICATION IN METHYLOTROPHIC YEAST

(75) Inventors: Roland Contreras, Merelbeke (BE); Nico L. M. Callewaert, Lichtervelde (BE); Steven C. J. Geysens, Kruishoutem (BE)

(73) Assignees: VIB, VZW, Zwijnaarde (BE); Research Corporation Technologies, Inc., Tucscon, AZ (US); Universiteit Gent, Ghent (BE)

( * ) Notice: Subject to any disclaimer, the term of this patent is extended or adjusted under 35 U.S.C. 154(b) by 348 days.

This patent is subject to a terminal disclaimer.

(21) Appl. No.: 12/424,924

(22) Filed: Apr. 16, 2009

(65) Prior Publication Data
US 2010/0267084 A1 Oct. 21, 2010

Related U.S. Application Data

(63) Continuation of application No. 10/672,484, filed on Sep. 25, 2003, now Pat. No. 8,354,268, which is a continuation of application No. 09/896,594, filed on Jun. 29, 2001, now Pat. No. 6,803,225.

(60) Provisional application No. 60/215,676, filed on Jun. 30, 2000.

(51) Int. Cl.
*C12N 1/14* (2006.01)
*C12N 15/74* (2006.01)
*C12P 21/04* (2006.01)
*C12N 15/00* (2006.01)

(52) U.S. Cl.
USPC ............... 435/254.23; 435/471; 435/69.9

(58) Field of Classification Search
USPC .................... 435/254.23, 471, 69.9
See application file for complete search history.

(56) References Cited

U.S. PATENT DOCUMENTS

| | | | |
|---|---|---|---|
| 5,135,854 A | 8/1992 | MacKay et al. | |
| 5,705,616 A | 1/1998 | Lehle et al. | |
| 6,803,225 B2 * | 10/2004 | Contreras et al. | 435/254.2 |
| 7,252,933 B2 * | 8/2007 | Contreras et al. | 435/6.18 |
| 7,507,573 B2 * | 3/2009 | Contreras et al. | 435/254.11 |
| 8,058,053 B2 * | 11/2011 | Contreras et al. | 435/254.11 |
| 2002/0137134 A1 | 9/2002 | Gerngross | |

FOREIGN PATENT DOCUMENTS

| | | |
|---|---|---|
| EP | 0 314 096 A2 | 5/1989 |
| EP | 1 211 310 A1 | 6/2002 |
| EP | 1 297 172 B1 | 4/2003 |
| JP | 8-336387 | 12/1996 |
| JP | 9-261 | 1/1997 |
| WO | WO 91/05057 | 4/1991 |
| WO | WO 96/21038 | 7/1996 |
| WO | WO 02/00879 A2 | 1/2002 |
| WO | WO 2004/003205 A1 | 1/2004 |

OTHER PUBLICATIONS

Cereghino J.L. et al., "Heterologous Protein Expression in the Methylotrophic Yeast *Pichia pastoris*", *FEMS Microbiology Reviews* 24:45-66 (2000).
Herscovics A., "Processing Glycosidases of *Saccharomyces cerevisiae*", *Biochimica et Biophysica Acta* 1426:275-285 (1999).
Kang H.A. et al., "Glycosylation of Human $\alpha_1$-Antitrypsin in *Saccharomyces cerevisiae* and Methylotrophic Yeasts", *Yeast* 14:371-381 (1998).
Tremblay L.O. et al., "Molecular Cloning, Chromosomal Mapping and Tissue-Specific Expression of a Novel Human $\alpha$1,2-Mannosidase Gene Involved in N-Glyean Maturation", *Glycobiology* 8:585-595 (1998).
Malissard M. et al., "The Yeast Expression System for Recombinant Glycosyltransferases", *Glycoconjugate Journal* 16:125-139 (1999).
Nagasu T. et al., "Isolation of New Temperature-Sensitive Mutants of *Saccharomyces cerevisiae* Deficient in Mannose Outer Chain Elongation", *Yeast* 8:535-547 (1992).
Vervecken W. et al., "In Vivo Synthesis of Mammalian-Like, Hybrid-Type N-Glycans in *Pichia pastoris*", *Applied and Environmental Microbiology* 70(5):2639-2646 (2004).
Trimble R.B. et al., "Structure of Oligosaccharides on *Saccharomyces SUC2* Invertase Secreted by the Methylotrophic Yeast *Pichia pastoris*", *The Journal of Biological Chemistry* 266(34):22807-22817 (1991).
Verostek M.F. et al., "Mannosyltransferase Activities in Membranes from Various Yeast Strains", *Glycobiology* 5(7):671-681 (1995).
Pelham H.R.B. et al., "Sorting of Soluble ER Proteins in Yeast", *The EMBO Journal* 7(6):1757-1762 (1988).
Blandin G. et al., "Genomic Exploration of the Hemiascomycetous Yeasts: 13. *Pichia angusta*", *FEBS Letter* 487:76-81 (2000).
Kim M.W. et al., "Functional Characterization of the *Hansenula polymorpha* HOC1, OCH1, and OCR1 Genes as Members of the Yeast OCH1 Mannosyltransferase Family Involved in Protein Glycosylation", *The Journal of Biological Chemistry* 281(10):6261-6272 (2006).
Ramezani-Rad M. et al., "The *Hansenula Polymorpha* (strain CBS4732) Genome Sequencing and Analysis", *FEMS Yeast Research* 4:207-215 (2003).
Alani E. et al., "A Method for Gene Disruption that Allows Repeated Use of URA3 Selection in the Construction of Multiply Disrupted Yeast Strains", *Genetics* 116:541-545 (1987).

(Continued)

*Primary Examiner* — Quang Nguyen
(74) *Attorney, Agent, or Firm* — Scully, Scott, Murphy & Presser, P.C.

(57) ABSTRACT

The present invention provides genetically engineered strains of *Pichia* capable of producing proteins with reduced glycosylation. In particular, the genetically engineered strains of the present invention are capable of expressing either or both of an α-1,2-mannosidase and glucosidase II. The genetically engineered strains of the present invention can be further modified such that the OCH1 gene is disrupted. Methods of producing glycoproteins with reduced glycosylation using such genetically engineered stains of *Pichia* are also provided.

12 Claims, 23 Drawing Sheets

(56) References Cited

OTHER PUBLICATIONS

Nakayama Ken-ichi et al., "*OCH1* encodes a novel membrane bound mannosyltransferase: outer chain elongation of asparagines-linked oligosaccharides", *The EMBO Journal 11(7)*: 2511-2519 (1992).

Kniskern P. J. et al., "Characterization and evaluation of a recombinant hepatitis B vaccine expressed in yeast defective for *N*-linked Hyperglycosylation", *Vaccine 12(11)*: 1021-1025 (1994).

Lehle L. et al., "Glycoprotein biosynthesis in *Saccharomyces cerevisiae: ngd29*, an *N*-glycosylation mutant allelic to *och1* having a defect in the initiation of outer chain formation", *FEBS Letters 370*: 41-45 (1995).

Yoko-o T. et al., "*Schizosaccharomyces prombe och1*₊encodes α-1, 6-mannosyltransferase that is involved in outer chain elongation of *N*-linked oligosaccharides", *FEBS Letters 489*: 75-80 (2001).

Cregg J. M. et al., "High-Level Expression And Efficient Assembly Of Hepatitis B Surface Antigen In The Methylotrophic Yeast, *Pichia pastoris*", *Biotechnology 5*: 479-485 (1987).

Lai A. et al., "Substrate specificities of recombinant murine Golgi α1,2-mannosidases IA and IB and comparison with endoplasmic reticulum and Golgi processing α1,2-mannosidases", *Glycobiology 8(10)*: 981-995 (1998).

Tremblay L. O. et al., "Cloning and expression of a specific human α1,2-mannosidase that trims $Man_9$ $GlcNAc_2$ to $Man_8$ $GlcNAc_2$ isomer B during *N*-glycan biosynthesis", *Glycobiology 9(10)*: 1073-1078 (1999).

Gonzalez D. S. et al., "Identification, Expression, and Characterization of a cDNA Encoding Human Endoplasmic Reticulum Mannosidase I, the Enzyme That Catalyzes the First Mannose Trimming Step in Mammalian Asn-linked Oligosaccharide Biosynthesis", *The Journal of Biological Chemistry 274(30)*: 21375-21386 (1999).

Callewaert N. et al., "Use of HDEL-tagged *Trichoderma reesei* mannosyl oligosaccharide α1,2-α-D-mannosidase for N-glycan engineering in *Pichia pastoris*", FEBS Letters 503: 173-178 (2001).

Maras, M., et al. (2000) "Molecular Cloning and Enzymatic Characterization of a Trichoderma Reesi, 1, 2—α-D-Mannosidase", *Journal of Biotechnology 77*: 255-263.

Bretthauer, R. K., et al. (1999) "Glycosylation of *Pichia pastoris*-derviced Proteins", *Biotechnol. Appl. Biochem 30*: 193-200.

Kukuruzinska, M. A., et al. (1987) "Protein Glycosylation in Yeast", *Ann. Rev. Biochem 56*: 915-944.

Chiba, Y., et al. (1998) "Production of Human Cpmpatible High Mannse-Type ($Man_5GlcNAc_2$) Sugar Chains in *Saccharomyces cerevisiae*", *The Journal of Biological Chemistry 273 (41)*: 26298-26304.

Maras, M., et al. (1999) In Vivo Synthesis of Complex N-Glycans by Expression of Human N-Acetylglucosaminyltransferase I in the Filamentous Fungus *Trichoderma reesei*, *FEBS Letters 452*: 365-370.

Nakanishi-Shindo, Y., et al. (1993) "Structure of the N-Linked Oligosaccharides That Show the Complete Loss of α-1, 6-Polymannose Outer Chain from och1, och1 mnn1, and och1 mnn1 alg3 Mutants of *Saccharomyces cerevisiae*", *The Journal of Biological Chemistry 268 (35)*: 26338-26345.

Martinet, W. et al. (1998) "Modification of the Protein Glycosylation Pathway in the Methylotrophic Yeast *Pichia pastoris*", *Biotecnoogy Letters 20(12)*:1171-1177.

Maras, M., et al. (1997) "In Vitro Conversation of the Carbohydrate Moiety of Fungal Glycoproteins to Mammalian-Type Oligosaccharides", *Eur. J. Biochem.* 249:701-7707.

Laroy,W., et al. (2000) "Cloning of *Trypanosoma cruzi* trans-Sialidase and Expression in *Pichia pastoris*", *Protein Expression and Purification 20*: 389-393.

Inoue et al. Molecular cloning and nucleotide sequence of the 1,2-alpha-D-mannosidase gene, msdS, from *Aspergillus saitoi* and expression of the gene in yeast cells. Biochim. Biophys. Acta 1253:141-145, 1995.

Herscovics et al. Isolation of a mouse Golgi mannosidase cDNA, a member of a gene family conserved from yeast to mammals. J. Biol. Chem. 269:9864-9871, 1994.

Lal et al. Isolation and expression of murine and rabbit cDNAs encoding an alpha 1,2-mannosidase involved in the processing of asparagines-linked oligosaccharides. J. Biol. Chem. 269-9872-9881, 1995.

Trombetta et al. Endoplasmic recticulum glucosidase II is composed of a catalytic subunit, conserved from yeast to mammals, and a tightly bound noncatalytic HDEL-containing subunit. J. Biol. Chem. 271:27509-27516, 1996.

Ngo et al. Computational complexity, protein structure prediction, and the Levinthal Paradox. IN: The protein folding problem and tertiary structure prediction (Merz et al., Eds.), Birkhauser, Boston, 1994, pp. 491-495.

Rudinger, J. Characteristics of the amino acids as components of a peptide hormone sequence. In: Peptide hormones (Parsons, J.A., Ed.), University Park Press, Baltimore, 1976, pp. 1-7.

Grinna, L.S. et al., "Size Distribution and General Structural Features of N-linked oligosaccharides from the methylotrophic yeast, *Pichia pastoris* "Yeast (Mar.-Apr. 1989) pp. 107-115, vol. 5. No. 2.

Jungmann, J. et al., "The *Saccharomyces cerevisiae* protein Mnn10p/Bed1p is a subunit of a Golgi mannosyltransferase complex" J Biol Chem. (Mar. 5, 1999) pp. 6579-6585, vol. 274, No. 10.

Lee, B.N. et al., "The MAPKKK Ste11 regulates vegetative growth through a kinase cascade of shared signaling components" PNAS (Oct. 26, 1999) pp. 12679-12684, vol. 96, No. 22

Nakayama, K. et al., "Substrate specificity of α-1,6-mannosyltransferase that initiates N-linked mannose outer chain elongation in *Saccharomyces cerevisiae*" FEBS Letters (Aug. 4, 1997) pp. 547-550, vol. 412, No. 3.

Becker, B. et al., "The transmembrane domain of murine alpha-mannosidase IB is a major determinant of Golgi localization" European J. Cell Biol (Dec. 2000) pp. 79: 986-992, vol. 79, No. 12.

Choi, B.K. et al., "Use of combinatorial genetic libraries to humanize N-linked glycosylation in the yeast *Pichiapastoris*" PNAS (Apr. 29, 2003) pp. 5022-5027, vol. 100, No. 9.

Gonzalez, D.S. et al., "The α-Mannosidases: Phylogeny and Adaptive Diversification" Mol Biol Evolution (Nov. 2000) pp. 292-300, vol. 17, No. 2.

Herscovics, A. "Structure and Function of Class I α1,2-mannosidases Involved in Glycoprotem Synthesis and Endoplasmic Reticulum Quality Control" Biochimie (Aug. 2001) pp. 757-762, vol. 83, No. 8.

Higgins, D.R. at al., Methods in Moleculate Biology in *Pichia* Protocols, Higgins and Cregg (eds.) 1998, 10 pages.

Nett, J.H. at al., "A combinatorial genetic library approach to target heterologous glycosylation enzymes to the endoplasmic reticulum or the Golgi apparatus of *Pichia pastoris*" Yeast (Jan. 2011) pp. 237-252, vol. 28.

Schneikert, J. et al , "Characterization of a novel mouse recombinant processing α-mannosidase" Glycobiology (Apr. 1994) pp. 445-450, vol. 4, No. 4.

Bretthauer, R.K. et al., "Glycosylation of *Pichia pastoris*-derived Proteins" Biotechnol. Appl. Biochem (Dec. 1999) pp. 193-200, vol. 30.

\* cited by examiner

GlsII Pichia expression vector pYPT1ADE1glsII

GlsII Pichia expression vector pGAPADE1glsIIHDEL

Glucosidase II assay on commercially available alpha-glucosidase

Glucosidase II assay on heterologously expressed Pichia protein

SEQUENCE LISTING

<160> NUMBER OF SEQ ID NOS: 29

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence:synthetic peptide representing the ER-retention signal.

<400> SEQUENCE: 1

His Asp Glu Leu
1

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 2
gactggttcc aattgacaag c                                              21

<210> SEQ ID NO 3
<211> LENGTH: 44
<212> TYPE: DNA
<213> ORGANISM: Artificial Sequence
<220> FEATURE:
<223> OTHER INFORMATION: Description of Artificial Sequence:primer

<400> SEQUENCE: 3
agtctagatt acaactcgtc gtgagcaagg tggccgcccc gtcg                      44

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 4
ccattgagga cgcatgccgc gcc                                            23

<210> SEQ ID NO 5
<211> LENGTH: 85
<212> TYPE: DNA
<213> ORGANISM: Artificial Sequence
<220> FEATURE:
<223> OTHER INFORMATION: Description of Artificial Sequence:primer

<400> SEQUENCE: 5
gtatctagat tacaactcgt cgtgcagatc ctcttctgag atgagttttt gttcagcaag    60
gtggccgccc cgtcgtgatg atgaa                                          85

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 6
aactcgagat ggactcttca aaacacaaac gc                                  32

<210> SEQ ID NO 7
<211> LENGTH: 46
<212> TYPE: DNA
<213> ORGANISM: Artificial Sequence
<220> FEATURE:
<223> OTHER INFORMATION: Description of Artificial Sequence:primer

<400> SEQUENCE: 7
ttgcggccgc ttacaactcg tcgtgtcgga cagcaggatt acctga        46

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 8
ccattgagga cgcatgccgc gcc        23

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 9
gcaaatggca ttctgacatc ct        22

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 10
gtccctattt caatcaattg aa        22

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 11
gactggttcc aattgacaag c        21

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 12
ccgctcgaga tggtcctttt gaaatggctc        30

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence:primer

<400> SEQUENCE: 13

```
ccgggcccaa aaataacttc ccaatcttca g                                          31
```

<210> SEQ ID NO 14
<211> LENGTH: 1785
<212> TYPE: DNA
<213> ORGANISM: Artificial Sequence
<220> FEATURE:
<223> OTHER INFORMATION: Description of Artificial Sequence:The ORF
      sequence of the MFManHDEL fusion in
      pGAPZMFManHDEL.

<400> SEQUENCE: 14

```
atgagatttc cttcaattttt tactgctgtt ttattcgcag catcctccgc attagctgct         60
ccagtcaaca ctacaacaga agatgaaacg gcacaaattc cggctgaagc tgtcatcggt        120
tactcagatt tagaagggga tttcgatgtt gctgttttgc cattttccaa cagcacaaat        180
aacgggttat tgtttataaa tactactatt gccagcattg ctgctaaaga agaagggta         240
tctctcgaga aaagagaggc tgaagctgaa ttcgccacaa acgtggatc tcccaaccct         300
acgagggcgg cagcagtcaa ggccgcattc cagacgtcgt ggaacgctta ccaccatttt        360
gcctttcccc atgacgacct ccacccggtc agcaacagct tgatgatga gagaaacggc         420
tggggctcgt cggcaatcga tggcttggac acggctatcc tcatgggga tgccgacatt         480
gtgaacacga tccttcagta tgtaccgcag atcaacttca ccacgactgc ggttgccaac        540
caaggatcct ccgtgttcga gaccaacatt cggtacctcg gtggcctgct ttctgcctat        600
gacctgttgc gaggtccttt cagctccttg gcgacaaacc agaccctggt aaacagcctt        660
ctgaggcagg ctcaaacact ggccaacggc tcaaggttg cgttcaccac tcccagcggt         720
gtcccggacc ctaccgtctt cttcaaccct actgtccgga aagtggtgc atctagcaac         780
aacgtcgctg aaattggaag cctggtgctc gagtggacac ggttgagcga cctgacggga        840
aacccgcagt atgcccagct tgcgcagaag ggcgagtcgt atctcctgaa tccaaaggga        900
agcccggagg catggcctgg cctgattgga acgtttgtca gcacgagcaa cggtaccttt        960
caggatagca gcggcagctg gtccggcctc atggacagct tctacgagta cctgatcaag       1020
atgtacctgt acgacccggt tgcgtttgca cactacaagg atcgctgggt ccttggtgcc       1080
gactcgacca ttgggcatct cggctctcac ccgtcgacgc gcaaggactt gaccttttg        1140
tcttcgtaca acggacagtc tacgtcgcca aactcaggac atttggccag ttttggcggt       1200
ggcaacttca tcttgggagg cattctcctg aacgagcaaa agtacattga ctttggaatc       1260
aagcttgcca gctcgtactt tggcacgtac acccagacgg cttctggaat cggccccgaa       1320
ggcttcgcgt gggtggacag cgtgacgggc ccggcggct cgccgccctc gtcccagtcc        1380
gggttctact cgtcggcagg attctggtg acggcaccgt attacatcct gcggccggag        1440
acgctggaga gcttgtacta cgcataccgc gtcacgggcg actccaagtg caggacctg        1500
gcgtgggaag cgttgagtgc cattgaggac gcatgccgcg ccggcagcgc gtactcgtcc       1560
atcaacgacg tgacgcaggc caacggcggg ggtgcctctg acgatatgga gagcttctgg       1620
tttgccgagg cgctcaagta tgcgtacctg atctttgcgg aggagtcgga tgtgcaggtg       1680
caggccaccg gcgggaacaa atttgtcttt aacacggagg cgcaccccctt tagcatccgt       1740
tcatcatcac gacggggcgg ccaccttgct cacgacgagt tgtaa                       1785
```

<210> SEQ ID NO 15
<211> LENGTH: 2016
<212> TYPE: DNA

<213> ORGANISM: Artificial Sequence
<220> FEATURE:
<223> OTHER INFORMATION: Description of Artificial Sequence:The ORF
      sequence of the MFmManHDEL fusion in
      pGAPZMFmManHDEL.

<400> SEQUENCE: 15

```
atgagatttc cttcaatttt tactgctgtt ttattcgcag catcctccgc attagctgct      60
ccagtcaaca ctacaacaga agatgaaacg gcacaaattc cggctgaagc tgtcatcggt     120
tactcagatt tagaagggga tttcgatgtt gctgttttgc cattttccaa cagcacaaat     180
aacgggttat tgtttataaa tactactatt gccagcattg ctgctaaaga agaaggggta     240
tctctcgaga tggactcttc aaaacacaaa cgctttgatc tgggcttaga agatgtgtta     300
attcctcacg tagatgccgg caaaggagct aaaaaccccg cgtcttcct gatccatgga      360
cccgacgaac acagacacag ggaagaagaa gagcgtctga aaataagat tagagctgac     420
catgagaaag ccctggaaga agcaaaagaa aaattaagaa agtcaagaga ggaaatccgt     480
gcagaaattc agacagagaa aaacaaagta gcccaagcaa tgaagacaaa agagaccagg     540
gtactgccgc ctgtccctgt ccacaacgt gtagggtca gtggtgggga tccagaagac       600
atggagatca agaagaaaag agacaaaatt aaagagatga tgaaacatgc ctgggataat     660
tacagaacat acgatggggg acataatgaa ctaaggccta ttgcaaggaa aggccattcc     720
actaacatat tcggaagctc acagatgggt gccaccatag tggatgcttt ggatacccctt    780
tatatcatgg ggcttcatga tgaattcatg gatgggcaaa gatggattga agaaaacctt    840
gatttcagtg tgaattcaga agtgtctgtc tttgaagtta acattcgctt tattggaggg    900
ctcctcgctg catattacct gtcaggagag gaaatattca agactaaagc agtgcagttg    960
gctgagaaac tccttcctgc ctttaacaca cctactggga ttccctgggc aatggtgaac   1020
ctgaaaagtg gagtaggtcg aaactggggc tgggcgtctg caggcagcag catcctggct   1080
gagttcggca ccctgcacat ggagtttgtg cacctcagct acttgaccgg tgacttgact   1140
tactataata aggtcatgca cattcggaaa ctactgcaga aaatggaacg cccaaatggt   1200
ctttatccaa attatttaaa cccaagaaca gggcgctggg gtcagtatca cacatcagtt   1260
ggtggtctgg gagatagttt ttatgaatac ttactgaaag catggctgac gtcagataaa   1320
acagaccacg aggcaagaag gatgtatgac gatgctgttg aggctataga aaacatctt    1380
attaagaagt cccgaggagg tctggttttt attggagaat ggaagaatgg acacttggaa   1440
aggaagatgg ggcacttggc ctgctttgct gggggaatgc ttgcccttgg agcagatggt   1500
tccagaaagg ataaagctgg ccactactta gaactagggg cagaaattgc acgaacatgt   1560
catgagtcat atgacagaac tgcattgaaa ctaggtccgg agtcattcaa gtttgatggt   1620
gcagtggaag ccgtggctgt gcggcaggct gaaaagtatt acatccttcg tccagaagta   1680
attgaaacct attggtatct atggcgattt acccacgacc caagatacag gcagtggggc   1740
tgggaagcag cactggctat tgagaagtcg tgccgggtca gcggtgggtt ttctggtgtc   1800
aaggatgtat acgccccgac ccctgtgcat gacgacgtgc agcagagctt ttctcttgct   1860
gaaacattaa atacttgta cctgctgttc tctggcgatg accttctacc tttagaccac   1920
tgggtgttta acagagaggc gcaccctctg ccggtgttgc gcttagccaa cagcactctt   1980
tcaggtaatc ctgctgtccg acacgacgag ttgtaa                              2016
```

<210> SEQ ID NO 16
<211> LENGTH: 6757
<212> TYPE: DNA

<213> ORGANISM: Artificial Sequence
<220> FEATURE:
<223> OTHER INFORMATION: Description of Artificial Sequence:Sequence of plasmid pAOX2ZAGLSII.

<400> SEQUENCE: 16

```
catggccaag ttgaccagtg ccgttccggt gctcaccgcg cgcgacgtcg ccggagcggt    60
cgagttctgg accgaccggc tcgggttctc ccgggacttc gtggaggacg acttcgccgg   120
tgtggtccgg gacgacgtga ccctgttcat cagcgcggtc caggaccagg tggtgccgga   180
caacaccctg gcctgggtgt gggtgcgcgg cctggacgag ctgtacgccg agtggtcgga   240
ggtcgtgtcc acgaacttcc gggacgcctc cgggccggcc atgaccgaga tcggcgagca   300
gccgtggggg cgggagttcg ccctgcgcga cccggccggc aactgcgtgc acttcgtggc   360
cgaggagcag gactgacacg tccgacggcg gcccacgggg cccaggcctc ggagatccgt   420
cccccttttc ctttgtcgat atcatgtaat tagttatgtc acgcttacat tcacgccctc   480
cccccacatc cgctctaacc gaaaggaag gagttagaca acctgaagtc taggtcccta   540
tttattttt tatagttatg ttagtattaa gaacgttatt tatatttcaa attttcttt    600
tttttctgta cagacgcgtg tacgcatgta acattatact gaaaaccttg cttgagaagg   660
ttttgggacg ctcgaaggct ttaatttgca agctggagac caacatgtga gcaaaaggcc   720
agcaaaaggc caggaaccgt aaaaaggccg cgttgctggc gttttccat aggctccgcc    780
ccctgacga gcatcacaaa aatcgacgct caagtcagag gtggcgaaac ccgacaggac   840
tataaagata ccaggcgttt ccccctggaa gctccctcgt gcgctctcct gttccgaccc   900
tgccgcttac cggatacctg tccgcctttc tcccttcggg aagcgtggcg ctttctcaat   960
gctcacgctg taggtatctc agttcggtgt aggtcgttcg ctccaagctg ggctgtgtgc  1020
acgaaccccc cgttcagccc gaccgctgcg ccttatccgg taactatcgt cttgagtcca  1080
acccggtaag acacgactta tcgccactgg cagcagccac tggtaacagg attagcagag  1140
cgaggtatgt aggcggtgct acagagttct tgaagtggtg gcctaactac ggctacacta  1200
gaaggacagt atttggtatc tgcgctctgc tgaagccagt taccttcgga aaaagagttg  1260
gtagctcttg atccggcaaa caaaccaccg ctggtagcgg tggttttttt gtttgcaagc  1320
agcagattac gcgcagaaaa aaaggatctc aagaagatcc tttgatcttt tctacggggt  1380
ctgacgctca gtggaacgaa aactcacgtt aagggatttt ggtcatgaga tcagatcttt  1440
ttttcagacc atatgaccgg tccatcttct acgggggat tatctatgct ttgacctcta  1500
tcttgattct tttatgattc aaatcacttt tacgttattt attacttact ggttatttac  1560
ttagcgcctt ttctgaaaaa catttactaa aaatcataca tcggcactct caaacacgac  1620
agattgtgat caagaagcag agacaatcac cactaaggtt gcacatttga gccagtaggc  1680
tcctaataga ggttcgatac ttattttgat aatacgacat attgtcttac ctctgaatgt  1740
gtcaatactc tctcgttctt cgtctcgtca gctaaaaata taacacttcg agtaagatac  1800
gcccaattga aggctacgag ataccagact atcactagta gaactttgac atctgctaaa  1860
gcagatcaaa tatccattta tccagaatca attaccttcc tttagcttgt cgaaggcatg  1920
aaaaagctac atgaaaatcc ccatccttga agttttgtca gcttaaagga ctccattccc  1980
taaaatttca agcagtcctc tcaactaaat tttttccat tcctctgcac ccagccctct   2040
tcatcaaccg tccagccttc tcaaaagtcc aatgtaagta gcctgcaaat tcaggttaca  2100
acccctcaat tttccatcca agggcgatcc ttacaaagtt aatatcgaac agcagagact  2160
aagcgagtca tcatcaccac ccaacgatgg tgaaaaactt aagcataga ttgatggagg   2220
```

```
gtgtatggca cttggcggct gcattagagt ttgaaactat ggggtaatac atcacatccg   2280
gaactgatcc gactccgaga tcatatgcaa agcacgtgat gtaccccgta aactgctcgg   2340
attatcgttg caattcatcg tcttaaacag tacaagaaac tttattcatg ggtcattgga   2400
ctctgatgag gggcacattt ccccaatgat tttttgggaa agaaagccgt aagaggacag   2460
ttaagcgaaa gagacaagac aacgaacagc aaaagtgaca gctgtcagct acctagtgga   2520
cagttgggag tttccaattg gttggttttg aattttacc catgttgagt tgtccttgct    2580
tctccttgca acaatgcaa gttgataaga catcaccttc caagataggc tattttgtc     2640 gcataaattt ttgtctcgga gtgaaaaccc cttttatgtg aacagattac agaagcgtcc   2700
tacccttcac cggttgagat ggggagaaaa ttaagcgatg aggagacgat tattggtata   2760
aaagaagcaa ccaaaatccc ttattgtcct tttctgatca gcatcaaaga atattgtctt   2820
aaaacgggct tttaactaca ttgttcttac acattgcaaa cctcttcctt ctatttcgga   2880
tcaactgtat tgactacatt gatctttttt aacgaagttt acgacttact aaatccccac   2940
aaacaaatca actgagaaaa gaattcacgt ggcccagccg gccgtctcgg atcggtacct   3000
cgagatggtc cttttgaaat ggctcgtatg ccaattggtc ttctttaccg cttttttcgca 3060 tgcgtttacc gactatctat taaagaagtg tgcgcaatct gggttttgcc atagaaacag  3120
ggtttatgca gaaatattg ccaaatctca tcactgctat tacaaagtgg acgccgagtc   3180
tattgcacac gatcctttag agaatgtgct tcatgctacc ataattaaaa ctataccaag   3240
attggagggc gatgatatag ccgttcagtt cccattctct ctctctttttt tacaggatca  3300 ctcagtaagg ttcactataa atgagaaaga gagaatgcca accaacagca gcggtttgtt   3360
gatctcttca caacggttca atgagacctg gaagtacgca ttcgacaaga aatttcaaga   3420
ggaggcgaac aggaccagta ttccacaatt ccacttcctt aagcaaaaac aaactgtgaa   3480
ctcattctgg tcgaaaatat cttcattttt gtcactttca aactccactg cagacacatt   3540
tcatcttcga aacggtgatg tatccgtaga atctttgct gaaccttttc aattgaaagt    3600
ttactggcaa aatgcgctga aacttattgt aaacgagcaa aatttcctga cattgaaca    3660 tcatagaact aagcaggaaa acttcgcaca cgtgctgcca gaagaaacaa ctttcaacat   3720
gtttaaggac aatttcttgt attcaaagca tgactctatg cctttggggc ctgaatcggt   3780
tgcgctagat ttctctttca tgggttctac taatgtctac ggtataccgg aacatgcgac   3840
gtcgctaagg ctgatggaca cttcaggtgg aaaggaaccc tacaggcttt tcaacgttga   3900
tgtctttgag tacaacatcg gtaccagcca accaatgtac ggttcgatcc cattcatgtt   3960
ttcatcttcg tccacatcta tcttttgggt caatgcagct gacacttggg tagacataaa   4020
gtatgacacc agtaaaaata aaacgatgac tcattggatc tccgaaaatg gtgtcataga   4080
tgtagtcatg tccctggggc cagatattcc aactatcatt gacaaattta ccgatttgac   4140
tggtagaccc ttttaccgc ccatttcctc tatagggtac catcaatgta gatggaatta    4200
taatgatgag atggacgttc tcacagtgga ctctcagatg gatgctcata tgattccta    4260 cgattttatt tggttggact tggagtatac gaacgacaaa aaatattta cttggaagca    4320 gcactccttt cccaatccaa aaaggctgtt atccaaatta aaaagttgg gtagaaatct    4380 tgtcgtacta atcgatcctc atttaaagaa agattatgaa atcagtgaca gggtaattaa   4440
tgaaaatgta gcagtcaagg atcacaatgg aaatgactat gtaggtcatt gctggccagg   4500
taattctata tggattgata ccataagcaa atatggccaa aagatttgga agtcctttt    4560 cgaacggttt atggatctgc cggctgattt aactaattta ttcatttgga atgatatgaa   4620
```

```
cgagccttcg attttcgatg gcccagagac cacagctcca aaagatttga ttcacgacaa    4680
ttacattgag gaaagatccg tccataacat atatggtcta tcagtgcatg aagctactta    4740
cgacgcaata aaatcgattt attcaccatc cgataagcgt cctttccttc taacaagggc    4800 ttttttttgcc ggctctcaac gtactgctgc cacatggact ggtgacaatg tggccaattg   4860
ggattactta aagatttcca ttcctatggt tctgtcaaac aacattgctg gtatgccatt    4920
tataggagcc gacatagctg gctttgctga ggatcctaca cctgaattga ttgcacgttg    4980
gtaccaagcg ggcttatggt acccattttt tagagcacac gcccatatag acaccaagag    5040
aagagaacca tacttattca atgaaccttt gaagtcgata gtacgtgata ttatccaatt    5100
gagatatttc ctgctaccta ccttatacac catgtttcat aaatcaagtg tcactggatt    5160
tccgataatg aatccaatgt ttattgaaca ccctgaattt gctgaattgt atcatatcga    5220
taaccaattt tactggagta attcaggtct attagtcaaa cctgtcacgg agcctggtca    5280
atcagaaacg gaaatggttt tcccacccgg tatattctat gaattcgcat ctttacactc    5340
ttttataaac aatggtactg atttgataga aaagaatatt tctgcaccat tggataaaat    5400
tccattattt attgaaggcg gtcacattat cactatgaaa gataagtata gaagatcttc    5460
aatgttaatg aaaaacgatc catatgtaat agttatagcc cctgataccg agggacgagc    5520
cgttggagat ctttatgttg atgatggaga aacttttggc taccaaagag gtgagtacgt    5580
agaaactcag ttcattttcg aaaacaatac cttaaaaaat gttcgaagtc atattcccga    5640
gaatttgaca ggcattcacc acaatacttt gaggaatacc aatattgaaa aaatcattat    5700
cgcaaagaat aatttacaac acaacataac gttgaaagac agtattaaag tcaaaaaaaa    5760
tggcgaagaa agttcattgc cgactagatc gtcatatgag aatgataata agatcaccat    5820
tcttaaccta tcgcttgaca taactgaaga ttgggaagtt attttggc ccgaacaaaa      5880 actcatctca gaagaggatc tgaatagcgc cgtcgaccat catcatcatc atcattgagt    5940
tttagcctta gacatgactg ttcctcagtt caagttgggc acttacgaga agaccggtct    6000
tgctagattc taatcaagag gatgtcagaa tgccatttgc ctgagagatg caggcttcat    6060
ttttgatact tttttatttg taacctatat agtataggat ttttttttgtc attttgtttc    6120 ttctcgtacg agcttgctcc tgatcagcct atctcgcagc tgatgaatat cttgtggtag    6180
gggtttggga aaatcattcg agtttgatgt ttttcttggt atttcccact cctcttcaga    6240
gtacagaaga ttaagtgaga ccttcgtttg tgcggatccc ccacacacca tagcttcaaa    6300
atgtttctac tcctttttta ctcttccaga ttttctcgga ctccgcgcat cgccgtacca    6360
cttcaaaaca cccaagcaca gcatactaaa ttttccctct ttcttcctct agggtgtcgt    6420
taattacccg tactaaaggt ttggaaaaga aaaagagac cgcctcgttt cttttttcttc    6480 gtcgaaaaag gcaataaaaa ttttttatcac gtttctttttt cttgaaattt ttttttttag   6540 ttttttttctc tttcagtgac ctccattgat atttaagtta ataaacggtc ttcaatttct    6600
caagtttcag tttcattttt cttgttctat tacaactttt tttacttctt gttcattaga    6660
aagaaagcat agcaatctaa tctaagggcg gtgttgacaa ttaatcatcg gcatagtata    6720
tcggcatagt ataatacgac aaggtgagga actaaac                             6757
```

<210> SEQ ID NO 17
<211> LENGTH: 8272
<212> TYPE: DNA
<213> ORGANISM: Artificial Sequence
<220> FEATURE:
<223> OTHER INFORMATION: Description of Artificial Sequence:Sequence of plasmid pAOX2ADE1glsII.

<400> SEQUENCE: 17

```
tcgaccggct gcattaatga atcggccaac gcgcggggag aggcggtttg cgtattgggc    60
gctcttccgc ttcctcgctc actgactcgc tgcgctcggt cgttcggctg cggcgagcgg   120
tatcagctca ctcaaaggcg gtaatacggt tatccacaga atcagggdat aacgcaggaa   180
agaacatgtg agcaaaaggc cagcaaaagg ccaggaaccg taaaaaggcc gcgttgctgg   240
cgttttttcca taggctccgc cccctgacg agcatcacaa aaatcgacgc tcaagtcaga   300
ggtggcgaaa cccgacagga ctataaagat accaggcgtt tccccctgga agctccctcg   360
tgcgctctcc tgttccgacc ctgccgctta ccggatacct gtccgccttt ctcccttcgg   420
gaagcgtggc gctttctcat agctcacgct gtaggtatct cagttcggtg taggtcgttc   480
gctccaagct gggctgtgtg cacgaacccc ccgttcagcc cgaccgctgc gccttatccg   540
gtaactatcg tcttgagtcc aacccggtaa gacacgactt atcgccactg gcagcagcca   600
ctggtaacag gattagcaga gcgaggtatg taggcggtgc tacagagttc ttgaagtggt   660
ggcctaacta cggctacact agaaggacag tatttggtat ctgcgctctg ctgaagccag   720
ttaccttcgg aaaaagagtt ggtagctctt gatccggcaa acaaaccacc gctggtagcg   780
gtggtttttt tgtttgcaag cagcagatta cgcgcagaaa aaaaggatct caagaagatc   840
ctttgatctt ttctacgggg tctgacgctc agtggaacga aaactcacgt taagggattt   900
tggtcatgag attatcaaaa aggatcttca cctagatcct tttaaattaa aaatgaagtt   960
ttaaatcaat ctaaagtata tatgagtaaa cttggtctga cagttaccaa tgcttaatca  1020
gtgaggcacc tatctcagcg atctgtctat ttcgttcatc catagttgcc tgactccccg  1080
tcgtgtagat aactacgata cgggagggct taccatctgg ccccagtgct gcaatgatac  1140
cgcgagaccc acgctcaccg gctccagatt tatcagcaat aaaccagcca gccggaaggg  1200
ccgagcgcag aagtggtcct gcaactttat ccgcctccat ccagtctatt aattgttgcc  1260
gggaagctag agtaagtagt tcgccagtta atagtttgcg caacgttgtt gccattgcta  1320
caggcatcgt ggtgtcacgc tcgtcgtttg gtatggcttc attcagctcc ggttcccaac  1380
gatcaaggcg agttacatga tcccccatgt tgtgcaaaaa agcggttagc tccttcggtc  1440
ctccgatcgt tgtcagaagt aagttggccg cagtgttatc actcatggtt atggcagcac  1500
tgcataattc tcttactgtc atgccatccg taagatgctt ttctgtgact ggtgagtact  1560
caaccaagtc attctgagaa tagtgtatgc ggcgaccgag ttgctcttgc ccggcgtcaa  1620
tacgggataa taccgcgcca catagcagaa ctttaaaagt gctcatcatt ggaaaacgtt  1680
cttcggggcg aaaactctca aggatcttac cgctgttgag atccagttcg atgtaaccca  1740
ctcgtgcacc caactgatct tcagcatctt ttactttcac cagcgtttct gggtgagcaa  1800
aaacaggaag gcaaaatgcc gcaaaaaagg gaataagggc gacacggaaa tgttgaatac  1860
tcatactctt cctttttcaa tagctccaag gcaacaaatt gactactcag accgacattc  1920
attcgttatt gattttaaat caacgataaa cggaatggtt acttgaatga tttcacttta  1980
tgatcattgt ttactaatta cctaaatagg attttatatg gaattggaag aataagggaa  2040
atttcagatg tctgaaaaag gcgaggaggg tactaatcat tcaagcccat tcttgccag   2100
taattgcttc ataagcttca atatacttttt ctttactctt gatagcaatt tctgcatcca  2160
tggctacgcc ctcttgcca ttcaatccgt tggccgtcaa ccaatctctg agaaactgct   2220
tatcgtaact ctcttgcgat ttacccactt ggtaagtctt ttgattccaa aatctagaag  2280
```

```
aatctggagt taaaacttca tctactagta ccaattcatt gttttcgtcc agtccaaatt    2340
cgaatttcgt atcagcaata atgatcccct tcaaaagggc gaagtttttt gcagcagaat    2400
acaactcgac cgccttgaca gcgaccttct cacaaatgtc tttacctaca atctcagcag    2460
cttgttcaat agagatgttt tcatcgtgtt caccctgttc agctttcgtt gaaggtgtga    2520
aaatcggagt tggaaaggcg tcgctctctt gaaggttctc gttttcaacc ttgactccat    2580
ggacagtttt tgagttcttg tactcttcc atgcacttcc agtgatgtaa cctctgacaa    2640
tggcttccaa aggtatcagt ctgtgctttt ttactatcaa ggatcgtccc tctaattgag    2700
atttgtattt tcttcagac agttttgatg gtagtaaagc aaagacttcc ttgtcattag    2760
aagcaaccaa atgattcttt atgtagggtg ccaaaaaatc aaaccagaaa actgagagct    2820
gagtcaaaat ctttccctta tcaggaatac cgtttgtcat aatcacatcg taagcggaga    2880
tacggtcagt tgcgacgaac agcaagttgt tctcatcgac tgcataaatg tctctaacct    2940
ttcctttggc gattaaaggt aggattccgt ccagatcagt gttcacaatg gacatacttg    3000
gaaggataca gcaaagtgtg ttggaagcga tgacacatgg aaaggaattt ttcgagtttc    3060
ctagagtagt atattgggc ggtgaaagtt cagatgttta atgcttaata ctcttatact    3120
cttcaaagcg cccaagtgtt tctgccaacc tgactttttt ctgaataatg aatcgttcaa    3180
gtggagtatt taaccatga ttaagttacg tgatttggca ctggataagg tcgaaaaata    3240
tccgtattca taaacgatta ttggtaaaag ttacaaaata ccactaatta cggagaagct    3300
tagtaacagt tatcatctct tggtcgatta acgcttacaa tttccattcg ccattcaggc    3360
tgcgcaactg ttgggaaggg cgatcggtgc gggcctcttc gctattacgc cagggcctcg    3420
aggcacaaac gaacgtctca cttaatcttc tgtactctga agaggagtgg gaaataccaa    3480
gaaaaacatc aaactcgaat gattttccca acccctacc acaagatatt catcagctgc    3540
gagataggct gatcaggagc aagctcgtac gagaagaaac aaaatgacaa aaaaaatcct    3600
atactatata ggttacaaat aaaaaagtat caaaaatgaa gcctgcatct ctcaggcaaa    3660
tggcattctg acatcctctt gattagaatc tagcaagacc ggtcttctcg taagtgccca    3720
acttgaactg aggaacagtc atgtctaagg ctaaaactca atgatgatga tgatgatggt    3780
cgacggcgct attcagatcc tcttctgaga tgagttttg ttcgggccca aaaataactt    3840
cccaatcttc agttatgtca agcgataggt taagaatggt gatcttatta tcattctcat    3900
atgacgatct agtcggcaat gaactttctt cgccattttt tttgacttta atactgtctt    3960
tcaacgttat gttgtgttgt aaattattct ttgcgataat gatttttca atattggtat    4020
tcctcaaagt attgtggtga atgcctgtca aattctcggg aatatgactt cgaacatttt    4080
ttaaggtatt gttttcgaaa atgaactgag tttctacgta ctcacctctt tggtagccaa    4140
aagtttctcc atcatcaaca taaagatctc caacggctcg tccctcggta tcagggcta    4200
taactattac atatggatcg ttttcatta acattgaaga tcttctatac ttatcttca    4260
tagtgataat gtgaccgcct tcaataaata atggaatttt atccaatggt gcagaaatat    4320
tcttttctat caaatcagta ccattgttta taaaagagtg taaagatgcg aattcataga    4380
atataccggg tgggaaaacc atttccgttt ctgattgacc aggctccgtg acaggtttga    4440
ctaatagacc tgaattactc cagtaaaatt ggttatcgat atgatacaat tcagcaaatt    4500
cagggtgttc aataaacatt ggattcatta tcggaaatcc agtgacactt gatttatgaa    4560
acatggtgta taaggtaggt agcaggaaat atctcaattg gataatatca cgtactatcg    4620
acttcaaagg ttcattgaat aagtatggtt ctcttctctt ggtgtctata tgggcgtgtg    4680
```

```
ctctaaaaaa tgggtaccat aagcccgctt ggtaccaacg tgcaatcaat tcaggtgtag    4740
gatcctcagc aaagccagct atgtcggctc tataaatgg  cataccagca atgttgtttg    4800
acagaaccat aggaatggaa atctttaagt aatcccaatt ggccacattg tcaccagtcc    4860
atgtggcagc agtacgttga gagccggcaa aaaaagccct tgttagaagg aaaggacgct    4920
tatcggatgg tgaataaatc gattttattg cgtcgtaagt agcttcatgc actgatagac    4980
catatatgtt atggacggat cttcctcaa  tgtaattgtc gtgaatcaaa tcttttggag    5040
ctgtggtctc tgggccatcg aaaatcgaag gctcgttcat atcattccaa atgaataaat    5100
tagttaaatc agccggcaga tccataaacc gttcgaaaaa ggacttccaa atcttttggc    5160
catatttgct tatggtatca atccatatag aattacctgg ccagcaatga cctacatagt    5220
catttccatt gtgatccttg actgctacat tttcattaat taccctgtca ctgatttcat    5280
aatcttcttt taaatgagga tcgattagta cgacaagatt tctacccaac ttttttaatt    5340
tggataacag cctttttgga ttgggaaagg agtgctgctt ccaagtaaaa tattttttgt    5400
cgttcgtata ctccaagtcc aaccaaataa aatcgtaagg aatcatatga gcatccatct    5460
gagagtccac tgtgagaacg tccatctcat cattataatt ccatctacat tgatggtacc    5520
ctatagagga atgggcggt  aaaaagggtc taccagtcaa atcggtaaat tgtcaatga     5580 tagttggaat atctgccccc agggacatga ctacatctat gacaccattt tcggagatcc    5640
aatgagtcat cgtttatttt ttactggtgt catacttat  gtctacccaa gtgtcagctg    5700
cattgaccca aaagatagat gtggacgaag atgaaaacat gaatgggatc gaaccgtaca    5760
ttggttggct ggtaccgatg ttgtactcaa agacatcaac gttgaaaagc ctgtagggtt    5820
cctttccacc tgaagtgtcc atcagcctta gcgacgtcgc atgttccggt ataccgtaga    5880
cattagtaga acccatgaaa gagaaatcta gcgcaaccga ttcaggcccc aaaggcatag    5940
agtcatgctt tgaatacaag aaattgtcct taaacatgtt gaaagttgtt tcttctggca    6000
gcacgtgtgc gaagttttcc tgcttagttc tatgatgttc aatgttcagg aaattttgct    6060
cgtttacaat aagtttcagc gcattttgcc agtaaacttt caattgaaaa ggttcagcaa    6120
agatttctac ggatacatca ccgtttcgaa gatgaaatgt gtctgcagtg gagtttgaaa    6180
gtgacaaaaa tgaagatatt ttcgaccaga atgagttcac agtttgtttt tgcttaagga    6240
agtggaattg tggaatactg gtcctgttcg cctcctcttg aaatttcttg tcgaatgcgt    6300
acttccaggt ctcattgaac cgttgtgaag agatcaacaa accgctgctg ttggttggca    6360
ttctctcttt ctcatttata gtgaacctta ctgagtgatc ctgtaaaaaa gagagagaga    6420
atgggaactg aacggctata tcatcgccct ccaatcttgg tatagtttta attatggtag    6480
catgaagcac attctctaaa ggatcgtgtg caatagactc ggcgtccact tgtaatagc     6540 agtgatgaga tttggcaata ttttctgcat aaaccctgtt tctatggcaa acccagatt     6600 gcgcacactg ctttaataga tagtcggtaa acgcatgcga aaaagcggta agaagacca     6660 attggcatac gagccatttc aaaaggacca tctcgaggta ccgatccgag acggccggct    6720
gggccacgtg aattctttc  tcagttgatt tgtttgtggg gatttagtaa gtcgtaaact    6780
tcgttaaaaa agatcaatgt agtcaataca gttgatccga aatagaagga agaggtttgc    6840
aatgtgtaag aacaatgtag ttaaaagccc gttttaagac aatattcttt gatgctgatc    6900
agaaaaggac aataagggat tttggttgct tcttttatac caataatcgt ctcctcatcg    6960
cttaattttc tccccatctc aaccggtgaa gggtaggacg cttctgtaat ctgttcacat    7020 aaaagggggtt ttcactccga gacaaaaatt tatgcgacaa aaatagccta tcttggaagg    7080
```

-continued

```
tgatgtctta tcaacttgca ttgtttgcaa ggagaagcaa ggacaactca acatgggtaa    7140
aaattcaaaa ccaaccaatt ggaaactccc aactgtccac taggtagctg acagctgtca    7200
cttttgctgt tcgttgtctt gtctctttcg cttaactgtc ctcttacggc tttctttccc    7260
aaaaaatcat tggggaaatg tgcccctcat cagagtccaa tgacccatga ataaagtttc    7320
ttgtactgtt taagacgatg aattgcaacg ataatccgag cagtttacgg ggtacatcac    7380
gtgctttgca tatgatctcg gagtcggatc agttccggat gtgatgtatt accccatagt    7440
ttcaaactct aatgcagccg ccaagtgcca tacaccctcc atcaatctat gcttaaagtt    7500
tttcaccatc gttgggtggt gatgatgact cgcttagtct ctgctgttcg atattaactt    7560
tgtaaggatc gcccttggat ggaaaattga ggggttgtaa cctgaatttg caggctactt    7620
acattggact tttgagaagg ctggacggtt gatgaagagg gctgggtgca gaggaatgga    7680
aaaaaattta gttgagagga ctgcttgaaa ttttaggaaa tggagtcctt taagctgaca    7740
aaacttcaag gatggggatt ttcatgtagc tttttcatgc cttcgacaag ctaaaggaag    7800
gtaattgatt ctggataaat ggatatttga tctgctttag cagatgtcaa agttctacta    7860
gtgatagtct ggtatctcgt agccttcaat tgggcgtatc ttactcgaag tgttatattt    7920
ttagctgacg agacgaagaa cgagagagta ttgacacatt cagaggtaag acaatatgtc    7980
gtattatcaa aataagtatc gaacctctat taggagccta ctggctcaaa tgtgcaacct    8040
tagtggtgat tgtctctgct tcttgatcac aatctgtcgt gtttgagagt gccgatgtat    8100 gattttagt aaatgttttt cagaaaaggc gctaagtaaa taaccagtaa gtaataaata    8160
acgtaaaagt gatttgaatc ataaaagaat caagatagag gtcaaagcat agataatccc    8220
cccgtagaag atggaccggt catatggtct gaaaaaaaga tctgatctca tg    8272
```

<210> SEQ ID NO 18
<211> LENGTH: 5727
<212> TYPE: DNA
<213> ORGANISM: Artificial Sequence
<220> FEATURE:
<223> OTHER INFORMATION: Description of Artificial Sequence:Sequence of plasmid pGAPZAGLSII.

<400> SEQUENCE: 18

```
tcgagatggt cctttttgaaa tggctcgtat gccaattggt cttctttacc gcttttttcgc    60 atgcgtttac cgactatcta ttaaagaagt gtgcgcaatc tgggttttgc catagaaaca   120
gggtttatgc agaaaatatt gccaaatctc atcactgcta ttacaaagtg gacgccgagt   180
ctattgcaca cgatccttta gagaatgtgc ttcatgctac cataattaaa actataccaa   240
gattggaggg cgatgatata gccgttcagt tcccattctc tctctctttt ttacaggatc   300
actcagtaag gttcactata aatgagaaag agagaatgcc aaccaacagc agcggtttgt   360
tgatctcttc acaacggttc aatgagacct ggaagtacgc attcgacaag aaatttcaag   420
aggaggcgaa caggaccagt attccacaat tccacttcct taagcaaaaa caaactgtga   480
actcattctg gtcgaaaata tcttcatttt tgtcactttc aaactccact gcagacacat   540
ttcatcttcg aaacggtgat gtatccgtag aaatctttgc tgaaccttttt caattgaaag   600 tttactggca aaatgcgctg aaacttattg taaacgagca aaatttcctg aacattgaac   660
atcatagaac taagcaggaa aacttcgcac acgtgctgcc agaagaaaca actttcaaca   720
tgttaaagga caatttcttg tattcaaagc atgactctat gcctttgggg cctgaatcgg   780
ttgcgctaga tttctctttc atgggttcta ctaatgtcta cggtataccg gaacatgcga   840
cgtcgctaag gctgatggac acttcaggtg gaaaggaacc ctacaggctt ttcaacgttg   900
```

```
atgtctttga gtacaacatc ggtaccagcc aaccaatgta cggttcgatc ccattcatgt    960
tttcatcttc gtccacatct atcttttggg tcaatgcagc tgacacttgg gtagacataa   1020
agtatgacac cagtaaaaat aaaacgatga ctcattggat ctccgaaaat ggtgtcatag   1080
atgtagtcat gtccctgggg ccagatattc caactatcat tgacaaattt accgatttga   1140
ctggtagacc cttttaccg cccatttcct ctagggta ccatcaatgt agatggaatt   1200
ataatgatga gatggacgtt ctcacagtgg actctcagat ggatgctcat atgattcctt   1260
acgattttat ttggttggac ttggagtata cgaacgacaa aaaatatttt acttggaagc   1320
agcactcctt tcccaatcca aaaaggctgt tatccaaatt aaaaaagttg ggtagaaatc   1380
ttgtcgtact aatcgatcct catttaaaga aagattatga aatcagtgac agggtaatta   1440
atgaaaatgt agcagtcaag gatcacaatg gaaatgacta tgtaggtcat tgctggccag   1500
gtaattctat atggattgat accataagca aatatggcca aaagatttgg aagtcctttt   1560
tcgaacggtt tatggatctg ccggctgatt taactaattt attcatttgg aatgatatga   1620
acgagccttc gattttcgat ggcccagaga ccacagctcc aaaagatttg attcacgaca   1680
attacattga ggaaagatcc gtccataaca tatatggtct atcagtgcat gaagctactt   1740
acgacgcaat aaaatcgatt tattcaccat ccgataagcg tcctttcctt ctaacaaggg   1800
cttttttgc cggctctcaa cgtactgctg ccacatggac tggtgacaat gtggccaatt   1860
gggattactt aaagatttcc attcctatgg ttctgtcaaa caacattgct ggtatgccat   1920
ttataggagc cgacatagct ggctttgctg aggatcctac acctgaattg attgcacgtt   1980
ggtaccaagc gggcttatgg tacccatttt ttagagcaca cgcccatata gacaccaaga   2040
gaagagaacc atacttattc aatgaacctt gaagtcgat agtacgtgat attatccaat   2100
tgagatattt cctgctacct accttataca ccatgtttca taaatcaagt gtcactggat   2160
ttccgataat gaatccaatg tttattgaac ccctgaattt tgctgaattg tatcatatcg   2220
ataaccaatt ttactggagt aattcaggtc tattagtcaa acctgtcacg gagcctggtc   2280
aatcagaaac ggaaatggtt ttcccacccg gtatattcta tgaattcgca tctttacact   2340
cttttataaa caatggtact gatttgatag aaaagaatat ttctgcacca ttggataaaa   2400
ttccattatt tattgaaggc ggtcacatta tcactatgaa agataagtat agaagatctt   2460
caatgttaat gaaaaacgat ccatatgtaa tagttatagc ccctgatacc gagggacgag   2520
ccgttggaga tctttatgtt gatgatggag aaacttttgg ctaccaaaga ggtgagtacg   2580
tagaaactca gttcattttc gaaaacaata ccttaaaaaa tgttcgaagt catattcccg   2640
agaatttgac aggcattcac cacaatactt tgaggaatac caatattgaa aaaatcatta   2700
tcgcaaagaa taatttacaa cacaacataa cgttgaaaga cagtattaaa gtcaaaaaaa   2760
atggcgaaga aagttcattg ccgactagat cgtcatatga gaatgataat aagatcacca   2820
ttcttaacct atcgcttgac ataactgaag attgggaagt tatttttggg cccgaacaaa   2880
aactcatctc agaagaggat ctgaatagcc ccgtcgacca tcatcatcat catcattgag   2940
ttttagcctt agacatgact gttcctcagt tcaagttggg cacttacgag aagaccggtc   3000
ttgctagatt ctaatcaaga ggatgtcaga atgccatttg cctgagagat gcaggcttca   3060
ttttttgatac ttttttattt gtaacctata tagtatagga ttttttttgt cattttgttt   3120
cttctcgtac gagcttgctc ctgatcagcc tatctcgcag ctgatgaata tcttgtggta   3180
ggggtttggg aaaatcattc gagtttgatg ttttttcttgg tatttcccac tcctcttcag   3240
agtacagaag attaagtgag accttcgttt gtgcggatcc cccacacacc atagcttcaa   3300
```

```
aatgtttcta ctcctttttt actcttccag attttctcgg actccgcgca tcgccgtacc    3360
acttcaaaac acccaagcac agcatactaa attttccctc ttcttcctc tagggtgtcg     3420 ttaattaccc gtactaaagg tttggaaaag aaaaaagaga ccgcctcgtt tcttttcctt    3480
cgtcgaaaaa ggcaataaaa attttatca cgtttctttt tcttgaaatt tttttttta     3540 gttttttct ctttcagtga cctccattga tatttaagtt aataaacggt cttcaatttc     3600
tcaagtttca gtttcatttt tcttgttcta ttacaacttt ttttacttct tgttcattag    3660
aaagaaagca tagcaatcta atctaagggc ggtgttgaca attaatcatc ggcatagtat    3720
atcggcatag tataatacga caaggtgagg aactaaacca tggccaagtt gaccagtgcc    3780
gttccggtgc tcaccgcgcg cgacgtcgcc ggagcggtcg agttctggac cgaccggctc    3840
gggttctccc gggacttcgt ggaggacgac ttcgccggtg tggtccggga cgacgtgacc    3900
ctgttcatca gcgcggtcca ggaccaggtg gtgccggaca caccctggc ctgggtgtgg    3960 gtgcgcggcc tggacgagct gtacgccgag tggtcgagg tcgtgtccac gaacttccgg    4020
gacgcctccg gccggccat gaccgagatc ggcgagcagc cgtgggggcg ggagttcgcc    4080
ctgcgcgacc cggccggcaa ctgcgtgcac ttcgtggccg aggagcagga ctgacacgtc    4140
cgacggcggc ccacgggtcc caggcctcgg agatccgtcc ccttttcct tgtcgatat     4200 catgtaatta gttatgtcac gcttacattc acgccctccc cccacatccg ctctaaccga   4260
aaaggaagga gttagacaac ctgaagtcta ggtccctatt tatttttta tagttatgtt    4320 agtattaaga acgttattta tatttcaaat ttttcttttt tttctgtaca gacgcgtgta    4380
cgcatgtaac attatactga aaaccttgct tgagaaggtt ttgggacgct cgaaggcttt    4440
aatttgcaag ctggagacca acatgtgagc aaaaggccag caaaaggcca ggaaccgtaa    4500
aaaggccgcg ttgctggcgt ttttccatag gctccgcccc cctgacgagc atcacaaaaa    4560
tcgacgctca agtcagaggt ggcgaaaccc gacaggacta taaagatacc aggcgtttcc    4620
ccctggaagc tccctcgtgc gctctcctgt tccgaccctg ccgcttaccg gatacctgtc    4680
cgcctttctc ccttcgggaa gcgtggcgct ttctcaatgc tcacgctgta ggtatctcag    4740
ttcggtgtag gtcgttcgct ccaagctggg ctgtgtgcac gaaccccccg ttcagcccga    4800
ccgctgcgcc ttatccggta actatcgtct tgagtccaac ccggtaagac acgacttatc    4860
gccactggca gcagccactg gtaacaggat tagcagagcg aggtatgtag gcggtgctac    4920
agagttcttg aagtggtggc ctaactacgg ctacactaga aggacagtat ttggtatctg    4980
cgctctgctg aagccagtta ccttcggaaa aagagttggt agctcttgat ccggcaaaca    5040
aaccaccgct ggtagcggtg ttttttttgt ttgcaagcag cagattacgc gcagaaaaaa    5100
aggatctcaa gaagatcctt tgatcttttc tacgggtct gacgctcagt ggaacgaaaa     5160
ctcacgttaa gggattttgg tcatgcatga gatcagatct ttttttgtaga aatgtcttgg   5220 tgtcctcgtc caatcaggta gccatctctg aaatatctgg ctccgttgca actccgaacg    5280
acctgctggc aacgtaaaat ctccgggggt aaaacttaaa tgtggagtaa tggaaccaga    5340
aacgtctctt cccttctctc tccttccacc gcccgttacc gtccctagga aatttactc     5400 tgctggagag cttcttctac ggccccttg cagcaatgct cttcccagca ttacgttgcg     5460
ggtaaaacgg aggtcgtgta cccgacctag cagcccaggg atgaaaaagt cccggccgtc    5520
gctggcaata atagcggggcg gacgcatgtc atgagattat tggaaaccac cagaatcgaa    5580
tataaaaggc gaacaccttt cccaattttg gtttctcctg acccaaagac tttaaattta    5640 atttattttgt ccctatttca atcaattgaa caactatttc gaaacgagga attcacgtgg    5700
```

-continued

| | |
|---|---|
| cccagccggc cgtctcggat cggtacc | 5727 |

<210> SEQ ID NO 19
<211> LENGTH: 7236
<212> TYPE: DNA
<213> ORGANISM: Artificial Sequence
<220> FEATURE:
<223> OTHER INFORMATION: Description of Artificial Sequence:Sequence of plasmid pGAPADE1glsII.

<400> SEQUENCE: 19

| | |
|---|---|
| tcgaccggct gcattaatga atcggccaac gcgcggggag aggcggtttg cgtattgggc | 60 |
| gctcttccgc ttcctcgctc actgactcgc tgcgctcggt cgttcggctg cggcgagcgg | 120 |
| tatcagctca ctcaaaggcg gtaatacggt tatccacaga atcaggggat aacgcaggaa | 180 |
| agaacatgtg agcaaaaggc cagcaaaagg ccaggaaccg taaaaaggcc gcgttgctgg | 240 |
| cgttttccca taggctccgc cccctgacg agcatcacaa aaatcgacgc tcaagtcaga | 300 |
| ggtggcgaaa cccgacagga ctataaagat accaggcgtt tcccctgga agctccctcg | 360 |
| tgcgctctcc tgttccgacc ctgccgctta ccggatacct gtccgccttt ctcccttcgg | 420 |
| gaagcgtggc gctttctcat agctcacgct gtaggtatct cagttcggtg taggtcgttc | 480 |
| gctccaagct gggctgtgtg cacgaacccc cgttcagcc cgaccgctgc gccttatccg | 540 |
| gtaactatcg tcttgagtcc aacccggtaa gacacgactt atcgccactg gcagcagcca | 600 |
| ctggtaacag gattagcaga gcgaggtatg taggcggtgc tacagagttc ttgaagtggt | 660 |
| ggcctaacta cggctacact agaaggacag tatttggtat ctgcgctctg ctgaagccag | 720 |
| ttaccttcgg aaaaagagtt ggtagctctt gatccggcaa acaaaccacc gctggtagcg | 780 |
| gtggtttttt tgtttgcaag cagcagatta cgcgcagaaa aaaaggatct caagaagatc | 840 |
| ctttgatctt ttctacgggg tctgacgctc agtggaacga aaactcacgt taagggattt | 900 |
| tggtcatgag attatcaaaa aggatcttca cctagatcct tttaaattaa aaatgaagtt | 960 |
| ttaaatcaat ctaaagtata tatgagtaaa cttggtctga cagttaccaa tgcttaatca | 1020 |
| gtgaggcacc tatctcagcg atctgtctat ttcgttcatc catagttgcc tgactccccg | 1080 |
| tcgtgtagat aactacgata cgggagggct taccatctgg ccccagtgct gcaatgatac | 1140 |
| cgcgagaccc acgctcaccg gctccagatt tatcagcaat aaaccagcca gccggaaggg | 1200 |
| ccgagcgcag aagtggtcct gcaactttat ccgcctccat ccagtctatt aattgttgcc | 1260 |
| gggaagctag agtaagtagt tcgccagtta atagtttgcg caacgttgtt gccattgcta | 1320 |
| caggcatcgt ggtgtcacgc tcgtcgtttg gtatggcttc attcagctcc ggttcccaac | 1380 |
| gatcaaggcg agttacatga tcccccatgt tgtgcaaaaa agcggttagc tccttcggtc | 1440 |
| ctccgatcgt tgtcagaagt aagttggccg cagtgttatc actcatggtt atggcagcac | 1500 |
| tgcataattc tcttactgtc atgccatccg taagatgctt ttctgtgact ggtgagtact | 1560 |
| caaccaagtc attctgagaa tagtgtatgc ggcgaccgag ttgctcttgc ccggcgtcaa | 1620 |
| tacgggataa taccgcgcca catagcagaa ctttaaaagt gctcatcatt ggaaaacgtt | 1680 |
| cttcggggcg aaaactctca aggatcttac cgctgttgag atccagttcg atgtaaccca | 1740 |
| ctcgtgcacc caactgatct tcagcatctt ttactttcac cagcgtttct gggtgagcaa | 1800 |
| aaacaggaag gcaaaatgcc gcaaaaaagg gaataagggc gacacggaaa tgttgaatac | 1860 |
| tcatactctt cctttttcaa tagctccaag gcaacaaatt gactactcag accgacattc | 1920 |
| attcgttatt gattttaaat caacgataaa cggaatggtt acttgaatga tttcacttta | 1980 |

```
tgatcattgt ttactaatta cctaaatagg attttatatg gaattggaag aataagggaa    2040
atttcagatg tctgaaaaag gcgaggaggg tactaatcat tcaagcccat tcttgccag     2100 taattgcttc ataagcttca atatactttt ctttactctt gatagcaatt tctgcatcca    2160
tggctacgcc ctctttgcca ttcaatccgt tggccgtcaa ccaatctctg agaaactgct    2220
tatcgtaact ctcttgcgat ttacccactt ggtaagtctt ttgattccaa aatctagaag   2280
aatctggagt taaaacttca tctactagta ccaattcatt gttttcgtcc agtccaaatt    2340
cgaatttcgt atcagcaata atgatcccct tcaaagggc gaagtttttt gcagcagaat    2400
acaactcgac cgccttgaca gcgaccttct cacaaatgtc tttacctaca atctcagcag    2460
cttgttcaat agagatgttt tcatcgtgtt caccctgttc agctttcgtt gaaggtgtga    2520
aaatcggagt tggaaaggcg tcgctctctt gaaggttctc gttttcaacc ttgactccat    2580
ggacagtttt tgagttcttg tactcttttcc atgcacttcc agtgatgtaa cctctgacaa   2640
tggcttccaa aggtatcagt ctgtgctttt ttactatcaa ggatcgtccc tctaattgag    2700
atttgtattt ttcttcagac agttttgatg gtagtaaagc aaagacttcc ttgtcattag    2760
aagcaaccaa atgattcttt atgtagggtg ccaaaaaatc aaaccagaaa actgagagct    2820
gagtcaaaat cttcccctta tcaggaatac cgtttgtcat aatcacatcg taagcggaga    2880
tacggtcagt tgcgacgaac agcaagttgt tctcatcgac tgcataaatg tctctaacct    2940
ttcctttggc gattaaaggt aggattccgt ccagatcagt gttcacaatg acatacttg     3000 gaaggataca gcaaagtgtg ttggaagcga tgacacatgg aaaggaattt ttcgagtttc    3060
ctagagtagt atattggggc ggtgaaagtt cagatgttta atgcttaata ctcttatact    3120
cttcaaagcg cccaagtgtt tctgccaacc tgactttttt ctgaataatg aatcgttcaa    3180
gtggagtatt taaaccatga ttaagttacg tgatttggca ctggataagg tcgaaaaata    3240
tccgtattca taaacgatta ttggtaaaag ttacaaaata ccactaatta cggagaagct    3300
tagtaacagt tatcatctct tggtcgatta acgcttacaa tttccattcg ccattcaggc    3360
tgcgcaactg ttgggaaggg cgatcggtgc gggcctcttc gctattacgc cagggcctcg    3420
aggcacaaac gaacgtctca cttaatcttc tgtactctga agaggagtgg gaaataccaa    3480
gaaaaacatc aaactcgaat gattttccca acccctacc acaagatatt catcagctgc     3540
gagataggct gatcaggagc aagctcgtac gagaagaaac aaaatgacaa aaaaaatcct   3600
atactatata ggttacaaat aaaaaagtat caaaaatgaa gcctgcatct ctcaggcaaa    3660
tggcattctg acatcctctt gattagaatc tagcaagacc ggtcttctcg taagtgccca    3720
acttgaactg aggaacagtc atgtctaagg ctaaaactca atgatgatga tgatgatggt    3780
cgacggcgct attcagatcc tcttctgaga tgagttttg ttcgggccca aaaataactt     3840
cccaatcttc agttatgtca agcgataggt taagaatggt gatcttatta tcattctcat    3900
atgacgatct agtcggcaat gaactttctt cgccattttt tttgacttta atactgtctt    3960
tcaacgttat gttgtgttgt aaattattct ttgcgataat gattttttca atattggtat    4020
tcctcaaagt attgtggtga atgcctgtca aattctcggg aatatgactt cgaacatttt    4080
ttaaggtatt gttttcgaaa atgaactgag tttctacgta ctcacctctt tggtagccaa    4140
aagtttctcc atcatcaaca taaagatctc caacggctcg tccctcggta tcaggggcta    4200
taactattac atatggatcg ttttttcatta acattgaaga tcttctatac ttatctttca   4260
tagtgataat gtgaccgcct tcaataaata atggaatttt atccaatggt gcagaaatat    4320
tcttttctat caaatcagta ccattgttta taaaagagtg taaagatgcg aattcataga    4380
```

```
atataccggg tgggaaaacc atttccgttt ctgattgacc aggctccgtg acaggtttga    4440
ctaatagacc tgaattactc cagtaaaatt ggttatcgat atgatacaat tcagcaaatt    4500
cagggtgttc aataaacatt ggattcatta tcggaaatcc agtgacactt gatttatgaa    4560
acatggtgta taaggtaggt agcaggaaat atctcaattg gataatatca cgtactatcg    4620
acttcaaagg ttcattgaat aagtatggtt ctcttctctt ggtgtctata tgggcgtgtg    4680
ctctaaaaaa tgggtaccat aagcccgctt ggtaccaacg tgcaatcaat tcaggtgtag    4740
gatcctcagc aaagccagct atgtcggctc ctataaatgg cataccagca atgttgtttg    4800
acagaaccat aggaatggaa atctttaagt aatcccaatt ggccacattg tcaccagtcc    4860
atgtggcagc agtacgttga gagccggcaa aaaaagccct tgttagaagg aaaggacgct    4920
tatcggatgg tgaataaatc gattttattg cgtcgtaagt agcttcatgc actgatagac    4980
catatatgtt atggacggat cttttcctcaa tgtaattgtc gtgaatcaaa tcttttggag    5040
ctgtggtctc tgggccatcg aaaatcgaag gctcgttcat atcattccaa atgaataaat    5100
tagttaaatc agccggcaga tccataaacc gttcgaaaaa ggacttccaa atcttttggc    5160
catatttgct tatggtatca atccatatag aattacctgg ccagcaatga cctacatagt    5220
catttccatt gtgatccttg actgctacat tttcattaat taccctgtca ctgatttcat    5280
aatctttctt taaatgagga tcgattagta cgacaagatt tctacccaac ttttttaatt    5340
tggataacag cctttttgga ttgggaaagg agtgctgctt ccaagtaaaa tatttttgt    5400 cgttcgtata ctccaagtcc aaccaaataa aatcgtaagg aatcatatga gcatccatct    5460
gagagtccac tgtgagaacg tccatctcat cattataatt ccatctacat tgatggtacc    5520
ctatagagga atgggcggt aaaaagggtc taccagtcaa atcggtaaat tgtcaatga    5580 tagttggaat atctggcccc agggacatga ctacatctat gacaccattt tcggagatcc    5640
aatgagtcat cgtttatttt ttactggtgt catactttat gtctacccaa gtgtcagctg    5700
cattgaccca aaagatagat gtggacgaag atgaaaacat gaatgggatc gaaccgtaca    5760
ttggttggct ggtaccgatg ttgtactcaa agacatcaac gttgaaaagc ctgtagggtt    5820
cctttccacc tgaagtgtcc atcagcctta gcgacgtcgc atgttccggt ataccgtaga    5880
cattagtaga acccatgaaa gagaaatcta gcgcaaccga ttcaggcccc aaaggcatag    5940
agtcatgctt tgaatacaag aaattgtcct taaacatgtt gaaagttgtt tcttctggca    6000
gcacgtgtgc gaagttttcc tgcttagttc tatgatgttc aatgttcagg aaattttgct    6060
cgtttacaat aagtttcagc gcattttgcc agtaaacttt caattgaaaa ggttcagcaa    6120
agatttctac ggatacatca ccgtttcgaa gatgaaatgt gtctgcagtg gagtttgaaa    6180
gtgacaaaaa tgaagatatt ttcgaccaga atgagttcac agtttgtttt tgcttaagga    6240
agtggaattg tggaatactg gtcctgttcg cctcctcttg aaatttcttg tcgaatgcgt    6300
acttccaggt ctcattgaac cgttgtgaag agatcaacaa accgctgctg ttggttggca    6360
ttctctcttt ctcatttata gtgaacctta ctgagtgatc ctgtaaaaaa gagagagaga    6420 atgggaactag aacggctata tcatcgccct ccaatcttgg tatagttta attatggtag    6480 catgaagcac attctctaaa ggatcgtgtg caatagactc ggcgtccact tgtaatagc    6540 agtgatgaga tttggcaata ttttctgcat aaaccctgtt tctatggcaa acccagatt    6600 gcgcacactt ctttaataga tagtcggtaa acgcatgcga aaaagcggta agaagacca    6660 attggcatac gagccatttc aaaaggacca tctcgaggta ccgatccgag acggccggct    6720
gggccacgtg aattcctcgt ttcgaaatag ttgttcaatt gattgaaata gggacaaata    6780
```

-continued

| | |
|---|---|
| aattaaattt aaagtctttg ggtcaggaga aaccaaaatt gggaaaggtg ttcgcctttt | 6840 |
| atattcgatt ctggtggttt ccaataatct catgacatgc gtccgcccgc tattattgcc | 6900 |
| agcgacggcc gggacttttc catccctggg ctgctaggtc gggtacacga cctccgtttt | 6960 |
| acccgcaacg taatgctggg aagagcattg ctgcaagggg gccgtagaag aagctctcca | 7020 |
| gcagagtaaa atttcctagg gacggtaacg ggcggtggaa ggagagagaa gggaagagac | 7080 |
| gtttctggtt ccattactcc acatttaagt tttaccccgg agaatttac gttgccagca | 7140 |
| ggtcgttcgg agttgcaacg gagccagata tttcagagat ggctacctga ttggacgagg | 7200 |
| acaccaagac atttctacaa aaaagatctg atctca | 7236 |

<210> SEQ ID NO 20
<211> LENGTH: 6173
<212> TYPE: DNA
<213> ORGANISM: Artificial Sequence
<220> FEATURE:
<223> OTHER INFORMATION: Description of Artificial Sequence:Sequence of plasmid pPICZAGLSII.

<400> SEQUENCE: 20

| | |
|---|---|
| cgaacaaaaa ctcatctcag aagaggatct gaatagcgcc gtcgaccatc atcatcatca | 60 |
| tcattgagtt tgtagcctta gacatgactg ttcctcagtt caagttgggc acttacgaga | 120 |
| agaccggtct tgctagattc taatcaagag gatgtcagaa tgccatttgc ctgagagatg | 180 |
| caggcttcat ttttgatact ttttatttg taacctatat agtataggat ttttttttgtc | 240 |
| attttgtttc ttctcgtacg agcttgctcc tgatcagcct atctcgcagc tgatgaatat | 300 |
| cttgtggtag gggtttggga aaatcattcg agtttgatgt ttttcttggt atttcccact | 360 |
| cctcttcaga gtacagaaga ttaagtgaga ccttcgtttg tgcggatccc ccacacacca | 420 |
| tagcttcaaa atgtttctac tccttttta ctcttccaga ttttctcgga ctccgcgcat | 480 |
| cgccgtacca cttcaaaaca cccaagcaca gcatactaaa ttttccctct tcttcctct | 540 |
| agggtgtcgt taattacccg tactaaaggt ttggaaaaga aaaagagac cgcctcgttt | 600 |
| cttttttcttc gtcgaaaaag gcaataaaaa tttttatcac gtttcttttt cttgaaattt | 660 |
| tttttttttag tttttttctc tttcagtgac ctccattgat atttaagtta ataaacggtc | 720 |
| ttcaatttct caagtttcag tttcatttt cttgttctat tacaacttttt tttacttctt | 780 |
| gttcattaga aagaaagcat agcaatctaa tctaagggc ggtgttgaca attaatcatc | 840 |
| ggcatagtat atcggcatag tataatacga caaggtgagg aactaaacca tggccaagtt | 900 |
| gaccagtgcc gttccggtgc tcaccgcgcg cgacgtcgcc ggagcggtcg agttctggac | 960 |
| cgaccggctc gggttctccc gggacttcgt ggaggacgac ttcgccggtg tggtccggga | 1020 |
| cgacgtgacc ctgttcatca gcgcggtcca ggaccaggtg gtgccggaca cacccctggc | 1080 |
| ctgggtgtgg gtgcgcggcc tggacgagct gtacgccgag tggtcggagg tcgtgtccac | 1140 |
| gaacttccgg gacgcctccg ggcggccat gaccgagatc ggcgagcagc cgtggggcg | 1200 |
| ggagttcgcc ctgcgcgacc cggccggcaa ctgcgtgcac ttcgtggccg aggagcagga | 1260 |
| ctgacacgtc cgacggcggc ccacgggtcc caggcctcgg agatccgtcc ccttttcct | 1320 |
| ttgtcgatat catgtaatta gttatgtcac gcttacattc acgccctccc cccacatccg | 1380 |
| ctctaaccga aaaggaagga gttagacaac ctgaagtcta ggtccctatt tatttttta | 1440 |
| tagttatgtt agtattaaga acgttattta tatttcaaat ttttcttttt tttctgtaca | 1500 |
| gacgcgtgta cgcatgtaac attatactga aaaccttgct tgagaaggtt ttgggacgct | 1560 |
| cgaaggcttt aatttgcaag ctggagacca acatgtgagc aaaaggccag caaaaggcca | 1620 |

```
ggaaccgtaa aaaggccgcg ttgctggcgt ttttccatag gctccgcccc cctgacgagc    1680
atcacaaaaa tcgacgctca agtcagaggt ggcgaaaccc gacaggacta taaagatacc    1740
aggcgtttcc ccctggaagc tccctcgtgc gctctcctgt tccgaccctg ccgcttaccg    1800
gatacctgtc cgcctttctc ccttcgggaa gcgtggcgct ttctcaatgc tcacgctgta    1860
ggtatctcag ttcggtgtag gtcgttcgct ccaagctggg ctgtgtgcac gaaccccccg    1920
ttcagcccga ccgctgcgcc ttatccggta actatcgtct tgagtccaac ccggtaagac    1980
acgacttatc gccactggca gcagccactg gtaacaggat tagcagagcg aggtatgtag    2040
gcggtgctac agagttcttg aagtggtggc ctaactacgg ctacactaga aggacagtat    2100
ttggtatctg cgctctgctg aagccagtta ccttcggaaa aagagttggt agctcttgat    2160
ccggcaaaca aaccaccgct ggtagcggtg gtttttttgt ttgcaagcag cagattacgc    2220
gcagaaaaaa aggatctcaa gaagatcctt tgatcttttc tacggggtct gacgctcagt    2280
ggaacgaaaa ctcacgttaa gggattttgg tcatgagatc agatctaaca tccaaagacg    2340
aaaggttgaa tgaaaccttt ttgccatccg acatccacag gtccattctc acacataagt    2400
gccaaacgca acaggagggg atacactagc agcagaccgt tgcaaacgca ggacctccac    2460
tcctcttctc ctcaacaccc acttttgcca tcgaaaaacc agcccagtta ttgggcttga    2520
ttggagctcg ctcattccaa ttccttctat taggctacta acaccatgac tttattagcc    2580
tgtctatcct ggcccccctg gcgaggttca tgtttgttta tttccgaatg caacaagctc    2640
cgcattacac ccgaacatca ctccagatga gggctttctg agtgtggggt caaatagttt    2700
catgttcccc aaatggccca aaactgacag tttaaacgct gtcttggaac ctaatatgac    2760
aaaagcgtga tctcatccaa gatgaactaa gtttggttcg ttgaaatgct aacggccagt    2820
tggtcaaaaa gaaacttcca aaagtcggca taccgtttgt cttgtttggt attgattgac    2880
gaatgctcaa aaataatctc attaatgctt agcgcagtct ctctatcgct tctgaacccc    2940
ggtgcacctg tgccgaaacg caaatgggga acacccgct ttttggatga ttatgcattg     3000
tctccacatt gtatgcttcc aagattctgg tgggaatact gctgatagcc taacgttcat    3060
gatcaaaatt taactgttct aacccctact tgacagcaat atataaacag aaggaagctg    3120
ccctgtctta aaccttttt tttatcatca ttattagctt actttcataa ttgcgactgg     3180
ttccaattga caagcttttg atttttaacga cttttaacga caacttgaga agatcaaaaa    3240
acaactaatt attcgaaacg aggaattcac gtggcccagc cggccgtctc ggatcggtac    3300
ctcgagatgg tccttttgaa atggctcgta tgccaattgg tcttctttac cgcttttttcg   3360 catgcgttta ccgactatct attaaagaag tgtgcgcaat ctgggttttg ccatagaaac    3420
agggtttatg cagaaaatat tgccaaatct catcactgct attacaaagt ggacgccgag    3480
tctattgcac acgatccttt agagaatgtg cttcatgcta ccataattaa aactatacca    3540
agattggagg gcgatgatat agccgttcag ttcccattct ctctctcttt tttacaggat    3600
cactcagtaa ggttcactat aaatgagaaa gagagaatgc caaccaacag cagcggtttg    3660
ttgatctctt cacaacggtt caatgagacc tggaagtacg cattcgacaa gaaatttcaa    3720
gaggaggcga acaggaccag tattccacaa ttccacttcc ttaagcaaaa acaaactgtg    3780
aactcattct ggtcgaaaat atcttcattt ttgtcacttt caaactccac tgcagacaca    3840
tttcatcttc gaaacggtga tgtatccgta gaaatctttg ctgaaccttt tcaattgaaa    3900
gtttactggc aaaatgcgct gaaacttatt gtaaacgagc aaaatttcct gaacattgaa    3960
catcatagaa ctaagcagga aaacttcgca cacgtgctgc cagaagaaac aactttcaac    4020
```

```
atgtttaagg caatttcttt gtattcaaag catgactcta tgcctttggg gcctgaatcg    4080
gttgcgctag atttctcttt catgggttct actaatgtct acggtatacc ggaacatgcg    4140
acgtcgctaa ggctgatgga cacttcaggt ggaaaggaac cctacaggct tttcaacgtt    4200
gatgtctttg agtacaacat cggtaccagc caaccaatgt acggttcgat cccattcatg    4260
ttttcatctt cgtccacatc tatcttttgg gtcaatgcag ctgacacttg gtagacata    4320 aagtatgaca ccagtaaaaa taaaacgatg actcattgga tctccgaaaa tggtgtcata    4380
gatgtagtca tgtccctggg gccagatatt ccaactatca ttgacaaatt taccgatttg    4440
actggtagac ccttttacc gcccatttcc tctataggt accatcaatg tagatggaat    4500
tataatgatg agatggacgt tctcacagtg gactctcaga tggatgctca tatgattcct    4560
tacgatttta tttggttgga cttggagtat acgaacgaca aaaatatttt tacttggaag    4620
cagcactcct ttcccaatcc aaaaaggctg ttatccaaat taaaaagtt gggtagaaat    4680 cttgtcgtac taatcgatcc tcatttaaag aaagattatg aaatcagtga cagggtaatt    4740
aatgaaaatg tagcagtcaa ggatcacaat ggaaatgact atgtaggtca ttgctggcca    4800
ggtaattcta tatggattga taccataagc aaatatggcc aaaagatttg gaagtccttt    4860
ttcgaacggt ttatggatct gccggctgat ttaactaatt tattcatttg gaatgatatg    4920
aacgagcctt cgatttttcga tggcccagag accacagctc caaagattt gattcacgac    4980 aattacattg aggaaagatc cgtccataac atatatggtc tatcagtgca tgaagctact    5040
tacgacgcaa taaatcgat ttattcacca tccgataagc gtccttcct tctaacaagg    5100 gctttttttg ccggctctca acgtactgct gccacatgga ctggtgacaa tgtggccaat    5160
tgggattact taaagatttc cattcctatg gttctgtcaa acaacattgc tggtatgcca    5220
tttataggag ccgacatagc tggctttgct gaggatccta cacctgaatt gattgcacgt    5280
tggtaccaag cgggcttatg gtacccattt tttagagcac acgcccatat agacaccaag    5340
agaagagaac catacttatt caatgaacct ttgaagtcga tagtacgtga tattatccaa    5400
ttgagatatt tcctgctacc taccttatac accatgtttc ataaatcaag tgtcactgga    5460
tttccgataa tgaatccaat gtttattgaa caccctgaat ttgctgaatt gtatcatatc    5520
gataaccaat tttactggag taattcaggt ctattagtca aacctgtcac ggagcctggt    5580
caatcagaaa cggaaatggt tttcccaccc ggtatattct atgaattcgc atctttacac    5640
tcttttataa acaatggtac tgatttgata gaaaagaata tttctgcacc attggataaa    5700
attccattat ttattgaagg cggtcacatt atcactatga agataagta tagaagatct    5760 tcaatgttaa tgaaaaacga tccatatgta atagttatag cccctgatac cgagggacga    5820
gccgttggag atctttatgt tgatgatgga gaaacttttg gctaccaaag aggtgagtac    5880
gtagaaactc agttcatttt cgaaaacaat accttaaaaa atgttcgaag tcatattccc    5940
gagaatttga caggcattca ccacaatact ttgaggaata ccaatattga aaaaatcatt    6000
atcgcaaaga ataatttaca acacaacata acgttgaaag acagtattaa agtcaaaaaa    6060
aatggcgaag aaagttcatt gccgactaga tcgtcatatg agaatgataa taagatcacc    6120
attcttaacc tatcgcttga cataactgaa gattgggaag ttattttggg gcc          6173
```

<210> SEQ ID NO 21
<211> LENGTH: 7639
<212> TYPE: DNA
<213> ORGANISM: Artificial Sequence
<220> FEATURE:
<223> OTHER INFORMATION: Description of Artificial Sequence:Sequence of plasmid pPICADE1glsII.

<400> SEQUENCE: 21

```
aaattcctcg tttcgaataa ttagttgttt tttgatcttc tcaagttgtc gttaaaagtc      60
gttaaaatca aaagcttgtc aattggaacc agtcgcaatt atgaaagtaa gctaataatg     120
atgataaaaa aaaaggttta agacagggca gcttccttct gtttatatat tgctgtcaag     180
taggggttag aacagttaaa ttttgatcat gaacgttagg ctatcagcag tattcccacc     240
agaatcttgg aagcatacaa tgtggagaca atgcataatc atccaaaaag cgggtgtttc     300
cccatttgcg tttcggcaca ggtgcaccgg ggttcagaag cgatagagag actgcgctaa     360
gcattaatga gattattttt gagcattcgt caatcaatac caaacaagac aaacggtatg     420
ccgactttg gaagtttctt tttgaccaac tggccgttag catttcaacg aaccaaactt      480
agttcatctt ggatgagatc acgcttttgt catattaggt tccaagacag cgtttaaact     540
gtcagttttg ggccatttgg ggaacatgaa actatttgac cccacactca gaaagccctc     600
atctggagtg atgttcgggt gtaatgcgga gcttgttgca ttcggaaata aacaaacatg     660
aacctcgcca gggggggccag gatagacagg ctaataaagt catggtgtta gtagcctaat    720
agaaggaatt ggaatgagcg agctccaatc aagcccaata actgggctgg ttttcgatg      780
gcaaaagtgg gtgttgagga gaagaggagt ggaggtcctg cgtttgcaac ggtctgctgc     840
tagtgtatcc cctcctgttg cgtttggcac ttatgtgtga gaatggacct gtggatgtcg     900
gatggcaaaa aggtttcatt caacctttcg tctttggatg ttgtcgaccg gctgcattaa     960
tgaatcggcc aacgcgcggg gagaggcggt ttgcgtattg ggcgctcttc cgcttcctcg    1020
ctcactgact cgctgcgctc ggtcgttcgg ctgcggcgag cggtatcagc tcactcaaag    1080
gcggtaatac ggttatccac agaatcaggg gataacgcag gaaagaacat gtgagcaaaa    1140
ggccagcaaa aggccaggaa ccgtaaaaag gccgcgttgc tggcgttttt ccataggctc    1200
cgccccctg acgagcatca aaaaatcga cgctcaagtc agaggtggcg aaacccgaca      1260
ggactataaa gataccaggc gtttccccct ggaagctccc tcgtgcgctc tcctgttccg    1320
accctgccgc ttaccggata cctgtccgcc tttctccctt cgggaagcgt ggcgctttct    1380
catagctcac gctgtaggta tctcagttcg gtgtaggtcg ttcgctccaa gctgggctgt    1440
gtgcacgaac ccccgttca gcccgaccgc tgcgccttat ccggtaacta tcgtcttgag    1500
tccaacccgg taagacacga cttatcgcca ctggcagcag ccactggtaa caggattagc    1560
agagcgaggt atgtaggcgg tgctacagag ttcttgaagt ggtggcctaa ctacggctac    1620
actagaagga cagtatttgg tatctgcgct ctgctgaagc cagttacctt cggaaaaaga    1680
gttggtagct cttgatccgg caaacaaacc accgctggta gcggtggttt ttttgtttgc    1740
aagcagcaga ttacgcgcag aaaaaaagga tctcaagaag atcctttgat cttttctacg    1800
gggtctgacg ctcagtggaa cgaaaactca cgttaaggga ttttggtcat gagattatca    1860
aaaaggatct tcacctagat ccttttaaat taaaaatgaa gttttaaatc aatctaaagt    1920
atatatgagt aaacttggtc tgacagttac caatgcttaa tcagtgaggc acctatctca    1980
gcgatctgtc tatttcgttc atccatagtt gcctgactcc ccgtcgtgta gataactacg    2040
atacgggagg gcttaccatc tggccccagt gctgcaatga taccgcgaga cccacgctca    2100
ccggctccag atttatcagc aataaaccag ccagccggaa gggccgagcg cagaagtggt    2160
cctgcaactt tatccgcctc catccagtct attaattgtt gccgggaagc tagagtaagt    2220
agttcgccag ttaatagttt gcgcaacgtt gttgccattg ctacaggcat cgtggtgtca    2280
```

```
cgctcgtcgt ttggtatggc ttcattcagc tccggttccc aacgatcaag gcgagttaca    2340
tgatccccca tgttgtgcaa aaagcggtt  agctccttcg gtcctccgat cgttgtcaga    2400
agtaagttgg ccgcagtgtt atcactcatg gttatggcag cactgcataa ttctcttact    2460
gtcatgccat ccgtaagatg cttttctgtg actggtgagt actcaaccaa gtcattctga    2520
gaatagtgta tgcggcgacc gagttgctct tgcccggcgt caatacggga taataccgcg    2580
ccacatagca gaactttaaa agtgctcatc attggaaaac gttcttcggg gcgaaaactc    2640
tcaaggatct taccgctgtt gagatccagt tcgatgtaac ccactcgtgc acccaactga    2700
tcttcagcat cttttacttt caccagcgtt tctgggtgag caaaaacagg aaggcaaaat    2760
gccgcaaaaa agggaataag ggcgacacgg aaatgttgaa tactcatact cttccttttt    2820
caatagctcc aaggcaacaa attgactact cagaccgaca ttcattcgtt attgatttta    2880
aatcaacgat aaacggaatg gttacttgaa tgatttcact ttatgatcat tgtttactaa    2940
ttacctaaat aggattttat atggaattgg aagaataagg gaatttcag  atgtctgaaa    3000 aaggcgagga gggtactaat cattcaagcc catttcttgc cagtaattgc ttcataagct    3060
tcaatatact tttctttact cttgatagca atttctgcat ccatggctac gccctctttg    3120
ccattcaatc cgttggccgt caaccaatct ctgagaaact gcttatcgta actctcttgc    3180
gatttaccca cttggtaagt cttttgattc caaaatctag aagaatctgg agttaaaact    3240
tcatctacta gtaccaattc attgttttcg tccagtccaa attcgaattt cgtatcagca    3300
ataatgatcc ccttcaaaag gcgaagttt  tttgcagcag aatacaactc gaccgccttg    3360
acagcgacct tctcacaaat gtctttacct acaatctcag cagcttgttc aatagagatg    3420
ttttcatcgt gttcaccctg ttcagctttc gttgaaggtg tgaaaatcgg agttggaaag    3480
gcgtcgctct cttgaaggtt ctcgttttca accttgactc catggacagt ttttgagttc    3540
ttgtactctt tccatgcact tccagtgatg taacctctga caatggcttc caaaggtatc    3600
agtctgtgct tttttactat caaggatcgt ccctctaatt gagatttgta tttttcttca    3660
gacagttttg atggtagtaa agcaaagact tccttgtcat tagaagcaac caaatgattc    3720
tttatgtagg gtgccaaaaa atcaaaccag aaaactgaga gctgagtcaa atctttccc     3780 ttatcaggaa taccgtttgt cataatcaca tcgtaagcgg agatacggtc agttgcgacg    3840
aacagcaagt tgttctcatc gactgcataa atgtctctaa cctttccttt ggcgattaaa    3900
ggtaggattc cgtccagatc agtgttcaca atggacatac ttggaaggat acagcaaagt    3960
gtgttggaag cgatgacaca tggaaaggaa ttttcgagt  ttcctagagt agtatattgg    4020
ggcggtgaaa gttcagatgt ttaatgctta atactcttat actcttcaaa gcgcccaagt    4080
gtttctgcca acctgacttt tttctgaata atgaatcgtt caagtggagt atttaaacca    4140
tgattaagtt acgtgatttg gcactggata aggtcgaaaa atatccgtat tcataaacga    4200
ttattggtaa aagttacaaa ataccactaa ttacggagaa gcttagtaac agttatcatc    4260
tcttggtcga ttaacgctta caatttccat tcgccattca ggctgcgcaa ctgttgggaa    4320
gggcgatcgg tgcgggcctc ttcgctatta cgccagggcc tcgagcaca  acgaacgtc     4380 tcacttaatc ttctgtactc tgaagaggag tgggaaatac caagaaaaac atcaaactcg    4440
aatgattttc ccaaaccccct accacaagat attcatcagc tgcgagatag gctgatcagg    4500
agcaagctcg tacgagaaga aacaaaatga caaaaaaaat cctatactat ataggttaca    4560
aataaaaaag tatcaaaaat gaagcctgca tctctcaggc aaatggcatt ctgacatcct    4620
cttgattaga atctagcaag accggtcttc tcgtaagtgc ccaacttgaa ctgaggaaca    4680
```

```
gtcatgtcta aggctacaaa ctcaatgatg atgatgatga tggtcgacgg cgctattcag   4740
atcctcttct gagatgagtt tttgttcggg cccaaaaata acttcccaat cttcagttat   4800
gtcaagcgat aggttaagaa tggtgatctt attatcattc tcatatgacg atctagtcgg   4860
caatgaactt tcttcgccat ttttttttgac tttaatactg tctttcaacg ttatgttgtg   4920
ttgtaaatta ttcttttgcga taatgatttt ttcaatattg gtattcctca aagtattgtg   4980
gtgaatgcct gtcaaattct cgggaatatg acttcgaaca ttttttaagg tattgttttc   5040
gaaaatgaac tgagtttcta cgtactcacc tctttggtag ccaaaagttt ctccatcatc   5100
aacataaaga tctccaacgg ctcgtccctc ggtatcaggg gctataacta ttacatatgg   5160
atcgtttttc attaacattg aagatcttct atacttatct ttcatagtga taatgtgacc   5220
gccttcaata aataatggaa ttttatccaa tggtgcagaa atattctttt ctatcaaatc   5280
agtaccattg tttataaaag agtgtaaaga tgcgaattca tagaatatac cgggtgggaa   5340
aaccatttcc gtttctgatt gaccaggctc cgtgacaggt tgactaata gacctgaatt   5400
actccagtaa aattggttat cgatatgata caattcagca aattcagggt gttcaataaa   5460
cattggattc attatcggaa atccagtgac acttgattta tgaaacatgg tgtataaggt   5520
aggtagcagg aaatatctca attggataat atcacgtact atcgacttca aaggttcatt   5580
gaataagtat ggttctcttc tcttggtgtc tatatgggcg tgtgctctaa aaaatgggta   5640
ccataagccc gcttggtacc aacgtgcaat caattcaggt gtaggatcct cagcaaagcc   5700
agctatgtcg gctcctataa atggcatacc agcaatgttg tttgacagaa ccataggaat   5760
ggaaatcttt aagtaatccc aattggccac attgtcacca gtccatgtgg cagcagtacg   5820
ttgagagccg gcaaaaaaag ccccttgttag aaggaaagga cgcttatcgg atggtgaata   5880
aatcgatttt attgcgtcgt aagtagcttc atgcactgat agaccatata tgttatggac   5940
ggatctttcc tcaatgtaat tgtcgtgaat caaatcttttt ggagctgtgg tctctgggcc   6000
atcgaaaatc gaaggctcgt tcatatcatt ccaaatgaat aaattagtta aatcagccgg   6060
cagatccata aaccgttcga aaaggacttt ccaaatcttt tggccatatt tgcttatggt   6120
atcaatccat atagaattac ctggccagca atgacctaca tagtcatttc cattgtgatc   6180
cttgactgct acatttttcat taattacccct gtcactgatt tcataatctt tctttaaatg   6240
aggatcgatt agtacgacaa gatttctacc caacttttttt aatttggata acagcctttt   6300
tggattggga aaggagtgct gcttccaagt aaaatatttt ttgtcgttcg tatactccaa   6360
gtccaaccaa ataaaatcgt aaggaatcat atgagcatcc atctgagagt ccactgtgag   6420
aacgtccatc tcatcattat aattccatct acattgatgg taccctatag aggaaatggg   6480
cggtaaaaag ggtctaccag tcaaatcggt aaatttgtca atgatagttg gaatatctgg   6540
ccccagggac atgactacat ctatgacacc attttcggag atccaatgag tcatcgtttt   6600
attttttactg gtgtcatact ttatgtctac ccaagtgtca gctgcattga cccaaaagat   6660
agatgtggac gaagatgaaa acatgaatgg gatcgaaccg tacattggtt ggctggtacc   6720
gatgttgtac tcaaagacat caacgttgaa aagcctgtag ggttcctttc cacctgaagt   6780
gtccatcagc cttagcgacg tcgcatgttc cggtataccg tagacattag tagaacccat   6840
gaaagagaaa tctagcgcaa ccgattcagg ccccaaaggc atagagtcat gctttgaata   6900
caagaaattg tccttaaaca tgttgaaagt tgtttcttct ggcagcacgt gtgcgaagtt   6960
ttcctgctta gttctatgat gttcaatgtt caggaaattt tgctcgttta caataagttt   7020
cagcgcattt tgccagtaaa cttctcaattg aaaaggttca gcaaagattt ctacggatac   7080
```

| | |
|---|---|
| atcaccgttt cgaagatgaa atgtgtctgc agtggagttt gaaagtgaca aaaatgaaga | 7140 |
| tattttcgac cagaatgagt tcacagtttg tttttgctta aggaagtgga attgtggaat | 7200 |
| actggtcctg ttcgcctcct cttgaaattt cttgtcgaat gcgtacttcc aggtctcatt | 7260 |
| gaaccgttgt gaagagatca acaaaccgct gctgttggtt ggcattctct ctttctcatt | 7320 |
| tatagtgaac cttactgagt gatcctgtaa aaagagaga gagaatggga actgaacggc | 7380 |
| tatatcatcg ccctccaatc ttggtatagt tttaattatg gtagcatgaa gcacattctc | 7440 |
| taaaggatcg tgtgcaatag actcggcgtc cactttgtaa tagcagtgat gagatttggc | 7500 |
| aatatttttct gcataaaccc tgtttctatg gcaaaaccca gattgcgcac acttctttaa | 7560 |
| tagatagtcg gtaaacgcat gcgaaaaagc ggtaaagaag accaattggc atacgagcca | 7620 |
| tttcaaaagg accatctcg | 7639 |

<210> SEQ ID NO 22
<211> LENGTH: 5742
<212> TYPE: DNA
<213> ORGANISM: Artificial Sequence
<220> FEATURE:
<223> OTHER INFORMATION: Description of Artificial Sequence:Sequence of
      plasmid pYPTIZAGLSII.

<400> SEQUENCE: 22

| | |
|---|---|
| cgaacaaaaa ctcatctcag aagaggatct gaatagcgcc gtcgaccatc atcatcatca | 60 |
| tcattgagtt tgtagcctta gacatgactg ttcctcagtt caagttgggc acttacgaga | 120 |
| agaccggtct tgctagattc taatcaagag gatgtcagaa tgccatttgc ctgagagatg | 180 |
| caggcttcat ttttgatact ttttttatttg taacctatat agtataggat ttttttttgtc | 240 |
| attttgtttc ttctcgtacg agcttgctcc tgatcagcct atctcgcagc tgatgaatat | 300 |
| cttgtggtag gggtttggga aaatcattcg agtttgatgt ttttcttggt atttcccact | 360 |
| cctcttcaga gtacagaaga ttaagtgaga ccttcgtttg tgcggatccc ccacacacca | 420 |
| tagcttcaaa atgtttctac tccttttttta ctcttccaga ttttctcgga ctccgcgcat | 480 |
| cgccgtacca cttcaaaaca cccaagcaca gcatactaaa ttttccctct tcttcctct | 540 |
| agggtgtcgt taattacccg tactaaaggt ttggaaaaga aaaagagac cgcctcgttt | 600 |
| cttttttcttc gtcgaaaaag gcaataaaaa ttttatcac gtttcttttt cttgaaattt | 660 |
| ttttttttag tttttttctc tttcagtgac ctccattgat atttaagtta ataaacggtc | 720 |
| ttcaatttct caagtttcag tttcatttt cttgttctat tacaactttt tttacttctt | 780 |
| gttcattaga aagaaagcat agcaatctaa tctaaggggc ggtgttgaca attaatcatc | 840 |
| ggcatagtat atcggcatag tataatacga caaggtgagg aactaaacca tggccaagtt | 900 |
| gaccagtgcc gttccggtgc tcaccgcgcg cgacgtcgcc ggagcggtcg agttctggac | 960 |
| cgaccggctc gggttctccc gggacttcgt ggaggacgac ttcgccggtg tggtccggga | 1020 |
| cgacgtgacc ctgttcatca gcgcggtcca ggaccaggtg gtgccggaca cacccctggc | 1080 |
| ctgggtgtgg gtgcgcggcc tggacgagct gtacgccgag tggtcggagg tcgtgtccac | 1140 |
| gaacttccgg gacgcctccg ggccggccat gaccgagatc ggcgagcagc cgtggggcg | 1200 |
| ggagttcgcc ctgcgcgacc cggcggcaa ctgcgtgcac ttcgtggccg aggagcagga | 1260 |
| ctgacacgtc cgacggcggc ccacgggtcc caggcctcgg agatccgtcc ccttttcct | 1320 |
| ttgtcgatat catgtaatta gttatgtcac gcttacattc acgccctccc cccacatccg | 1380 |
| ctctaaccga aaaggaagga gttagacaac ctgaagtcta ggtccctatt tatttttta | 1440 |
| tagttatgtt agtattaaga acgttattta tatttcaaat ttttcttttt tttctgtaca | 1500 |

```
gacgcgtgta cgcatgtaac attatactga aaaccttgct tgagaaggtt ttgggacgct   1560
cgaaggcttt aatttgcaag ctggagacca acatgtgagc aaaaggccag caaaaggcca   1620
ggaaccgtaa aaaggccgcg ttgctggcgt ttttccatag gctccgcccc cctgacgagc   1680
atcacaaaaa tcgacgctca agtcagaggt ggcgaaaccc gacaggacta taaagatacc   1740
aggcgtttcc ccctggaagc tccctcgtgc gctctcctgt tccgaccctg ccgcttaccg   1800
gatacctgtc cgcctttctc ccttcgggaa gcgtggcgct ttctcaatgc tcacgctgta   1860
ggtatctcag ttcggtgtag gtcgttcgct ccaagctggg ctgtgtgcac gaaccccccg   1920
ttcagcccga ccgctgcgcc ttatccggta actatcgtct tgagtccaac ccggtaagac   1980
acgacttatc gccactggca gcagccactg gtaacaggat tagcagagcg aggtatgtag   2040
gcggtgctac agagttcttg aagtggtggc ctaactacgg ctacactaga aggacagtat   2100
ttggtatctg cgctctgctg aagccagtta ccttcggaaa aagagttggt agctcttgat   2160
ccggcaaaca aaccaccgct ggtagcggtg gttttttgt ttgcaagcag cagattacgc   2220
gcagaaaaaa aggatctcaa gaagatcctt tgatctttc tacggggtct gacgctcagt   2280
ggaacgaaaa ctcacgttaa gggattttgg tcatgagatc agatctatga tgagtcacaa   2340
tctgcttcca cagacgagta caaggacagg caaaaggaat tggaagaagt tgctaaccca   2400
ataatgagca agttctatgg agctgctggt ggagctcctg gtggagctcc tggtggcttc   2460
cctggaggtt ccctggcgg agctggcgca gctggcggtg ccccaggtgg tgctgcccca   2520
ggcggagaca gcggaccaac cgtggaagaa gtcgattaag caattcaacg ataaattct   2580 ggttaatata tataacgtga ataggaaatt aaggaaattt tggatctaat aatgtgctgt   2640
atgccgacat cgggcatcgt agattgtata gtatcgctga cactataata agccagccaa   2700 aaccctaaa ccagttgccc tccactaatt agtgtactac ccaatcttgc ctcttcgggt   2760 gtctttata aggacagatt cacaagctct tgttgcccaa tacacacata cacacagaga   2820
taatagcagt cgaattcacg tggcccagcc ggccgtctcg gatcggtacc tcgagatggt   2880 cctttttgaaa tggctcgtat gccaattggt cttcttacc gcttttttcgc atgcgtttac   2940 cgactatcta ttaaagaagt gtgcgcaatc tgggttttgc catagaaaca gggtttatgc   3000
agaaaatatt gccaaatctc atcactgcta ttacaaagtg gacgccgagt ctattgcaca   3060
cgatccttta gagaatgtgc ttcatgctac cataattaaa actataccaa gattggaggg   3120
cgatgatata gccgttcagt tcccattctc tctctcttt ttacaggatc actcagtaag   3180
gttcactata aatgagaaag agagaatgcc aaccaacagc agcggtttgt tgatctcttc   3240
acaacggttc aatgagacct ggaagtacgc attcgacaag aaatttcaag aggaggcgaa   3300
caggaccagt attccacaat tccacttcct taagcaaaaa caaactgtga actcattctg   3360
gtcgaaaata tcttcatttt tgtcactttc aaactccact gcagacacat ttcatcttcg   3420
aaacggtgat gtatccgtag aaatctttgc tgaaccttt caattgaaag tttactggca   3480
aaatgcgctg aaacttattg taaacgagca aaatttcctg aacattgaac atcatagaac   3540
taagcaggaa aacttcgcac acgtgctgcc agaagaaaca actttcaaca tgtttaagga   3600
caatttcttg tattcaaagc atgactctat gcctttgggg cctgaatcgg ttgcgctaga   3660 tttctcttc atgggttcta ctaatgtcta cggtataccg gaacatgcga cgtcgctaag   3720
gctgatggac acttcaggtg gaaaggaacc ctacaggctt ttcaacgttg atgtctttga   3780
gtacaacatc ggtaccagcc aaccaatgta cggttcgatc ccattcatgt tttcatcttc   3840
gtccacatct atcttttggg tcaatgcagc tgacacttgg gtagacataa agtatgacac   3900
```

```
cagtaaaaat aaaacgatga ctcattggat ctccgaaaat ggtgtcatag atgtagtcat    3960
gtccctgggg ccagatattc caactatcat tgacaaattt accgatttga ctggtagacc    4020 cttttttaccg cccatttcct ctatagggta ccatcaatgt agatggaatt ataatgatga   4080
gatggacgtt ctcacagtgg actctcagat ggatgctcat atgattcctt acgattttat    4140
ttggttggac ttggagtata cgaacgacaa aaaatatttt acttggaagc agcactcctt    4200
tcccaatcca aaaggctgt tatccaaatt aaaaagttg ggtagaaatc ttgtcgtact       4260
aatcgatcct catttaaaga aagattatga aatcagtgac agggtaatta atgaaaatgt    4320
agcagtcaag gatcacaatg gaaatgacta tgtaggtcat tgctggccag gtaattctat    4380
atggattgat accataagca aatatgccaa aaagatttgg aagtcctttt tcgaacggtt    4440 tatgatctg ccggctgatt taactaattt attcatttgg aatgatatga acgagccttc     4500
gattttcgat ggcccagaga ccacagctcc aaaagatttg attcacgaca attacattga    4560
ggaaagatcc gtccataaca tatatggtct atcagtgcat gaagctactt acgacgcaat    4620
aaaatcgatt tattcaccat ccgataagcg tcctttcctt ctaacaaggg ctttttttgc    4680
cggctctcaa cgtactgctg ccacatggac tggtgacaat gtggccaatt gggattactt    4740
aaagatttcc attcctatgg ttctgtcaaa caacattgct ggtatgccat ttataggagc    4800
cgacatagct ggctttgctg aggatcctac acctgaattg attgcacgtt ggtaccaagc    4860
gggcttatgg tacccatttt ttagagcaca cgcccatata gacaccaaga gaagagaacc   4920
atacttattc aatgaacctt tgaagtcgat agtacgtgat attatccaat tgagatattt    4980
cctgctacct accttataca ccatgtttca taaatcaagt gtcactggat ttccgataat    5040
gaatccaatg tttattgaac accctgaatt tgctgaattg tatcatatcg ataaccaatt    5100
ttactggagt aattcaggtc tattagtcaa acctgtcacg gagcctggtc aatcagaaac   5160
ggaaatggtt ttcccacccg gtatattcta tgaattcgca tctttacact cttttataaa    5220
caatggtact gatttgatag aaaagaatat ttctgcacca ttggataaaa ttccattatt   5280
tattgaaggc ggtcacatta tcactatgaa agataagtat agaagatctt caatgttaat    5340
gaaaaacgat ccatatgtaa tagttatagc ccctgatacc gagggacgag ccgttggaga    5400
tctttatgtt gatgatggag aaacttttgg ctaccaaaga ggtgagtacg tagaaactca   5460
gttcattttc gaaaacaata ccttaaaaaa tgttcgaagt catattcccg agaatttgac    5520
aggcattcac cacaatactt tgaggaatac caatattgaa aaaatcatta tcgcaaagaa   5580
taatttacaa cacaacataa cgttgaaaga cagtattaaa gtcaaaaaaa atggcgaaga  5640
aagttcattg ccgactagat cgtcatatga gaatgataat aagatcacca ttcttaacct    5700
atcgcttgac ataactgaag attgggaagt tattttggg cc                         5742
```

<210> SEQ ID NO 23
<211> LENGTH: 7256
<212> TYPE: DNA
<213> ORGANISM: Artificial Sequence
<220> FEATURE:
<223> OTHER INFORMATION: Description of Artificial Sequence:Sequence of plasmid pYPT1ADE1glsII.

<400> SEQUENCE: 23

```
gtcgaccggc tgcattaatg aatcggccaa cgcgcgggga gaggcggttt gcgtattggg     60
cgctcttccg cttcctcgct cactgactcg ctgcgctcgg tcgttcggct gcggcgagcg    120
gtatcagctc actcaaaggc ggtaatacgg ttatccacag aatcagggga taacgcagga    180
```

```
aagaacatgt gagcaaaagg ccagcaaaag gccaggaacc gtaaaaaggc cgcgttgctg    240 gcgttttttcc ataggctccg ccccccctgac gagcatcaca aaaatcgacg ctcaagtcag    300
aggtggcgaa acccgacagg actataaaga taccaggcgt ttccccctgg aagctccctc    360
gtgcgctctc ctgttccgac cctgccgctt accggatacc tgtccgcctt tctcccttcg    420
ggaagcgtgg cgctttctca tagctcacgc tgtaggtatc tcagttcggt gtaggtcgtt    480
cgctccaagc tgggctgtgt gcacgaaccc cccgttcagc ccgaccgctg cgccttatcc    540
ggtaactatc gtcttgagtc caacccggta agacacgact tatcgccact ggcagcagcc    600
actggtaaca ggattagcag agcgaggtat gtaggcggtg ctacagagtt cttgaagtgg    660
tggcctaact acggctacac tagaaggaca gtatttggta tctgcgctct gctgaagcca    720
gttaccttcg gaaaaagagt tggtagctct tgatccggca acaaaccac cgctggtagc    780 ggtggttttt ttgtttgcaa gcagcagatt acgcgcagaa aaaaggatc tcaagaagat    840 cctttgatct tttctacggg gtctgacgct cagtggaacg aaaactcacg ttaagggatt    900
ttggtcatga gattatcaaa aaggatcttc acctagatcc ttttaaatta aaaatgaagt    960
tttaaatcaa tctaaagtat atatgagtaa acttggtctg acagttacca atgcttaatc   1020
agtgaggcac ctatctcagc gatctgtcta tttcgttcat ccatagttgc ctgactcccc   1080
gtcgtgtaga taactacgat acgggagggc ttaccatctg gccccagtgc tgcaatgata   1140
ccgcgagacc cacgctcacc ggctccagat ttatcagcaa taaaccagcc agccggaagg   1200
gccgagcgca gaagtggtcc tgcaacttta tccgcctcca tccagtctat taattgttgc   1260
cgggaagcta gagtaagtag ttcgccagtt aatagtttgc gcaacgttgt tgccattgct   1320
acaggcatcg tggtgtcacg ctcgtcgttt ggtatggctt cattcagctc cggttcccaa   1380
cgatcaaggc gagttacatg atcccccatg ttgtgcaaaa aagcggttag ctccttcggt   1440
cctccgatcg ttgtcagaag taagttggcc gcagtgttat cactcatggt tatggcagca   1500
ctgcataatt ctcttactgt catgccatcc gtaagatgct tttctgtgac tggtgagtac   1560
tcaaccaagt cattctgaga atagtgtatg cggcgaccga gttgctcttg cccggcgtca   1620
atacgggata taccgcgcc acatagcaga actttaaaag tgctcatcat tggaaaacgt   1680
tcttcggggc gaaaactctc aaggatctta ccgctgttga gatccagttc gatgtaaccc   1740
actcgtgcac ccaactgatc ttcagcatct tttactttca ccagcgtttc tgggtgagca   1800
aaaacaggaa ggcaaaatgc cgcaaaaaag ggaataaggg cgacacggaa atgttgaata   1860
ctcatactct tcctttttca atagctccaa ggcaacaaat tgactactca gaccgacatt   1920
cattcgttat tgattttaaa tcaacgataa acggaatggt tacttgaatg atttcacttt   1980
atgatcattg tttactaatt acctaaatag gattttatat ggaattggaa gaataaggga   2040
aatttcagat gtctgaaaaa ggcgaggagg gtactaatca ttcaagccca tttcttgcca   2100
gtaattgctt cataagcttc aatatacttt tcttttactct tgatagcaat ttctgcatcc   2160
atggctacgc cctctttgcc attcaatccg ttggccgtca accaatctct gagaaactgc   2220
ttatcgtaac tctcttgcga tttacccact tggtaagtct tttgattcca aaatctagaa   2280
gaatctggag ttaaaacttc atctactagt accaattcat tgttttcgtc cagtccaaat   2340
tcgaatttcg tatcagcaat aatgatcccc ttcaaaggg cgaagttttt tgcagcagaa   2400
tacaactcga ccgccttgac agcgaccttc tcacaaatgt ctttacctac aatctcagca   2460
gcttgttcaa tagagatgtt ttcatcgtgt tcaccctgtt cagctttcgt tgaaggtgtg   2520
aaaatcggag ttggaaaggc gtcgctctct tgaaggttct cgttttcaac cttgactcca   2580
```

```
tggacagttt ttgagttctt gtactctttc catgcacttc cagtgatgta acctctgaca    2640
atggcttcca aaggtatcag tctgtgcttt tttactatca aggatcgtcc ctctaattga    2700
gatttgtatt tttcttcaga cagttttgat ggtagtaaag caaagacttc cttgtcatta    2760
gaagcaacca aatgattctt tatgtagggt gccaaaaaat caaaccagaa aactgagagc    2820
tgagtcaaaa tctttccctt atcaggaata ccgtttgtca taatcacatc gtaagcggag    2880
atacggtcag ttgcgacgaa cagcaagttg ttctcatcga ctgcataaat gtctctaacc    2940
tttcctttgg cgattaaagg taggattccg tccagatcag tgttcacaat ggacatactt    3000
ggaaggatac agcaaagtgt gttggaagcg atgacacatg gaaggaatt tttcgagttt     3060 cctagagtag tatattgggg cggtgaaagt tcagatgttt aatgcttaat actcttatac    3120
tcttcaaagc gcccaagtgt ttctgccaac ctgactttt tctgaataat gaatcgttca     3180
agtggagtat ttaaaccatg attaagttac gtgatttggc actggataag gtcgaaaaat    3240
atccgtattc ataaacgatt attggtaaaa gttacaaaat accactaatt acggagaagc    3300
ttagtaacag ttatcatctc ttggtcgatt aacgcttaca atttccattc gccattcagg    3360
ctgcgcaact gttgggaagg gcgatcggtg cgggcctctt cgctattacg ccagggcctc    3420
gaggcacaaa cgaacgtctc acttaatctt ctgtactctg aagaggagtg ggaaatacca    3480
agaaaaacat caaactcgaa tgattttccc aaaccctac cacaagatat tcatcagctg     3540
cgagataggc tgatcaggag caagctcgta cgagaagaaa caaaatgaca aaaaaaatcc    3600
tatactatat aggttacaaa taaaaaagta tcaaaaatga agcctgcatc tctcaggcaa    3660
atggcattct gacatcctct tgattagaat ctagcaagac cggtcttctc gtaagtgccc    3720
aacttgaact gaggaacagt catgtctaag gctacaaact caatgatgat gatgatgatg    3780
gtcgacggcg ctattcagat cctcttctga gatgagtttt tgttcgggcc caaaaataac    3840
ttcccaatct tcagttatgt caagcgatag gttaagaatg gtgatcttat tatcattctc    3900
atatgacgat ctagtcggca atgaactttc ttcgccattt ttttgactt taatactgtc     3960 tttcaacgtt atgttgtgtt gtaaattatt ctttgcgata atgatttttt caatattggt    4020
attcctcaaa gtattgtggt gaatgcctgt caaattctcg ggaatatgac ttcgaacatt    4080
ttttaaggta ttgttttcga aaatgaactg agtttctacg tactcacctc tttggtagcc    4140
aaaagtttct ccatcatcaa cataaagatc tccaacggct cgtccctcgg tatcaggggc    4200
tataactatt acatatggat cgttttcat taacattgaa gatcttctat acttatcttt     4260
catagtgata atgtgaccgc cttcaataaa taatggaatt ttatccaatg gtgcagaaat    4320 attctttct atcaaatcag taccattgtt tataaaagag tgtaaagatg cgaattcata    4380
gaatataccg ggtgggaaaa ccatttccgt ttctgattga ccaggctccg tgacaggttt    4440
gactaataga cctgaattac tccagtaaaa ttggttatcg atatgataca attcagcaaa    4500
ttcagggtgt tcaataaaca ttggattcat tatcggaaat ccagtgacac ttgatttatg    4560
aaacatggtg tataaggtag gtagcaggaa atatctcaat tggataatat cacgtactat    4620
cgacttcaaa ggttcattga ataagtatgg ttctcttctc ttggtgtcta tatgggcgtg    4680
tgctctaaaa aatgggtacc ataagcccgc ttggtaccaa cgtgcaatca attcaggtgt    4740
aggatcctca gcaaagccag ctatgtcggc tcctataaat ggcataccag caatgttgtt    4800
tgacagaacc ataggaatgg aaatctttaa gtaatcccaa ttggccacat tgtcaccagt    4860
ccatgtggca gcagtacgtt gagagccggc aaaaaaagcc cttgttagaa ggaaaggacg    4920
cttatcggat ggtgaataaa tcgattttat tgcgtcgtaa gtagcttcat gcactgatag    4980
```

-continued

```
accatatatg ttatggacgg atctttcctc aatgtaattg tcgtgaatca aatcttttgg    5040
agctgtggtc tctgggccat cgaaaatcga aggctcgttc atatcattcc aaatgaataa    5100
attagttaaa tcagccggca gatccataaa ccgttcgaaa aaggacttcc aaatcttttg    5160
gccatatttg cttatggtat caatccatat agaattacct ggccagcaat gacctacata    5220
gtcatttcca ttgtgatcct tgactgctac attttcatta attaccctgt cactgatttc    5280
ataatctttc tttaaatgag gatcgattag tacgacaaga tttctaccca acttttttaa    5340
tttggataac agccttttttg gattgggaaa ggagtgctgc ttccaagtaa aatattttttt   5400
gtcgttcgta tactccaagt ccaaccaaat aaaatcgtaa ggaatcatat gagcatccat    5460
ctgagagtcc actgtgagaa cgtccatctc atcattataa ttccatctac attgatggta    5520
ccctatagag gaaatgggcg gtaaaaaggg tctaccagtc aaatcggtaa atttgtcaat    5580
gatagttgga atatctggcc ccagggacat gactacatct atgacaccat tttcggagat    5640
ccaatgagtc atcgttttat ttttactggt gtcatacttt atgtctaccc aagtgtcagc    5700
tgcattgacc caaaagatag atgtggacga agatgaaaac atgaatggga tcgaaccgta    5760
cattggttgg ctggtaccga tgttgtactc aaagacatca acgttgaaaa gcctgtaggg    5820
ttccttttcca cctgaagtgt ccatcagcct tagcgacgtc gcatgttccg gtataccgta    5880
gacattagta gaacccatga agagaaatc tagcgcaacc gattcaggcc ccaaaggcat     5940
agagtcatgc tttgaataca agaaattgtc cttaaacatg ttgaaagttg tttcttctgg    6000
cagcacgtgt gcgaagtttt cctgcttagt tctatgatgt tcaatgttca ggaaattttg    6060
ctcgtttaca ataagtttca gcgcattttg ccagtaaact ttcaattgaa aaggttcagc    6120
aaagatttct acggatacat caccgttccg aagatgaaat gtgtctgcag tggagtttga    6180
aagtgacaaa aatgaagata ttttcgacca gaatgagttc acagtttgtt tttgcttaag    6240
gaagtggaat tgtggaatac tggtcctgtt cgcctcctct tgaaatttct tgtcgaatgc    6300
gtacttccag gtctcattga accgttgtga agagatcaac aaaccgctgc tgttggttgg    6360
cattctctct ttctcatttta tagtgaacct tactgagtga tcctgtaaaa aagagagaga    6420
gaatgggaac tgaacggcta tatcatcgcc ctccaatctt ggtatagttt taattatggt    6480
agcatgaagc acattctcta aaggatcgtg tgcaatagac tcggcgtcca ctttgtaata    6540
gcagtgatga gatttggcaa tatttttctgc ataaaccctg tttctatggc aaaacccaga   6600
ttgcgcacac ttctttaata gatagtcggt aaacgcatgc gaaaaagcgg taaagaagac    6660
caattggcat acgagccatt tcaaaaggac catctcgagg taccgatccg agacggccgg    6720
ctgggccacg tgaattcgac tgctattatc tctgtgtgta tgtgtgtatt gggcaacaag    6780
agcttgtgaa tctgtcctta taaaagacac ccgaagaggc aagattgggt agtacactaa    6840
ttagtggagg gcaactggtt tagggggtttt ggctggctta ttatagtgtc agcgatacta   6900
tacaatctac gatgcccgat gtcggcatac agcacattat tagatccaaa atttccttaa    6960
tttcctattc acgttatata tattaaccag aatttatccg ttgaattgct taatcgactt    7020
cttccacggt tggtccgctg tctccgcctg gggcagcacc acctgggggca ccgccagctg    7080
cgccagctcc gccagggaaa cctccaggga agccaccagg agctccacca ggagctccac    7140
cagcagctcc atagaacttg ctcattattg ggttagcaac ttcttccaat tccttttgcc    7200
tgtccttgta ctcgtctgtg gaagcagatt gtgactcatc atagatctga tctcat        7256
```

<210> SEQ ID NO 24
<211> LENGTH: 5721
<212> TYPE: DNA

<213> ORGANISM: Artificial Sequence
<220> FEATURE:
<223> OTHER INFORMATION: Description of Artificial Sequence:Sequence of plasmid pGAPZAglsIIHDEL.

<400> SEQUENCE: 24

```
tcgagatggt cctttgaaa tggctcgtat gccaattggt cttctttacc gcttttcgc      60
atgcgtttac cgactatcta ttaaagaagt gtgcgcaatc tgggttttgc catagaaaca    120
gggtttatgc agaaaatatt gccaaatctc atcactgcta ttacaaagtg gacgccgagt    180
ctattgcaca cgatccttta gagaatgtgc ttcatgctac cataattaaa actataccaa    240
gattggaggg cgatgatata gccgttcagt tcccattctc tctctctttt ttacaggatc    300
actcagtaag gttcactata aatgagaaag agagaatgcc aaccaacagc agcggtttgt    360
tgatctcttc acaacggttc aatgagacct ggaagtacgc attcgacaag aaatttcaag    420
aggaggcgaa caggaccagt attccacaat tccacttcct taagcaaaaa caaactgtga    480
actcattctg gtcgaaaata tcttcatttt tgtcactttc aaactccact gcagacacat    540
ttcatcttcg aaacggtgat gtatccgtag aaatctttgc tgaaccttt caattgaaag     600
tttactggca aaatgcgctg aaacttattg taaacgagca aaatttcctg aacattgaac    660
atcatagaac taagcaggaa aacttcgcac acgtgctgcc agaagaaaca actttcaaca    720
tgtttaagga caatttcttg tattcaaagc atgactctat gcctttgggg cctgaatcgg    780
ttgcgctaga tttctctttc atgggttcta ctaatgtcta cggtataccg aacatgcga     840
cgtcgctaag gctgatggac acttcaggtg gaaaggaacc ctacaggctt ttcaacgttg    900
atgtctttga gtacaacatc ggtaccagcc aaccaatgta cggttcgatc ccattcatgt    960
tttcatcttc gtccacatct atcttttggg tcaatgcagc tgacacttgg gtagacataa   1020
agtatgacac cagtaaaaat aaaacgatga ctcattggat ctccgaaaat ggtgtcatag   1080
atgtagtcat gtccctgggg ccagatattc aactatcat tgacaaattt accgatttga    1140
ctggtagacc cttttaccg cccatttcct ctatagggta ccatcaatgt agatggaatt    1200
ataatgatga gatggacgtt ctcacagtgg actctcagat ggatgctcat atgattcctt   1260
acgattttat ttggttggac ttggagtata cgaacgacaa aaaatatttt acttggaagc   1320
agcactcctt tcccaatcca aaaaggctgt tatccaaatt aaaaaagttg ggtagaaatc   1380
ttgtcgtact aatcgatcct catttaaaga aagattatga aatcagtgac agggtaatta   1440
atgaaaatgt agcagtcaag gatcacaatg gaaatgacta tgtaggtcat tgctggccag   1500
gtaattctat atggattgat accataagca aatatggcca aaagatttgg aagtccttt    1560
tcgaacggtt tatggatctg ccggctgatt aactaattt attcatttgg aatgatatga    1620
acgagccttc gattttcgat ggcccagaga ccacagctcc aaaagatttg attcacgaca   1680
attacattga ggaaagatcc gtccataaca tatatggtct atcagtgcat gaagctactt   1740
acgacgcaat aaaatcgatt tattcaccat ccgataagcg tcctttcctt ctaacaaggg   1800
cttttttgc cggctctcaa cgtactgctg ccacatggac tggtgacaat gtggccaatt    1860
gggattactt aaagatttcc attcctatgg ttctgtcaaa caacattgct ggtatgccat   1920
ttataggagc cgacatagct ggctttgctg aggatcctac acctgaattg attgcacgtt   1980
ggtaccaagc gggcttatgg tacccatttt ttagagcaca cgcccatata gacaccaaga   2040
gaagagaacc atacttattc aatgaacctt tgaagtcgat agtacgtgat attatccaat   2100
tgagatattt cctgctacct accttataca ccatgtttca taaatcaagt gtcactggat   2160
ttccgataat gaatccaatg tttattgaac accctgaatt tgctgaattg tatcatatcg   2220
```

```
ataaccaatt ttactggagt aattcaggtc tattagtcaa acctgtcacg gagcctggtc   2280
aatcagaaac ggaaatggtt ttcccacccg gtatattcta tgaattcgca tctttacact   2340
cttttataaa caatggtact gatttgatag aaaagaatat ttctgcacca ttggataaaa   2400
ttccattatt tattgaaggc ggtcacatta tcactatgaa agataagtat agaagatctt   2460
caatgttaat gaaaaacgat ccatatgtaa tagttatagc ccctgatacc gagggacgag   2520
ccgttggaga tctttatgtt gatgatggag aaacttttgg ctaccaaaga ggtgagtacg   2580
tagaaactca gttcattttc gaaaacaata ccttaaaaaa tgttcgaagt catattcccg   2640
agaatttgac aggcattcac cacaatactt tgaggaatac caatattgaa aaaatcatta   2700
tcgcaaagaa taatttacaa cacaacataa cgttgaaaga cagtattaaa gtcaaaaaaa   2760
atggcgaaga aagttcattg ccgactagat cgtcatatga gaatgataat aagatcacca   2820
ttcttaacct atcgcttgac ataactgaag attgggaagt tattttttggg cccgaacaaa   2880 aactcatctc agaagaggat ctgaatagcg ccgtcgacca cgacgaactg tgagttttag   2940
ccttagacat gactgttcct cagttcaagt tgggcactta cgagaagacc ggtcttgcta   3000
gattctaatc aagaggatgt cagaatgcca tttgcctgag agatgcaggc ttcattttg    3060 atactttttt atttgtaacc tatatagtat aggattttt ttgtcatttt gtttcttctc    3120
gtacgagctt gctcctgatc agcctatctc gcagctgatg aatatcttgt ggtaggggtt   3180
tgggaaaatc attcgagttt gatgttttc ttggtatttc ccactcctct tcagagtaca    3240
gaagattaag tgagaccttc gtttgtgcgg atcccccaca caccatagct tcaaaatgtt   3300
tctactcctt ttttactctt ccagattttc tcggactccg cgcatcgccg taccacttca   3360
aaacacccaa gcacagcata ctaaatttc cctctttctt cctctagggt gtcgttaatt    3420
acccgtacta aaggtttgga aaagaaaaaa gagaccgcct cgtttctttt tcttcgtcga   3480
aaaaggcaat aaaaattttt atcacgtttc tttttcttga aatttttttt tttagttttt   3540
ttctctttca gtgacctcca ttgatattta agttaataaa cggtcttcaa tttctcaagt   3600
ttcagtttca ttttcttgt tctattacaa cttttttac ttcttgttca ttagaaagaa     3660
agcatagcaa tctaatctaa gggcggtgtt gacaattaat catcggcata gtatatcggc   3720
atagtataat acgacaaggt gaggaactaa accatggcca agttgaccag tgccgttccg   3780
gtgctcaccg cgcgcgacgt cgccggagcg gtcgagttct ggaccgaccg gctcgggttc   3840
tcccgggact tcgtggagga cgacttcgcc ggtgtggtcc gggacgacgt gacccgtgttc   3900 atcagcgcgg tccaggacca ggtggtgccg gacaacaccc tggcctgggt gtgggtgcgc   3960
ggcctggacg agctgtacgc cgagtggtcg gaggtcgtgt ccacgaactt ccggacgcc    4020 tccgggccgg ccatgaccga gatcggcgag cagccgtggg ggcgggagtt cgccctgcgc   4080
gacccggccg gcaactgcgt gcacttcgtg gccgaggagc aggactgaca cgtccgacgg   4140
cggcccacgg gtcccaggcc tcggagatcc gtccccctttt ccttttgtcg atatcatgta   4200
attagttatg tcacgcttac attcacgccc tccccccaca tccgctctaa ccgaaaagga   4260
aggagttaga caacctgaag tctaggtccc tatttatttt tttatagtta tgttagtatt   4320
aagaacgtta tttatatttc aaatttttct ttttttctg tacagacgcg tgtacgcatg    4380
taacattata ctgaaaacct tgcttgagaa ggttttggga cgctcgaagg ctttaatttg   4440
caagctggag accaacatgt gagcaaaagg ccagcaaaag gccaggaacc gtaaaaaggc   4500
cgcgttgctg gcgttttcc ataggctccg cccccctgac gagcatcaca aaaatcgacg    4560
ctcaagtcag aggtggcgaa acccgacagg actataaaga taccaggcgt ttccccctgg   4620
```

```
aagctccctc gtgcgctctc ctgttccgac cctgccgctt accggatacc tgtccgcctt      4680
tctcccttcg ggaagcgtgg cgctttctca atgctcacgc tgtaggtatc tcagttcggt      4740
gtaggtcgtt cgctccaagc tgggctgtgt gcacgaaccc cccgttcagc ccgaccgctg      4800
cgccttatcc ggtaactatc gtcttgagtc caacccggta agacacgact tatcgccact      4860
ggcagcagcc actggtaaca ggattagcag agcgaggtat gtaggcggtg ctacagagtt      4920
cttgaagtgg tggcctaact acggctacac tagaaggaca gtatttggta tctgcgctct      4980
gctgaagcca gttaccttcg gaaaaagagt tggtagctct tgatccggca aacaaaccac      5040
cgctggtagc ggtggttttt ttgtttgcaa gcagcagatt acgcgcagaa aaaaggatc      5100 tcaagaagat cctttgatct tttctacggg gtctgacgct cagtggaacg aaaactcacg      5160
ttaagggatt ttggtcatgc atgagatcag atcttttttg tagaaatgtc ttggtgtcct      5220
cgtccaatca ggtagccatc tctgaaatat ctggctccgt tgcaactccg aacgacctgc      5280
tggcaacgta aaattctccg gggtaaaact taaatgtgga gtaatggaac cagaaacgtc      5340
tcttcccttc tctctccttc caccgcccgt taccgtccct aggaaatttt actctgctgg      5400
agagcttctt ctacgccccc cttgcagcaa tgctcttccc agcattacgt tgcgggtaaa      5460
acggaggtcg tgtacccgac ctagcagccc agggatggaa aagtcccggc cgtcgctggc      5520
aataatagcg gcggacgca tgtcatgaga ttattggaaa ccaccagaat cgaatataaa      5580
aggcgaacac cttcccaat tttggtttct cctgacccaa agactttaaa tttaatttat      5640
ttgtccctat ttcaatcaat tgaacaacta tttcgaaacg aggaattcac gtggcccagc      5700
cggccgtctc ggatcggtac c      5721

<210> SEQ ID NO 25
<211> LENGTH: 7230
<212> TYPE: DNA
<213> ORGANISM: Artificial Sequence
<220> FEATURE:
<223> OTHER INFORMATION: Description of Artificial Sequence:Sequence of
      plasmid pGAPADE1glsIIHDEL.

<400> SEQUENCE: 25
cgtactcacc tctttggtag ccaaaagttt ctccatcatc aacataaaga tctccaacgg       60
ctcgtccctc ggtatcaggg gctataacta ttacatatgg atcgtttttc attaacattg      120
aagatcttct atacttatct ttcatagtga taatgtgacc gccttcaata aataatggaa      180
ttttatccaa tggtgcagaa atattctttt ctatcaaatc agtaccattg tttataaaag      240
agtgtaaaga tgcgaattca tagaatatac cgggtgggaa aaccatttcc gtttctgatt      300
gaccaggctc cgtgacaggt ttgactaata gacctgaatt actccagtaa aattggttat      360
cgatatgata caattcagca aattcagggt gttcaataaa cattggattc attatcggaa      420
atccagtgac acttgattta tgaaacatgg tgtataaggt aggtagcagg aaatatctca      480
attggataat atcacgtact atcgacttca aaggttcatt gaataagtat ggttctcttc      540
tcttggtgtc tatatgggcg tgtgctctaa aaaatgggta ccataagccc gcttggtacc      600
aacgtgcaat caattcaggt gtaggatcct cagcaaagcc agctatgtcg gctcctataa      660
atggcatacc agcaatgttg tttgacagaa ccataggaat ggaaatcttt aagtaatccc      720
aattggccac attgtcacca gtccatgtgg cagcagtacg ttgagagccg gcaaaaaaag      780
cccttgttag aaggaaagga cgcttatcgg atggtaataa aatcgatttt attgcgtcgt      840
aagtagcttc atgcactgat agaccatata tgttatggac ggatctttcc tcaatgtaat      900
```

```
tgtcgtgaat caaatctttt ggagctgtgg tctctgggcc atcgaaaatc gaaggctcgt      960
tcatatcatt ccaaatgaat aaattagtta aatcagccgg cagatccata aaccgttcga     1020
aaaaggactt ccaaatcttt tggccatatt tgcttatggt atcaatccat atagaattac     1080
ctggccagca atgacctaca tagtcatttc cattgtgatc cttgactgct acattttcat     1140
taattaccct gtcactgatt tcataatctt tctttaaatg aggatcgatt agtacgacaa     1200
gatttctacc caacttttt aatttggata acagcctttt tggattggga aaggagtgct     1260
gcttccaagt aaaatatttt ttgtcgttcg tatactccaa gtccaaccaa ataaaatcgt     1320
aaggaatcat atgagcatcc atctgagagt ccactgtgag aacgtccatc tcatcattat     1380
aattccatct acattgatgg taccctatag aggaaatggg cggtaaaaag ggtctaccag     1440
tcaaatcggt aaatttgtca atgatagttg aatatctgg ccccagggac atgactacat      1500
ctatgacacc attttcggag atccaatgag tcatcgtttt atttttactg gtgtcatact     1560
ttatgtctac ccaagtgtca gctgcattga cccaaaagat agatgtggac gaagatgaaa     1620
acatgaatgg gatcgaaccg tacattggtt ggctggtacc gatgttgtac tcaaagacat     1680
caacgttgaa aagcctgtag ggttcctttc cacctgaagt gtccatcagc cttagcgacg     1740
tcgcatgttc cggtataccg tagacattag tagaacccat gaaagagaaa tctagcgcaa     1800
ccgattcagg ccccaaaggc atagagtcat gctttgaata caagaaattg tccttaaaca     1860
tgttgaaagt tgtttcttct ggcagcacgt gtgcgaagtt ttcctgctta gttctatgat     1920
gttcaatgtt caggaaattt tgctcgttta caataagttt cagcgcattt tgccagtaaa     1980
ctttcaattg aaaaggttca gcaaagattt ctacggatac atcaccgttt cgaagatgaa     2040
atgtgtctgc agtggagttt gaaagtgaca aaaatgaaga tattttcgac cagaatgagt     2100
tcacagtttg ttttgctta aggaagtgga attgtggaat actggtcctg ttcgcctcct      2160
cttgaaattt cttgtcgaat gcgtacttcc aggtctcatt gaaccgttgt gaagagatca     2220
acaaaccgct gctgttggtt ggcattctct ctttctcatt tatagtgaac cttactgagt     2280
gatcctgtaa aaagagaga gagaatggga actgaacggc tatatcatcg ccctccaatc      2340
ttggtatagt tttaattatg gtagcatgaa gcacattctc taaaggatcg tgtgcaatag     2400
actcggcgtc cactttgtaa tagcagtgat gagatttggc aatatttct gcataaaccc      2460 tgtttctatg gcaaaaccca gattgcgcac acttctttaa tagatagtcg gtaaacgcat     2520
gcgaaaaagc ggtaaagaag accaattggc atacgagcca tttcaaaagg accatctcga     2580
ggtaccgatc cgagacggcc ggctgggcca cgtgaattcc tcgtttcgaa atagttgttc     2640
aattgattga aatagggaca aataaattaa atttaaagtc tttgggtcag gagaaaccaa     2700
aattgggaaa ggtgttcgcc tttatattc gattctggtg gtttccaata atctcatgac      2760
atgcgtccgc ccgctattat tgccagcgac ggccgggact tttccatccc tgggctgcta     2820
ggtcgggtac acgacctccg ttttacccgc aacgtaatgc tgggaagagc attgctgcaa     2880
gggggccgta aagaagctc tccagcagag taaaatttcc tagggacggt aacgggcggt      2940
ggaaggagag agaagggaag agacgtttct ggttccatta ctccacattt aagttttacc     3000
ccggagaatt ttacgttgcc agcaggtcgt tcggagttgc aacggagcca gatatttcag     3060
agatggctac ctgattggac gaggacacca agacatttct acaaaaaaga tctgatctca     3120
tcgaccggct gcattaatga atcggccaac gcgcgggag aggcggtttg cgtattgggc      3180
gctcttccgc ttcctcgctc actgactcgc tgcgctcggt cgttcggctg cggcgagcgg     3240
tatcagctca ctcaaaggcg gtaatacggt tatccacaga atcaggggat aacgcaggaa     3300
```

```
agaacatgtg agcaaaaggc cagcaaaagg ccaggaaccg taaaaaggcc gcgttgctgg    3360
cgtttttcca taggctccgc cccctgacg agcatcacaa aaatcgacgc tcaagtcaga    3420
ggtggcgaaa cccgacagga ctataaagat accaggcgtt tccccctgga agctccctcg    3480
tgcgctctcc tgttccgacc ctgccgctta ccggatacct gtccgccttt ctcccttcgg    3540
gaagcgtggc gctttctcat agctcacgct gtaggtatct cagttcggtg taggtcgttc    3600
gctccaagct gggctgtgtg cacgaacccc cgttcagcc cgaccgctgc gccttatccg    3660
gtaactatcg tcttgagtcc aacccggtaa gacacgactt atcgccactg gcagcagcca    3720
ctggtaacag gattagcaga gcgaggtatg taggcggtgc tacagagttc ttgaagtggt    3780
ggcctaacta cggctacact agaaggacag tatttggtat ctgcgctctg ctgaagccag    3840
ttaccttcgg aaaaagagtt ggtagctctt gatccggcaa acaaaccacc gctggtagcg    3900
gtggtttttt tgtttgcaag cagcagatta cgcgcagaaa aaaggatct caagaagatc    3960
ctttgatctt ttctacgggg tctgacgctc agtggaacga aaactcacgt taagggattt    4020
tggtcatgag attatcaaaa aggatcttca cctagatcct tttaaattaa aaatgaagtt    4080
ttaaatcaat ctaaagtata tatgagtaaa cttggtctga cagttaccaa tgcttaatca    4140
gtgaggcacc tatctcagcg atctgtctat ttcgttcatc catagttgcc tgactccccg    4200
tcgtgtagat aactacgata cgggagggct taccatctgg ccccagtgct gcaatgatac    4260
cgcgagaccc acgctcaccg gctccagatt tatcagcaat aaaccagcca gccggaaggg    4320
ccgagcgcag aagtggtcct gcaactttat ccgcctccat ccagtctatt aattgttgcc    4380
gggaagctag agtaagtagt tcgccagtta atagtttgcg caacgttgtt gccattgcta    4440
caggcatcgt ggtgtcacgc tcgtcgtttg gtatggcttc attcagctcc ggttcccaac    4500
gatcaaggcg agttacatga tcccccatgt tgtgcaaaaa agcggttagc tccttcggtc    4560
ctccgatcgt tgtcagaagt aagttggccg cagtgttatc actcatggtt atggcagcac    4620
tgcataattc tcttactgtc atgccatccg taagatgctt ttctgtgact ggtgagtact    4680
caaccaagtc attctgagaa tagtgtatgc ggcgaccgag ttgctcttgc ccggcgtcaa    4740
tacgggataa taccgcgcca catagcagaa ctttaaaagt gctcatcatt ggaaaacgtt    4800
cttcggggcg aaaactctca aggatcttac cgctgttgag atccagttcg atgtaaccca    4860
ctcgtgcacc caactgatct tcagcatctt ttactttcac cagcgtttct gggtgagcaa    4920
aaacaggaag gcaaaatgcc gcaaaaaagg gaataagggc gacacggaaa tgttgaatac    4980
tcatactctt ccttttttcaa tagctccaag gcaacaaatt gactactcag accgacattc    5040
attcgttatt gattttaaat caacgataaa cggaatggtt acttgaatga tttcacttta    5100
tgatcattgt ttactaatta cctaaatagg attttatatg gaattggaag aataagggaa    5160
atttcagatg tctgaaaaag gcgaggaggg tactaatcat tcaagcccat tcttgccag    5220
taattgcttc ataagcttca atatacttt ctttactctt gatagcaatt tctgcatcca    5280
tggctacgcc ctctttgcca ttcaatccgt tggccgtcaa ccaatctctg agaaactgct    5340
tatcgtaact ctccttgcgat ttacccactt ggtaagtctt ttgattccaa aatctagaag    5400
aatctggagt taaaacttca tctactagta ccaattcatt gttttcgtcc agtccaaatt    5460
cgaatttcgt atcagcaata atgatcccct tcaaagggc gaagtttttt gcagcagaat    5520
acaactcgac cgccttgaca gcgaccttct cacaaatgtc tttacctaca atctcagcag    5580
cttgttcaat agagatgttt tcatcgtgtt caccctgttc agctttcgtt gaaggtgtga    5640
aaatcggagt tggaaaggcg tcgctctctt gaaggttctc gttttcaacc ttgactccat    5700
```

-continued

```
ggacagtttt tgagttcttg tactctttcc atgcacttcc agtgatgtaa cctctgacaa    5760
tggcttccaa aggtatcagt ctgtgctttt ttactatcaa ggatcgtccc tctaattgag    5820
atttgtattt ttcttcagac agttttgatg gtagtaaagc aaagacttcc ttgtcattag    5880
aagcaaccaa atgattcttt atgtagggtg ccaaaaaatc aaaccagaaa actgagagct    5940
gagtcaaaat ctttccctta tcaggaatac cgtttgtcat aatcacatcg taagcggaga    6000
tacggtcagt tgcgacgaac agcaagttgt tctcatcgac tgcataaatg tctctaacct    6060
ttcctttggc gattaaaggt aggattccgt ccagatcagt gttcacaatg acatacttg     6120 gaaggataca gcaaagtgtg ttggaagcga tgacacatgg aaaggaattt ttcgagtttc    6180
ctagagtagt atattggggc ggtgaaagtt cagatgttta atgcttaata ctcttatact    6240
cttcaaagcg cccaagtgtt tctgccaacc tgactttttt ctgaataatg aatcgttcaa    6300
gtggagtatt taaaccatga ttaagttacg tgatttggca ctggataagg tcgaaaaata    6360
tccgtattca taaacgatta ttggtaaaag ttacaaaata ccactaatta cggagaagct    6420
tagtaacagt tatcatctct tggtcgatta acgcttacaa tttccattcg ccattcaggc    6480
tgcgcaactg ttgggaaggg cgatcggtgc gggcctcttc gctattacgc cagggcctcg    6540
aggcacaaac gaacgtctca cttaatcttc tgtactctga agaggagtgg gaaataccaa    6600
gaaaaacatc aaactcgaat gattttccca accccctacc acaagatatt catcagctgc    6660
gagataggct gatcaggagc aagctcgtac gagaagaaac aaaatgacaa aaaaaatcct    6720
atactatata ggttacaaat aaaaaagtat caaaaatgaa gcctgcatct ctcaggcaaa    6780
tggcattctg acatcctctt gattagaatc tagcaagacc ggtcttctcg taagtgccca    6840
acttgaactg aggaacagtc atgtctaagg ctaaaactca cagttcgtcg tggtcgacgg    6900
cgctattcag atcctcttct gagatgagtt tttgttcggg cccaaaaata acttcccaat    6960
cttcagttat gtcaagcgat aggttaagaa tggtgatctt attatcattc tcatatgacg    7020
atctagtcgg caatgaactt tcttcgccat tttttttgac tttaatactg tctttcaacg    7080
ttatgttgtg ttgtaaatta ttctttgcga taatgatttt ttcaatattg gtattcctca    7140
aagtattgtg gtgaatgcct gtcaaattct cgggaatatg acttcgaaca ttttttaagg    7200
tattgttttc gaaaatgaac tgagtttcta                                    7230
```

```
<210> SEQ ID NO 26
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 26
gacgagatct ttttttcaga ccatatgacc gg                                    32

<210> SEQ ID NO 27
<211> LENGTH: 31
<212> TYPE: DNA
<213> ORGANISM: Artificial Sequence
<220> FEATURE:
<223> OTHER INFORMATION: Description of Artificial Sequence:primer

<400> SEQUENCE: 27
gcggaattct tttctcagtt gatttgtttg t                                     31

<210> SEQ ID NO 28
<211> LENGTH: 45
<212> TYPE: DNA
```

```
<213> ORGANISM: Artificial Sequence
<220> FEATURE:
<223> OTHER INFORMATION: Description of Artificial Sequence:primer

<400> SEQUENCE: 28
gcgggtcgac cacgacgaac tgtgagtttt agccttagac atgac            45

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 29
caggagcaaa gctcgtacga g                                      21
```

PROTEIN GLYCOSYLATION MODIFICATION IN METHYLOTROPHIC YEAST

CROSS-REFERENCE TO RELATED APPLICATION

This application is a continuation of U.S. application Ser. No. 10/672,484, filed Sep. 25, 2003, which is a continuation of U.S. application Ser. No. 09/896,594, filed Jun. 29, 2001, now U.S. Pat. No. 6,803,225, which claims the benefit of U.S. Provisional Application Ser. No. 60/215,676, filed Jun. 30, 2000.

FIELD OF THE INVENTION

The present invention relates to methods and vectors useful for genetically modifying the glycosylation process in methylotrophic yeast strains for the purpose of producing glycoproteins with reduced glycosylation. The present invention further relates to methylotrophic yeast strains generated using the present methods and vectors, as well as glycoproteins produced from such genetically modified strains.

BACKGROUND OF THE INVENTION

The methylotrophic yeasts including *Pichia pastoris* have been widely used for production of recombinant proteins of commercial or medical importance. However, production and medical applications of some therapeutic glycoproteins can be hampered by the differences in the protein-linked carbohydrate biosynthesis between these yeasts and the target organism such as a mammalian subject.

Protein N-glycosylation originates in the endoplasmic reticulum (ER), where an N-linked oligosaccharide ($Glc_3Man_9GlcNAc_2$) assembled on dolichol (a lipid carrier intermediate) is transferred to the appropriate Asn of a nascent protein. This is an event common to all eukaryotic N-linked glycoproteins. The three glucose residues and one specific α-1,2-linked mannose residue are removed by specific glucosidases and an α-1,2-mannosidase in the ER, resulting in the core oligosaccharide structure, $Man_8GlcNAc_2$. The protein with this core sugar structure is transported to the Golgi apparatus where the sugar moiety undergoes various modifications. There are significant differences in the modifications of the sugar chain in the Golgi apparatus between yeast and higher eukaryotes.

In mammalian cells, the modification of the sugar chain proceeds via 3 different pathways depending on the protein moiety to which it is added. That is, (1) the core sugar chain does not change; (2) the core sugar chain is changed by adding the N-acetylglucosamine-1-phosphate moiety (GlcNAc-1-P) in UDP-N-acetyl glucosamine (UDP-GlcNAc) to the 6-position of mannose in the core sugar chain, followed by removing the GlcNAc moiety to form an acidic sugar chain in the glycoprotein; or (3) the core sugar chain is first converted into $Man_5GlcNAc_2$ by removing 3 mannose residues with mannosidase I; $Man_5GlcNAc_2$ is further modified by adding GlcNAc and removing 2 more mannose residues, followed by sequentially adding GlcNAc, galactose (Gal), and N-acetylneuraminic acid (also called sialic acid (NeuNAc)) to form various hybrid or complex sugar chains (R. Kornfeld and S. Kornfeld, *Ann. Rev. Biochem.* 54: 631-664, 1985; Chiba et al *J. Biol. Chem.* 273: 26298-26304, 1998).

In yeast, the modification of the sugar chain in the Golgi involves a series of additions of mannose residues by different mannosyltransferases ("outer chain" glycosylation). The structure of the outer chain glycosylation is specific to the organisms, typically with more than 50 mannose residues in *S. cerevisiae*, and most commonly with structures smaller than $Man_{14}GlcNAc_2$ in *Pichia pastoris*. This yeast-specific outer chain glycosylation of the high mannose type is also denoted hyperglycosylation.

Hyperglycosylation is often undesired since it leads to heterogeneity of a recombinant protein product in both carbohydrate composition and molecular weight, which may complicate the protein purification. The specific activity (units/weight) of hyperglycosylated enzymes may be lowered by the increased portion of carbohydrate. In addition, the outer chain glycosylation is strongly immunogenic which is undesirable in a therapeutic application. Moreover, the large outer chain sugar can mask the immunogenic determinants of a therapeutic protein. For example, the influenza neuraminidase (NA) expressed in *P. pastoris* is glycosylated with N-glycans containing up to 30-40 mannose residues. The hyperglycosylated NA has a reduced immunogenicity in mice, as the variable and immunodominant surface loops on top of the NA molecule are masked by the N-glycans (Martinet et al. *Eur J. Biochem.* 247: 332-338, 1997).

Therefore, it is desirable to genetically engineer methylotrophic yeast strains in which glycosylation of proteins can be manipulated and from which recombinant proteins can be produced that would not be compromised in structure or function by large N-glycan side chains.

SUMMARY OF THE INVENTION

The present invention is directed to methods and vectors useful for genetically modifying the glycosylation process in methylotrophic yeast strains to produce glycoproteins with reduced glycosylation. Methylotrophic yeast strains generated using the present methods and vectors, as well as glycoproteins produced from such genetically modified strains are also provided.

In one embodiment, the present invention provides vectors useful for making genetically engineered methylotrophic yeast strains which are capable of producing glycoproteins with reduced glycosylation.

In one aspect, the present invention provides "knock-in" vectors which are capable of expressing in a methylotrophic yeast strain one or more proteins whose enzymatic activities lead to a reduction of glycosylation in glycoproteins produced by the methylotrophic yeast strain.

In a preferred embodiment, the knock-in vectors of the present invention include a nucleotide sequence coding for an α-1,2-mannosidase or a functional part thereof and are capable of expressing the α-1,2-mannosidase or the functional part in a methylotrophic yeast strain. A preferred nucleotide sequence is a nucleotide sequence encoding the α-1,2-mannosidase of a fungal species, and more preferably, *Trichoderma reesei*. Preferably, the α-1,2-mannosidase expression vector is engineered such that the α-1,2-mannosidase or a functional part thereof expressed from the vector includes an ER-retention signal. A preferred ER-retention signal is HDEL (SEQ ID NO: 1). The α-1,2-mannosidase coding sequence can be operable linked to a constitutive or inducible promoter, and a 3' termination sequence. The vectors can be integrative vectors or replicative vectors. Particularly preferred α-1,2-mannosidase expression vectors include pGAPZMFManHDEL, pGAPZMFManMycHDEL, pPICZBMFManMycHDEL, pGAPZmManHDEL, pGAPZmMycManHDEL, pPIC9mMycManHDEL and pGAPZmMycManHDEL.

In another preferred embodiment, the knock-in vectors of the present invention include a sequence coding for a glucosidase II or a functional part thereof and are capable of expressing the glucosidase II or the functional part in a methylotrophic yeast strain. A preferred nucleotide sequence is a nucleotide sequence encoding the glucosidase II of a fungal species, and more preferably, Saccharomyces cerevisiae. Preferably, the glucosidase II expression vector is engineered such that the glucosidase II or a functional part thereof expressed from the vector includes an ER-retention signal. A preferred ER-retention signal is HDEL (SEQ ID NO: 1). The glucosidase II coding sequence can be operable linked to a constitutive or inducible promoter, and a 3' termination sequence. The vectors can be integrative vectors or replicative vectors. Particularly preferred glucosidase II expression vectors include pGAPZAGLSII, pPICZAGLSII, pAOX2ZAGLSII, pYPTIZAGLSII, pGAPADEglsII, pPIC-ADEglsII, pAOX2ADEglsII, pYPTIADEglsII, pGAPZAglsIIHDEL and pGAPADEglsIIHDEL.

Expression vectors which include both of an α-1,2-mannosidase expression unit and a glucosidase II expression unit are also provided by the present invention.

In another aspect, the present invention provides "knock-out" vectors which, when introduced into a methylotrophic yeast strain, inactivate or disrupt a gene thereby facilitating the reduction in the glycosylation of glycoproteins produced in the methylotrophic yeast strain.

In one embodiment, the present invention provides a "knock-out" vector which, when introduced into a methylotrophic yeast strain, inactivates or disrupts the Och1 gene. A preferred Och1 knock-out vector is pBLURA5'PpOCH1.

Still another embodiment of the present invention provides vectors which include both a knock-in unit and a knock-out unit.

Furthermore, any of the knock-in or knock-out vectors of the present invention can also include a nucleotide sequence capable of expressing a heterologous protein of interest in a methylotrophic yeast.

Another embodiment of the present invention provides methods of modifying the glycosylation in a methylotrophic yeast by transforming the yeast with one or more vectors of the present invention.

Strains of a methylotrophic yeast which can be modified using the present methods include, but are not limited to, yeast strains capable of growth on methanol such as yeasts of the genera *Candida, Hansenula, Torulopsis*, and *Pichia*. Preferred methylotrophic yeasts are of the genus *Pichia*. Especially preferred are *Pichia pastoris* strains GS115 (NRRL Y-15851), GS190 (NRRL Y-18014), PPF1 (NRRL Y-18017), PPY120H, yGC4, and strains derived therefrom. Methylotrophic yeast strains which can be modified using the present methods also include those methylotrophic yeast strains which have been engineered to express one or more heterologous proteins of interest. The glycosylation on the heterologous proteins expressed from these previously genetically engineered strains can be reduced by transforming such strains with one or more of the vectors of the present invention Methylotrophic yeast strains which are modified by practicing the present methods are provided in another embodiment of the present invention.

A further aspect of the present invention is directed to methods of producing glycoproteins with a reduced glycosylation.

In accordance with such methods, a nucleotide sequence capable of expressing a glycoprotein can be introduced into a methylotrophic yeast strain which has previously been transformed with one or more of the vectors of the present invention. Alternatively, a methylotrophic yeast strain which has been genetically engineered to express a glycoprotein can be transformed with one or more of the vectors of the present invention. Moreover, if a methylotrophic yeast strain is not transformed with a nucleotide sequence encoding a glycoprotein of interest or any of the vectors of the present invention, such yeast strain can be transformed, either consecutively or simultaneously, with both a nucleotide sequence capable of expressing the glycoprotein and one or more vectors of the present invention. Additionally, a methylotrophic yeast strain can be transformed with one or more of the present knock-in and/or knock-out vectors which also include a nucleotide sequence capable of expressing a glycoprotein in the methylotrophic yeast strain.

Glycoproteins products produced by using the methods of the present invention, i.e., glycoproteins with reduced N-glycosylation, are also part of the present invention.

Kits which include one or more of the vectors of the present invention, or one or more strains modified to produce glycoproteins with reduced glycosylation, are also provided.

DETAILED DESCRIPTION OF THE INVENTION

Figure 1:
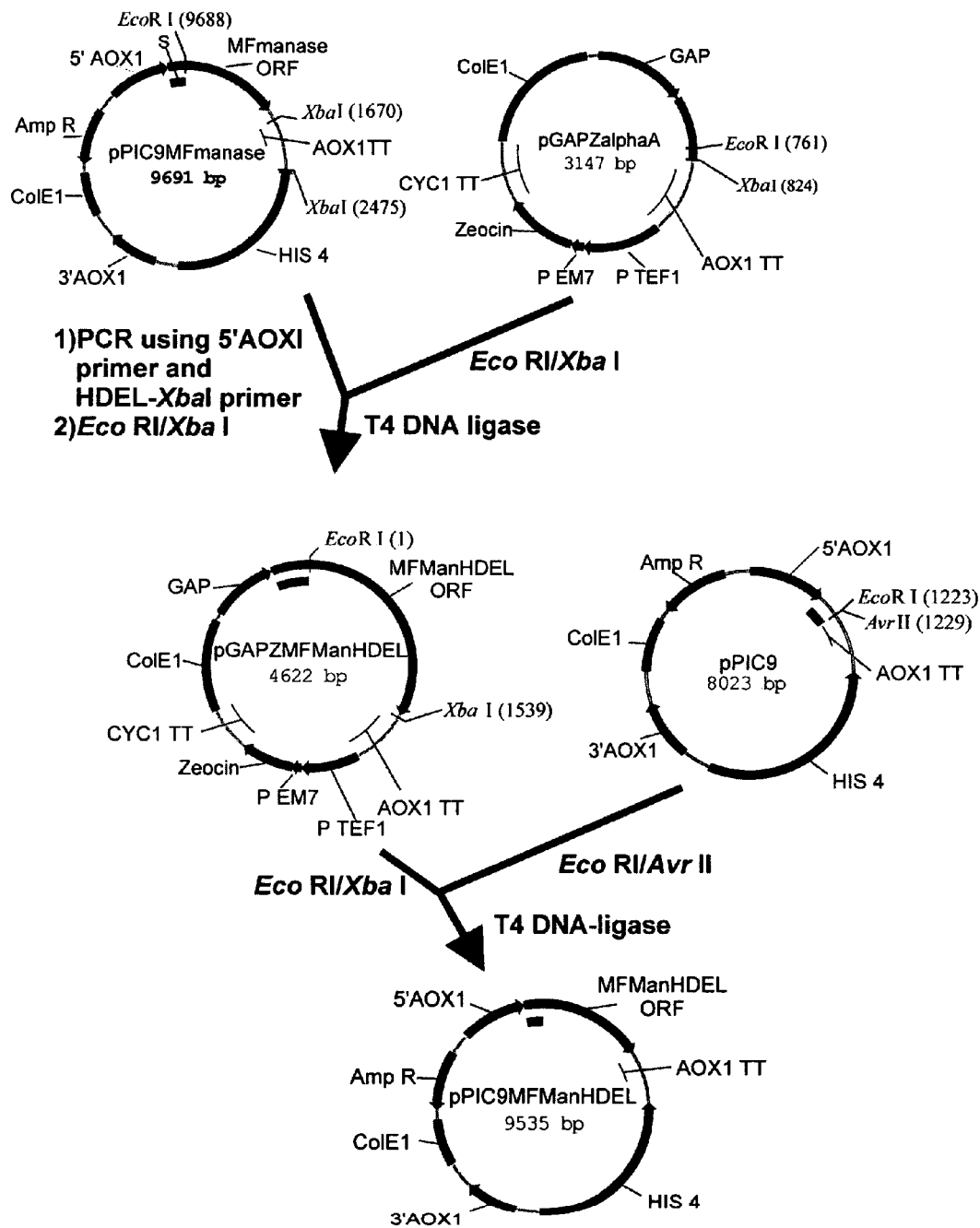
FIG. 1 depicts vectors carrying an HDEL (SEQ ID NO: 1)-tagged *Trichoderma reesei* α-1,2-mannosidase expression cassette and describes the way in which these vectors were constructed according to methods known in the art. Abbreviations used throughout construction schemes: 5' AOX1 or AOX1 P: *Pichia pastoris* AOX1 promoter sequence; Amp R: ampicillin resistance gene; ColE1: ColE1 origin of replication; 3'AOX1: 3' sequences of the *Pichia pastoris* AOX1 gene; HIS4: HIS4 gene of *Pichia pastoris*. AOX TT: transcription terminator sequence of the *Pichia pastoris* AOX1 gene; ORF: open reading frame; S: secretion signal; P TEF1: the promoter sequence of the *Saccharomyces cerevisiae* transcription elongation factor 1 gene; P EM7: synthetic constitutive prokaryotic promoter EM7; Zeocin: Zeocin resistance gene; CYC1 TT: 3' end of the *S. cerevisiae* CYC1 gene; GAP: promoter sequence of the *Pichia pastoris* glyceraldehyde-3-phosphate dehydrogenase gene; PpURA3: *Pichia pastoris* URA3 gene. As can be seen in this figure, the *Trichoderma reesei* α-1,2-mannosidase was operably linked to the coding sequence for the *S. cerevisiae* α-mating factor secretion signal sequence and further operably linked at the 3' terminus of the coding sequence to the coding sequence for an HDEL (SEQ ID NO: 1) peptide. The whole fusion construct was operably linked to either the *P. pastoris* AOX1 promoter (in pPIC9MFManHDEL) or to the *P. pastoris* GAP promotor (in pGAPZMFManHDEL).
Figure 2:
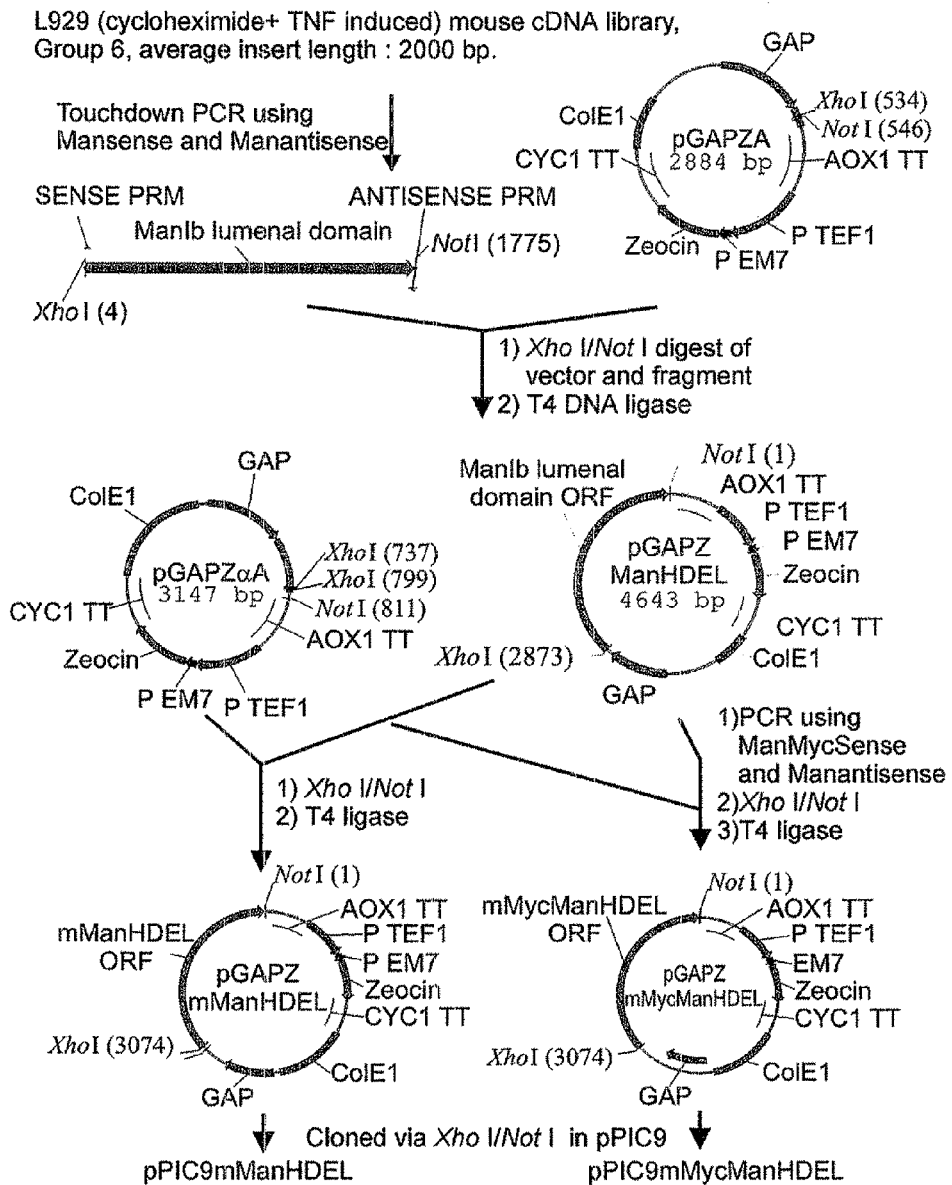
FIG. 2 depicts vectors carrying an HDEL (SEQ ID NO: 1)-tagged *Mus musculus* α-1,2-mannosidase IB expression cassette and describes the way in which these vectors were constructed according to methods known in the art. As can be seen in this figure, the catalytic domain of the *Mus musculus* α-1,2-mannosidase IB was operably linked to the coding sequence for the *S. cerevisiae* α-mating factor secretion signal sequence and further operably linked at the 3' terminus of the coding sequence to the coding sequence for an HDEL (SEQ ID NO: 1) peptide. The whole fusion construct was operably linked to either the *P. pastoris* AOX1 promoter (in pPIC9 mManHDEL) or to the *P. pastoris* GAP promotor (in pGAPZmManHDEL). Furthermore, variants of the expression cassette were made in which the coding sequence for a cMyc epitope tag was inserted between the coding sequence for the *S. cerevisiae* α-Mating Factor secretion signal sequence and the coding sequence for the catalytic domain of the *Mus musculus* α-1,2-mannosidase IB. This expression cassette was also operably linked to either the *P. pastoris* AOX1 promoter (in pPIC9 mMycManHDEL) or to the *P. pastoris* GAP promotor (in pGAPZmMycManHDEL).
Figure 3:
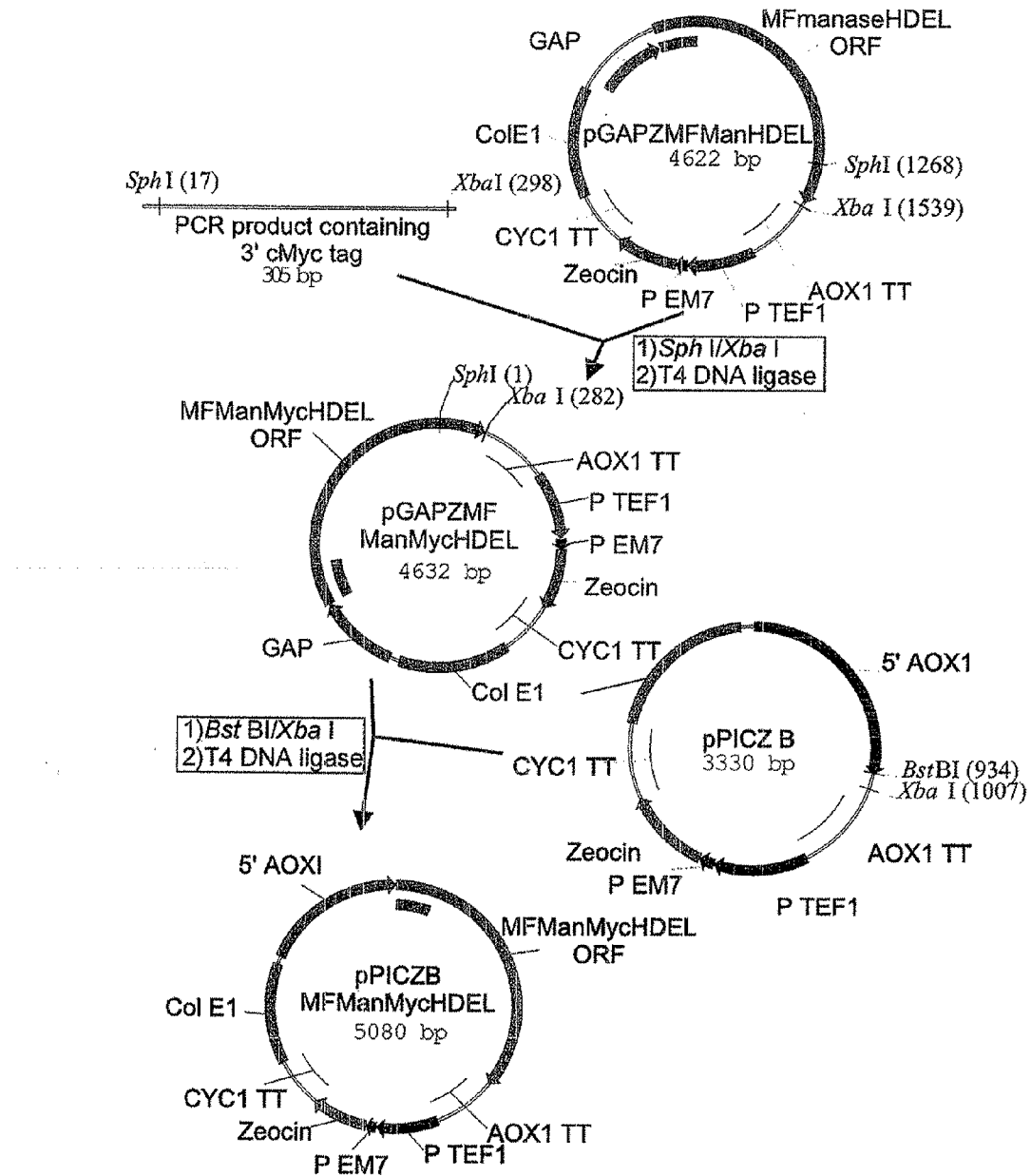
FIG. 3 depicts vectors carrying a MycHDEL tagged *Trichoderma reesei* α-1,2-mannosidase and the way in which these vectors were obtained. The resulting fusion construction was again operably linked to either the *P. pastoris* AOX1 promoter (in pPICZBMFManMycHDEL) or to the P. pastoris GAP promotor (in pGAPZMFManMycHDEL).

It has been established that the majority of N-glycans on glycoproteins leaving the endoplasmic reticulum (ER) of Pichia have the core $Man_8GlcNAc_2$ oligosaccharide structure. After the proteins are transported from the ER to the Golgi apparatus, additional mannose residues are added to this core sugar moiety by different mannosyltransferases, resulting in glycoproteins with large mannose side chains. Such hyperglycosylation of recombinant glycoproteins is undesirable in many instances. Accordingly, the present invention provides methods and vectors for genetically modifying methylotrophic yeast strains to produce glycoproteins with reduced glycosylation. Methylotrophic yeast strains generated using the present methods and vectors, as well as glycoproteins produced from such genetically modified strains are also provided.

In one embodiment, the present invention provides vectors useful for genetically modifying methylotrophic yeast strains to produce glycoproteins with reduced glycosylation.

In one aspect, the present invention provides "knock-in" vectors which are capable of expressing in a methylotrophic yeast strain one or more proteins whose enzymatic activities lead to a reduction of glycosylation in glycoproteins produced by the methylotrophic yeast strain. According to the present invention, such proteins include, e.g., an α-1,2-mannosidase, a glucosidase II, or functional parts thereof.

In a preferred embodiment, the vectors of the present invention include a sequence coding for an α-1,2-mannosidase or a functional part thereof and are capable of expressing the α-1,2-mannosidase or the functional part in a methylotrophic yeast strain.

An α-1,2-mannosidase cleaves the α-1,2-linked mannose residues at the non-reducing ends of $Man_8GlcNAc_2$, and converts this core oligosaccharide on glycoproteins to $Man_5GlcNAc_2$. In vitro, $Man_5GlcNAc_2$ is a very poor substrate for any Pichia Golgi mannosyltransferase, i.e., mannose residues can not be added to this sugar structure. On the other hand, Man$_5$GlcNAc$_2$ is the acceptor substrate for the mammalian N-acetylglucosaminyl-transferase I and is an intermediate for the hybrid- and complex-type sugar chains characteristic of mammalian glycoproteins. Thus, by way of introducing an α-1,2-mannosidase into methylotrophic yeasts such as *Pichia*, glycoproteins with reduced mannose content can be produced.

According to the present invention, the nucleotide sequence encoding an α-1,2-mannosidase for use in the expression vector of the present invention can derive from any species. A number of α-1,2-mannosidase genes have been cloned and are available to those skilled in the art, including mammalian genes encoding, e.g., a murine α-1,2-mannosidase (Herscovics et al. *J. Biol. Chem.* 269: 9864-9871, 1994), a rabbit α-1,2-mannosidase (Lal et al. *J. Biol. Chem.* 269: 9872-9881, 1994) or a human α-1,2-mannosidase (Tremblay et al. *Glycobiology* 8: 585-595, 1998), as well as fungal genes encoding, e.g., an *Aspergillus* α-1,2-mannosidase (msdS gene), a *Trichoderma reesei* α-1,2-mannosidase (Maras et al. *J. Biotechnol.* 77: 255-263, 2000), or a *Saccharomyces cerevisiae* α-1,2-mannosidase. Protein sequence analysis has revealed a high degree of conservation among the eukaryotic α-1,2-mannosidases identified so far.

Preferably, the nucleotide sequence for use in the present vectors encodes a fungal α-1,2-mannosidase, more preferably, a *Trichoderma reesei* α-1,2-mannosidase, and more particularly, the *Trichoderma reesei* α-1,2-mannosidase described by Maras et al. *J. Biotechnol.* 77: 255-63 (2000).

According to the present invention, the nucleotide sequence can also code for only a functional part of an α-1,2-mannosidase.

By "functional part" is meant a polypeptide fragment of an α-1,2-mannosidase which substantially retains the enzymatic activity of the full-length protein. By "substantially" is meant at least about 40%, or preferably, at least 50% or more of the enzymatic activity of the full-length α-1,2-mannosidase is retained. For example, as illustrated by the present invention, the catalytic domain of the murine α-1,2-mannosidase IB constitutes a "functional part" of the murine α-1,2-mannosidase IB. Those skilled in the art can readily identify and make functional parts of an α-1,2-mannosidase using a combination of techniques known in the art. Predictions of the portions of an α-1,2-mannosidase essential to or sufficient to confer the enzymatic activity can be made based on analysis of the protein sequence. The activity of a portion of an α-1,2-mannosidase of interest, expressed and purified from an appropriate expression system, can be verified using in vitro or in vivo assays described hereinbelow.

In accordance with the present invention, an α-1,2-mannosidase or a functional part thereof expressed in a methylotrophic yeast strain preferably is targeted to a site in the secretory pathway where Man$_8$GlcNAc$_2$ (the substrate of α-1,2-mannosidase) is already formed on a glycoprotein, but has not reached a Golgi glycosyltransferase which elongates the sugar chain with additional mannose residues.

Accordingly, in a preferred embodiment of the present invention, the α-1,2-mannosidase expression vector is engineered as such that the α-1,2-mannosidase or a functional part thereof expressed from the vector includes an ER-retention signal.

"An ER retention signal" refers to a peptide sequence which directs a protein having such peptide sequence to be transported to and retained in the ER. Such ER retention sequences are often found in proteins that reside and function in the ER.

Multiple choices of ER retention signals are available to those skilled in the art, e.g., the first 21 amino acid residues of the *S. cerevisiae* ER protein MNS1 (Martinet et al. *Biotechnology Letters* 20: 1171-1177, 1998). A preferred ER retention signal for use in the present invention is peptide HDEL (SEQ ID NO: 1). The HDEL (SEQ ID NO: 1) peptide sequence, found in the C-terminus of a number of yeast proteins, acts as a retention/retrieval signal for the ER (Pelham *EMBO J.* 7: 913-918, 1988). Proteins with an HDEL (SEQ ID NO: 1) sequence are bound by a membrane-bound receptor (Erd2p) and then enter a retrograde transport pathway for return to the ER from the Golgi apparatus.

According to the present invention, an ER retention signal can be placed anywhere in the protein sequence of an α-1,2-mannosidase, but preferably at the C-terminus of the α-1,2-mannosidase.

The α-1,2-mannosidase for use in the present invention can be further modified, e.g., by insertion of an epitope tag to which antibodies are available, such as Myc, HA, FLAG and His6 tags well-known in the art. An epitope-tagged α-1,2-mannosidase can be conveniently purified, or monitored for both expression and intracellular localization.

An ER retention signal and an epitope tag can be readily introduced into a protein of interest by inserting nucleotide sequences coding for such signal or tag into the nucleotide sequence encoding the protein of interest, using any of the molecular biology techniques known in the art.

In another preferred embodiment, the vectors of the present invention include a sequence coding for a glucosidase II or a functional part thereof and are capable of expressing the glucosidase II or the functional part in the methylotrophic yeast strain.

It has been established that the initial N-linked oligosaccharide (Glc$_3$Man$_9$GlcNAc$_2$), transferred in the ER onto a protein, is cleaved in the ER by specific glucosidases to remove the glucose residues, and by a mannosidase to remove one specific α-1,2-linked mannose. It has been observed by the present inventors that some recombinant proteins expressed in *Pichia* have residual glucose residues on the sugar moiety when such proteins leave the ER for the Golgi apparatus. The residual glucose molecules present on the sugar structure prevent the complete digestion of the sugar moiety by an α-1,2-mannosidase, and the introduction of an exogenous glucosidase can facilitate the removal of these glucose residues.

According to the present invention, the nucleotide sequence encoding a glucosidase II can derive from any species. Glucosidase II genes have been cloned from a number of mammalian species including rat, mouse, pig and human. The glucosidase II protein from these mammalian species consists of an alpha and a beta subunit. The alpha subunit is about 110 kDa and contains the catalytic activity of the enzyme, while the beta subunit has a C-terminal HDEL (SEQ ID NO: 1) ER-retention sequence and is believed to be important for the ER localization of the enzyme. The glucosidase II gene from *S. cerevisiae* has also been cloned (ORF YBR229c, located on chromosome II). This gene encodes a protein of about 110 kDa, which shows a high degree of homology to the mammalian alpha subunits.

A preferred glucosidase II gene for use in the present vectors is from a fungal species such as *Pichia pastoris* and *S. cerevisiae*. An example of a fungal glucosidase II gene is the *S. cerevisiae* glucosidase II alpha subunit gene.

According to the present invention, the nucleotide sequence can also encode only a functional part of a glucosidase II. By "functional part" is meant a polypeptide fragment of a glucosidase II which substantially retains the enzymatic activity of the full-length protein. By "substantially" is meant at least about 40%, or preferably, at least 50% or more of the enzymatic activity of the full-length glucosidase II is retained. Functional parts of a glucosidase II can be identified and made by those skilled in the art using a variety of techniques known in the art.

In a preferred embodiment of the present invention, the glucosidase II protein is engineered to include an ER retention signal such that the protein expressed in a methylotrophic yeast strain is targeted to the ER and retains therein for function. ER retention signals are as described hereinabove, e.g., the HDEL (SEQ ID NO: 1) peptide sequence.

The glucosidase II for use in the present invention can be further modified, e.g., by insertion of an epitope tag to which antibodies are available, such as Myc, HA, FLAG, and His6 tag, which are well-known in the art.

According to the present invention, the "knock-in" vectors can include either or both of an α-1,2-mannosidase coding sequence and a glucosidase II coding sequence.

Further according to the present invention, the nucleotide sequence coding for the enzyme to be expressed (e.g., an α-1,2-mannosidase or a functional part thereof, or a glucosidase II or a functional part thereof) can be placed in an operable linkage to a promoter and a 3' termination sequence.

Promoters appropriate for expression of a protein in a methylotrophic yeast can include both constitutive promoters and inducible promoters. Constitutive promoters include e.g., the *Pichia pastoris* glyceraldehyde-3-phosphate dehydrogenase promoter ("the GAP promoter"). Examples of inducible promoters include, e.g., the *Pichia pastoris* alcohol oxidase I promoter ("the AOXI promoter") (U.S. Pat. No. 4,855,231), or the *Pichia pastoris* formaldehyde dehydrogenase promoter ("the FLD promoter") (Shen et al. Gene 216: 93-102, 1998).

3' termination sequences are sequences 3' to the stop codon of a structural gene which function to stabilize the mRNA transcription product of the gene to which the sequence is operably linked, such as sequences which elicit polyadenylation. 3' termination sequences can be obtained from *Pichia* or other methylotrophic yeast. Examples of *Pichia pastoris* 3' termination sequences useful for the practice of the present invention include termination sequences from the AOX1 gene, p40 gene, HIS4 gene and FLD1 gene.

The vectors of the present invention preferably contain a selectable marker gene. The selectable marker may be any gene which confers a selectable phenotype upon a methylotrophic yeast strain and allows transformed cells to be identified and selected from untransformed cells. The selectable marker system may include an auxotrophic mutant methylotrophic yeast strain and a wild type gene which complements the host's defect. Examples of such systems include the *Saccharomyces cerevisiae* or *Pichia pastoris* HIS4 gene which may be used to complement his4 *Pichia* strains, or the *S. cerevisiae* or *Pichia pastoris* ARG4 gene which may be used to complement *Pichia pastoris* arg mutants. Other selectable marker genes which function in *Pichia pastoris* include the Zeo$^R$ gene, the G418$^R$ gene, and the like.

The vectors of the present invention can also include an autonomous replication sequence (ARS). For example, U.S. Pat. No. 4,837,148 describes autonomous replication sequences which provide a suitable means for maintaining plasmids in *Pichia pastoris*. The disclosure of U.S. Pat. No. 4,837,148 is incorporated herein by reference.

The vectors can also contain selectable marker genes which function in bacteria, as well as sequences responsible for replication and extrachromosomal maintenance in bacteria. Examples of bacterial selectable marker genes include ampicillin resistance (Amp$^r$), tetracycline resistance (Tet$^r$), neomycin resistance, hygromycin resistance, and zeocin resistance (Zeo$^R$) genes.

According to the present invention, the nucleotide sequence encoding the protein to be expressed in a methylotrophic yeast can be placed in an integrative vector or a replicative vector (such as a replicating circular plasmid).

Integrative vectors are disclosed, e.g., in U.S. Pat. No. 4,882,279 which is incorporated herein by reference. Integrative vectors generally include a serially arranged sequence of at least a first insertable DNA fragment, a selectable marker gene, and a second insertable DNA fragment. The first and second insertable DNA fragments are each about 200 nucleotides in length and have nucleotide sequences which are homologous to portions of the genomic DNA of the species to be transformed. A nucleotide sequence containing a structural gene of interest for expression is inserted in this vector between the first and second insertable DNA fragments whether before or after the marker gene. Integrative vectors can be linearized prior to yeast transformation to facilitate the integration of the nucleotide sequence of interest into the host cell genome.

Replicative and integrative vectors carrying either or both of an α-1,2-mannosidase coding sequence or a glucosidase II coding sequence can be constructed by standard techniques known to one of ordinary skill in the art and found, for example, in Sambrook et al. (1989) in Molecular Cloning: A Laboratory Manual, or any of a myriad of laboratory manuals on recombinant DNA technology that are widely available.

Preferred vectors of the present invention carrying an α-1, 2-mannosidase expression sequence include pGAPZMFManHDEL, pGAPZMFManMycHDEL, pPICZBMFManMycHDEL, pGAPZmManHDEL, pGAPZmMycManHDEL, pPIC9 mMycManHDEL and pGAPZmMycManHDEL, which are further described in the Examples hereinbelow.

Preferred vectors of the present invention carrying a glucosidase II expression sequence include pGAPZAGLSII, pPICZAGLSII, pAOX2ZAGLSII, pYPTIZAGLSII, pGAPADE1glsII, pPICADE1 glsII, pAOX2ADE1glsII, pYPTIADE1glsII, pGAP ZAglsIIHDEL and pGAPADE1glsIIHDEL, which are further described in the Examples hereinbelow.

In another aspect, the present invention provides "knock-out" vectors which, when introduced into a methylotrophic yeast strain, inactivate or disrupt a gene thereby facilitating the reduction in the glycosylation of glycoproteins produced in the methylotrophic yeast strain.

In one embodiment, the present invention provides a "knock-out" vector which, when introduced into a methylotrophic yeast strain, inactivates or disrupts the Och1 gene.

The *S. cerevisiae* OCH1 gene has been cloned (Nakayama et al. EMBO J. 11: 2511-2519, 1992). It encodes a membrane bound α-1,6-mannosyltransferase, localized in the early Golgi complex, that is functional in the initiation of α-1,6-polymannose outer chain addition to the N-linked core oligosaccharide (Man$_5$GlcNAc$_2$ and Man$_8$GlcNAc$_2$) (Nakanishi-Shindo et al. J. Biol. Chem. 268: 26338-26345, 1993).

A *Pichia* sequence has been described in Japanese Patent Application No. 07145005 that encodes a protein highly homologous to the *S. cerevisiae* OCH1. For purpose of the present invention, this sequence is denoted herein as "the *Pichia* OCH1 gene". Those skilled in the art can isolate the OCH1 genes from other methylotrophic yeasts using techniques well known in the art.

According to the present invention, a disruption in the OCH1 gene of a methylotrophic yeast can result in either the production of an inactive protein product or no product. The disruption may take the form of an insertion of a heterologous DNA sequence into the coding sequence and/or the deletion of some or all of the coding sequence. Gene disruptions can be generated by homologous recombination essentially as described by Rothstein (in *Methods in Enzymology*, Wu et al., eds., vol 101:202-211, 1983).

To disrupt the Och1 gene by homologous recombination, an Och1 knock-out vector can be constructed in such a way to include a selectable marker gene. The selectable marker gene is operably linked, at both 5' and 3' end, to portions of the Och1 gene of sufficient length to mediate homologous recombination. The selectable marker can be one of any number of genes which either complement host cell auxotrophy or provide antibiotic resistance, including URA3, LEU2 and HIS3 genes. Other suitable selectable markers include the CAT gene, which confers chloramphenicol resistance on yeast cells, or the lacZ gene, which results in blue colonies due to the expression of active β-galactosidase. Linearized DNA fragments of an Och1 knock-out vector are then introduced into host methylotrophic yeast cells using methods well known in the art. Integration of the linear fragments into the genome and the disruption of the Och1 gene can be determined based on the selection marker and can be verified by, for example, Southern Blot analysis.

Alternatively, an Och1 knock-out vector can be constructed in such a way to include a portion of the Och1 gene to be disrupted, which portion is devoid of any Och1 promoter sequence and encodes none or an inactive fragment of the Och1 protein. By "an inactive fragment", it is meant a fragment of the Och1 protein which has, preferably, less than about 10% and most preferably, about 0% of the activity of the full-length OCH1 protein. Such portion of the OCH1 gene is inserted in a vector in such a way that no known promoter sequence is operably linked to the OCH1 sequence, but that a stop codon and a transcription termination sequence are operably linked to the portion of the Och1 gene. This vector can be subsequently linearized in the portion of the OCH1 sequence and transformed into a methylotrophic yeast strain using any of the methods known in the art. By way of single homologous recombination, this linearized vector is then integrated in the OCH1 gene. Two Och1 sequences are produced in the chromosome as a result of the single homologous recombination. The first Och1 sequence is the portion of the Och1 gene from the vector, which is now under control of the OCH1 promoter of the host methylotrophic yeast, yet cannot produce an active OCH1 protein as such Och1 sequence codes for no or an inactive fragment of the OCH1 protein, as described hereinabove. The second Och1 sequence is a full OCH1 coding sequence, but is not operably linked to any known promoter sequence and thus, no active messenger is expected to be formed for synthesis of an active OCH1 protein. Preferably, an inactivating mutation is introduced in the OCH1 sequence, to the 5' end of the site of linearization of the vector and to the 3' end of the translation initiation codon of OCH1. By "inactivating mutation" it is meant a mutation introducing a stop codon, a frameshift mutation or any other mutation causing a disruption of the reading frame. Such mutation can be introduced into an Och1 sequence using any of the site directed mutagenesis methods known in the art. Such inactivating mutation ensures that no functional OCH1 protein can be formed even if there exist some promoter sequences 5' to the Och1 sequence in the knock-out vector.

A preferred Och1 knock-out vector of the present invention is pBLURA5'PpOCH1.

If desired, either or both of a mannosidase expression sequence and a glucosidase expression sequence can be carried on the same plasmid used to disrupt the OCH1 gene to create a "knock-in-and-knock-out" vector.

Additionally, any of the above-described vectors can further include a nucleotide sequence capable of expressing a glycoprotein of interest in a methylotrophic yeast strain.

Another aspect of the present invention is directed to methods of modifying methylotrophic yeast strains to reduce glycosylation on proteins produced by the methylotrophic yeast strains. In accordance with the present methods, methylotrophic yeast strains are modified by transforming into these yeast strains with one or more, i.e., at least one, knock-in and/or knock-out vectors of the present invention as described herein above.

Methylotrophic yeast strains which can be modified using the present methods include but are not limited to yeast capable of growth on methanol such as yeasts of the genera *Candida*, *Hansenula*, *Torulopsis*, and *Pichia*. A list of species which are exemplary of this class of yeasts can be found in C. Anthony (1982), *The Biochemistry of Methylotrophs*, 269. *Pichia pastoris*, *Pichia methanolica*, *Pichia anomola*, *Hansenula polymorpha* and *Candida boidinii* are examples of methylotrophic yeasts useful in the practice of the present invention. Preferred methylotrophic yeasts are of the genus *Pichia*. Especially preferred are *Pichia pastoris* strains GS115 (NRRL Y-15851); GS190 (NRRL Y-18014) disclosed in U.S. Pat. No. 4,818,700; PPF1 (NRRL Y-18017) disclosed in U.S. Pat. No. 4,812,405; PPY120H and yGC4; as well as strains derived therefrom.

Methylotrophic yeast strains which can be modified using the present methods also include those methylotrophic yeast strains which have been genetically engineered to express one or more heterologous glycoproteins of interest. The glycosylation on the heterologous glycoproteins expressed from these previously engineered strains can be reduced by transforming such strains with one or more of the vectors of the present invention.

The vectors of the present invention can be introduced into the cells of a methylotrophic yeast strain using known methods such as the spheroplast technique, described by Cregg et al. 1985, or the whole-cell lithium chloride yeast transformation system, Ito et al. *Agric. Biol. Chem.* 48:341, modified for use in *Pichia* as described in EP 312,934. Other published methods useful for transformation of the plasmids or linear vectors include U.S. Pat. No. 4,929,555; Hinnen et al. *Proc. Nat. Acad. Sci. USA* 75:1929 (1978); Ito et al. *J. Bacteria* 153:163 (1983); U.S. Pat. No. 4,879,231; Sreekrishna et al. *Gene* 59:115 (1987). Electroporation and PEG1000 whole cell transformation procedures may also be used. Cregg and Russel *Methods in Molecular Biology: Pichia Protocols*, Chapter 3, Humana Press, Totowa, N.J., pp. 27-39 (1998).

Transformed yeast cells can be selected by using appropriate techniques including but not limited to culturing auxotrophic cells after transformation in the absence of the biochemical product required (due to the cell's auxotrophy), selection for and detection of a new phenotype, or culturing in the presence of an antibiotic which is toxic to the yeast in the absence of a resistance gene contained in the transformants. Transformants can also be selected and/or verified by integration of the expression cassette into the genome, which can be assessed by e.g., Southern Blot or PCR analysis.

In one embodiment, a methylotrophic yeast strain is transformed with a vector which includes a nucleotide sequence coding for an α-1,2-mannosidase or a functional part thereof. The nucleotide sequence is capable of expressing the α-1,2-mannosidase or the functional part in the methylotrophic yeast strain, and is, preferably, integrated into the genome of the methylotrophic yeast strain.

The expression of an α-1,2-mannosidase introduced in a methylotrophic yeast strain can be verified both at the mRNA level, e.g., by Northern Blot analysis, and at the protein level, e.g., by Western Blot analysis. The intracellular localization of the protein can be analyzed by using a variety of techniques, including subcellular fractionation and immunofluorescence experiments. An ER localization of an α-1,2-mannosidase can be determined by co-sedimentation of this enzyme with a known ER resident protein (e.g., Protein Disulfide Isomerase) in a subcellular fractionation experiment. An ER localization can also be determined by an immunofluorescence staining pattern characteristic of ER resident proteins, typically a perinuclear staining pattern.

To confirm that an α-1,2-mannosidase or a functional part thereof expressed in a methylotrophic yeast strain has the expected mannose-trimming activity, both in vitro and in vivo assays can be employed. Typically, an in vitro assay involves digestion of an in vitro synthesized substrate, e.g., $Man_8GlcNAc_2$, with the enzyme expressed and purified from a methylotrophic yeast strain, and assessing the ability of such enzyme to trim $Man_8GlcNAc_2$ to, e.g., $Man_5GlcNAc_2$. In in vivo assays, the α-1,2-mannosidase or a part thereof is co-expressed in a methylotrophic yeast with a glycoprotein known to be glycosylated with N-glycans bearing terminal α-1,2-linked mannose residues in such yeast. The enzymatic activity of such an α-1,2-mannosidase or a part thereof can be measured based on the reduction of the number of α-1,2-linked mannose residues in the structures of the N-glycans of the glycoprotein. In both in vitro and in vivo assays, the composition of a carbohydrate group can be determined using techniques that are well known in the art and are illustrated in the Examples hereinbelow.

In another embodiment, a methylotrophic yeast strain is transformed with a vector which includes a nucleotide sequence coding for a glucosidase II or a functional part thereof. The nucleotide sequence is capable of expressing the glucosidase II or the functional part in the methylotrophic yeast strain, and is, preferably, integrated into the genome of the methylotrophic yeast strain.

The enzymatic activity of a glucosidase II or a functional part thereof expressed in a transformed methylotrophic yeast strain can be assessed using a variety of assays. For example, methylotrophic yeast cells transformed with a sequence encoding a glucosidase II or a part thereof can be set to grow on solid medium containing a substrate of the glucosidase, e.g., 5-bromo-4-chloro-3-indolyl-α-D-glucopyranoside or 4-MU-α-D-Glc. When the enzyme is expressed by the *Pichia* and secreted extracellularly, the substrate is acted upon by the enzyme, giving rise to detectable signals around the colonies such as blue color or fluorescent glow. Alternatively, liquid culture medium containing the expressed protein molecules can be collected and incubated in test tubes with a substrate, e.g., p-nitrophenyl-α-D-glucopyranoside. The enzymatic activity can be determined by measuring the specific product released. Moreover, in vivo assays can be employed, where a glucosidase II is co-expressed in yeast with a glycoprotein known to be N-glycosylated with glucose residues, e.g., influenza neuraminidase. The enzymatic activity of the glucosidase II can be measured based on the reduction of the glucose content in the sugar chain(s) of the glycoprotein.

In still another embodiment of the present invention, a methylotrophic yeast strain is transformed with an Och1 knock-out vector. As a result of the transformation and integration of the vector, the genomic Och1 gene in the yeast strains is disrupted.

In a further embodiment of the present invention, a methylotrophic yeast strain is transformed with any combination of an α-1,2-mannosidase expression vector, a glucosidase II expression vector, and an Och1 knock-out vector. Such modification can be achieved by serial, consecutive transformations, i.e., introducing one vector at a time, or alternatively by co-transformation, i.e., introducing the vectors simultaneously.

The modified methylotrophic yeast strains described herein above can be further modified if desired. For example, additional disruption of genes encoding any other *Pichia* mannosyltransferases can be made. Genes encoding mammalian enzymes can also be introduced to produce glycoproteins having hybrid- or complex-type N-glycans, if desired.

Methylotrophic yeast strains which are modified by using the present methods, i.e., by transforming with one or more of the vectors of the present invention, form another embodiment of the present invention.

It should be understood that certain aspects of the present invention, especially the introduction of an intracellularly expressed α-1,2-mannosidase activity, are also useful to obtain a reduced glycosylation of the O-linked glycans on glycoproteins produced in a methylotrophic yeast, as it is known in the art that these O-linked glycans consist mainly of α-1,2-linked mannose residues. O-linked glycans as used herein refers to carbohydrate structures linked to serine or threonine residues of glycoproteins.

A further aspect of the invention is directed to methods of producing a glycoprotein with reduced glycosylation in a methylotrophic yeast, especially a glycoprotein heterologous to the methylotrophic yeast.

"A glycoprotein" as used herein refers to a protein which, in methylotrophic yeasts, is either glycosylated on one or more asparagines residues or on one or more serine or threonine residues, or on both asparagines and serine or threonine residues.

The term "reduced glycosylation" refers to a reduced size of the carbohydrate moiety on the glycoprotein, particularly with fewer mannose residues, when the glycoprotein is expressed in a methylotrophic yeast strain which has been modified in accordance with the present invention, as compared to a wild type, unmodified strain of the methylotrophic yeast.

In accordance with the present invention, the production of a glycoprotein of interest with reduced glycosylation can be achieved in a number of ways. A nucleotide sequence capable of expressing a glycoprotein can be introduced into a methylotrophic yeast strain which has been previously modified in accordance with the present invention, i.e., a strain transformed with one or more of the vectors of the present invention and capable of producing glycoproteins with reduced glycosylation. Alternatively, a methylotrophic yeast strain which has already been genetically engineered to express a glycoprotein can be transformed with one or more of the vectors of the present invention. Otherwise, if a methylotrophic yeast strain does not express a glycoprotein of interest, nor is the strain transformed with any of the vectors of the present invention, such yeast strain can be transformed, either consecutively or simultaneously, with both a nucleotide sequence capable of expressing the glycoprotein and one or more vectors of the present invention. Additionally, a methylotrophic yeast strain can be transformed with one or more of the present knock-in and/or knock-out vectors which also include a nucleotide sequence capable of expressing a glycoprotein in the methylotrophic yeast strain.

The nucleotide sequence capable of expressing a glycoprotein in a methylotrophic yeast can be made to include from 5' to 3', a promoter, a sequence encoding the glycoprotein, and a 3' termination sequence. Promoters and 3' termination sequences which are suitable for expression of a glycoprotein can include any of those promoters and 3' termination sequences described hereinabove.

The nucleotide sequence for expression of a glycoprotein can include additional sequences, e.g., signal sequences coding for transit peptides when secretion of a protein product is desired. Such sequences are widely known, readily available and include *Saccharomyces cerevisiae* alpha mating factor prepro (αmf), *Pichia pastoris* acid phosphatase (PHO1) signal sequence and the like.

The nucleotide sequence for expression of a glycoprotein can be placed on a replicative vector or an integrative vector. The choice and construction of such vectors are as described hereinabove.

The nucleotide sequence capable of expressing a glycoprotein can be carried on the same replicative plasmid as a plasmid-borne α-1,2-mannosidase or glucosidase II expression unit. Alternatively, the nucleotide sequence containing the glycoprotein coding sequence is carried on a separate plasmid or integrated into the host genome.

Glycoproteins produced can be purified by conventional methods. Purification protocols can be determined by the nature of the specific protein to be purified. Such determination is within the ordinary level of skill in the art. For example, the cell culture medium is separated from the cells and the protein secreted from the cells can be isolated from the medium by routine isolation techniques such as precipitation, immunoadsorption, fractionation or a variety of chromatographic methods.

Glycoproteins which can be produced by the methods of the present invention include, e.g., *Bacillus amyloliquefaciens* α-amylase, *S. cerevisiae* invertase, *Trypanosoma cruzi* trans-sialidase, HIV envelope protein, influenza virus A haemagglutinin, influenza neuraminidase, Bovine herpes virus type-1 glycoprotein D, human angiostatin, human B7-1, B7-2 and B-7 receptor CTLA-4, human tissue factor, growth factors (e.g., platelet-derived growth factor), tissue plasminogen activator, plasminogen activator inhibitor-I, urokinase, human lysosomal proteins such as α-galactosidase, plasminogen, thrombin, factor XIII and immunoglobulins. For additional useful glycoproteins which can be expressed in the genetically engineered *Pichia* strains of the present invention, see Bretthauer and Castellino, *Biotechnol. Appl. Biochem.* 30: 193-200 (1999), and Kukuruzinska et al. *Ann Rev. Biochem.* 56: 915-44 (1987).

Glycoproteins produced by using the methods of the present invention, i.e., glycoproteins with reduced glycosylation, are also part of the present invention.

Still another aspect of the present invention provides kits which contain one or more of the knock-in vectors, knock-out vectors, or knock-in-and-knock-out vectors of the present invention described above. More particularly, a kit of the present invention contains a vector capable of expressing an α-mannosidase I in a methylotrophic yeast, a vector capable of expressing a glucosidase II in a methylotrophic yeast, a vector capable of disrupting the Och1 gene in a methylotrophic yeast, a vector capable of expressing both a glucosidase II and an α-mannosidase, a vector a vector capable of disrupting the Och1 gene and capable of expressing either or both of a glucosidase II and an α-mannosidase, or any combinations thereof.

The kit can also include a nucleotide sequence which encodes and is capable of expressing a heterologous glycoprotein of interest. Such nucleotide sequence can be provided in a separate vector or in the same vector which contains sequences for knocking-in or knocking out as described hereinabove.

In addition, the kit can include a plasmid vector in which a nucleotide sequence encoding a heterologous protein of interest can be subsequently inserted for transformation into and expression in a methylotrophic yeast. Alternatively, the knock-in or knock-out vectors in the kits have convenient cloning sites for insertion of a nucleotide sequence encoding a heterologous protein of interest.

The kit can also include a methylotrophic yeast strain which can be subsequently transformed with any of the knock-in, knock-out or knock-in-and-knock-out vectors described hereinabove. The kit can also include a methylotrophic yeast strain which has been transformed with one or more of the knock-in or knock-out vectors. Furthermore, the kit can include a methylotrophic yeast strain which has been transformed with a nucleotide sequence encoding and capable of expressing a heterologous glycoprotein of interest.

The present invention is further illustrated by the following examples.

EXAMPLE 1

Introduction of α-1,2-Mannosidase to the ER-Golgi Border 1.1 Plasmids

| Plasmid | Promoter | Enzyme | Tag |
|---|---|---|---|
| pGAPZMFManHDEL | GAP | *T. reesei* α-1,2-mannosidase | — |
| pGAPZMFManMycHDEL | GAP | *T. reesei* α-1,2-mannosidase | Myc |
| pPICZBMFManMycHDEL | AOX1 | *T. reesei* α-1,2-mannosidase | Myc |
| pGAPZMFmManHDEL | GAP | mouse mannosidase IB catalytic domain | — |
| pGAPZMFmMycManHDEL | GAP | mouse mannosidase IB catalytic domain | Myc |

The *Trichoderma reesei* α-1,2-mannosidase gene has been isolated and described by Maras et al. (*J. Biotechnol.* 77; 255-263, 2000). The sequence of this gene is available at NCBI Genbank under Accession No. AF212153. A construction fragment was generated by PCR using the pPIC9MFmanase plasmid (same as pPP1MFmds1 described by Maras et al. (2000)) as the template and using the following oligonucleotide primers: 5'-GACTGGTTCCAATTGA-CAAGC-3' (SEQ ID NO: 2) and 5'-AGTCTAGATTA-CAACTCGTCGTGAGCAAGGTGGCCGCCCCG TCG-3' (SEQ ID NO: 3). The resulting product contained the 3' end of the *Pichia pastoris* AOXI promoter, the prepro-signal sequence of the *S. cerevisiae* α-mating factor, the open reading frame of the *Trichoderma reesei* α-1,2-mannosidase cloned in frame with the signal sequence, the coding sequence for HDEL (SEQ ID NO: 1), a stop codon and an Xba I restriction site. This fragment was digested with Eco RI and Xba I, removing the 5' sequences up to the mannosidase ORF, and then cloned into the vector pGAPZαA (Invitrogen, Burn, The Netherlands) which had been digested with Eco RI and Xba I, thus restoring the fusion with the *S. cerevisiae* α-mating factor signal sequence. The resulting plasmid was named pGAPZMFManHDEL and is graphically depicted in FIG. 1. The ORF sequence of the MFManHDEL fusion in pGAPZM-FManHDEL is set forth in SEQ ID NO: 14.

In order to introduce the coding sequence for a c-Myc tag between the catalytic domain and the HDEL-signal (SEQ ID NO: 1), the 3' end of the ORF of *T. reesei* α-1,2-mannosidase was PCR-amplified using a sense primer 5'-CCATTGAG-GACGCATGCCGCGCC-3' (SEQ ID NO: 4) (containing an Sph I restriction site) and an antisense primer GTATCTA-GATTACAACTCGTCGTGCAGATCCTCT-TCTGAGATGAGTTTTTGT TCAGCAAGGTGGCCGC-CCCGTCGTGATGATGAA (SEQ ID NO: 5) (containing the coding sequences of the c-Myc tag and the HDEL (SEQ ID NO: 1) signal, followed by a stop codon and an Xba I restriction site). The resulting PCR product was digested with Sph I and Xba I, purified by agarose gel electrophoresis and inserted into pGAPZMFManHDEL which had been cut with the same restriction enzymes, resulting in plasmid pGAPZM-FManMycHDEL. To put the ORF of pGAPZMFManMycH-DEL under the control of the inducible AOXI promoter, the entire ORF was liberated from pGAPZMFManMycHDEL with Bst BI and Xba I, and cloned in pPICZB (Invitrogen, Baarn, The Netherlands), resulting in pPICZBMFManMycHDEL.

Cloning of the mouse mannosidase IB catalytic domain with concomitant addition of the coding sequence for a C-terminal HDEL-tag (SEQ ID NO: 1) was done by PCR on a mouse cDNA library (mRNA isolated from the L929 cell line induced with cycloheximide and mouse Tumor Necrosis Factor. Average insert length of the cDNA library was 2000 bp). The PCR oligonucleotide primers used were: 5'AACTC-GAGATGGACTCTTCAAAACACAAACGC3' (SEQ ID NO: 6) and 5'TTGCGGCCGCTTACAACTCGTCGT-GTCGGACAGCAGGATTACCTGA3' (SEQ ID NO: 7). The product contained a 5' Xho I site and the coding sequence for C-terminal HDEL-site, followed by a stop codon and a Not I site at the 3' end. The product was cloned in pGAPZαA via the Xho I/Not I sites in the PCR product and the vector, resulting in an in frame fusion of the mouse mannosidase catalytic domain with the *S. cerevisiae* α-mating factor signal sequence. The sequence of the entire open reading frame generated is set forth in SEQ ID NO: 15.

1.2 Yeast Transformation and Genomic Integration

TABLE 2

| Parental strain | DNA transformed |
| --- | --- |
| GS115 (his4) | pGAPZMFManHDEL |
|  | pPIC9MFManHDEL |
|  | pPIC9mManHDEL |
|  | pPIC9mMycManHDEL |
|  | pGAPZmManHDEL |
|  | pGAPZmMycManHDEL |
| GS115 (his4 complemented by pPIC9InfluenzaHA) | pGAPZMFManHDEL |
|  | pGAPZmManHDEL |
|  | pGAPZmMycManHDEL |
| PPY120H (his4 complemented by pPIC9sOCH1) | pGAPZMFManMycHDEL |
|  | pPICZBMFManMycHDEL |
| yGC4 (his4 arg1 ade2 ura3 complemented by pBLURA5'PpOCH1) | pPIC9InfluenzaNeuraminidase |
|  | pGAPZMFManHDEL |
|  | pPIC9Glucoseoxidase |

All transformations to *Pichia pastoris* were performed with electroporation according to the directions of Invitrogen. Transformants of vectors carrying the Zeocin resistance gene were selected on YPD containing 100 µg/ml Zeocine (Invitrogen, Baarn, the Netherlands) and 1M sorbitol. Selection of transformants of pPIC9 derivatives was done on minimal medium lacking histidine and containing 1M sorbitol. Genomic integration of the expression cassettes was verified using PCR on genomic DNA purified from the *Pichia* strains using the Yeast Miniprep method (Nucleon). In all cases concerning the *Trichoderma reesei* gene fusions, the primers used were the sense primer 5'-CCATTGAGGACGCATGC-CGCGCC-3' (SEQ ID NO: 8), which annealed to the 3' half of the mannosidase ORF, and the antisense primer 3' AOXI 5'-GCAAATGGCATTCTGACATCCT-3' (SEQ ID NO: 9), which annealed to the AOXI transcription terminator that was present in all our expression constructs. For the control of genomic integration of the mouse mannosidase transgenes, PCR was done using the sense primer 5'GAP 5'GTC-CCTATTTCAATCAATTGAA3' (SEQ ID NO: 10, annealing to the GAP promoter or 5'AOXI 5'GACTGGTTCCAAT-TGACAAGC3' (SEQ ID NO: 11), annealing to AOXI promoter), and the antisense primer 3'AOXI (above). For the expression constructs containing a Myc tagged *Trichoderma reesei* α-1,2-mannosidase expression unit, further evidence for genomic integration was obtained using Southern Blotting with the entire MFManMycHDEL ORF ($^{32}$P labelled using HighPrime, Boehringer Mannheim) as a probe.

1.3 Expression of α-1,2-mannosidase

Expression of an α-1,2-Mannosidase in GS115 strains expressing influenza virus haemagglutinin was verified by qualitative Northern blot. Expression of an α-1,2-Mannosidase in PPY120H strains was verified by anti-Myc Western blot.

Qualitative Northern Blot—

Total RNA was purified from *Pichia* strains and the yield was determined spectrophotometrically. Northern blotting was performed according to standard procedures and an estimate of the quantity of RNA loaded was made using methylene blue staining of the blot, visualizing the rRNA bands. The blot was probed with a ClaI/NarI fragment of the mannosidase, labelled with $^{32}$P using HighPrime (Boehringer Mannheim).

SDS-PAGE and Western Blotting—

Total yeast cell lysates were prepared by washing the cells twice with PBS, followed by boiling in 1 volume of 2× concentrated Laemmli loading buffer for 5 min. The lysate was spun briefly in a microcentrifuge prior to gel loading and only the supernatant was loaded. For the analysis of proteins secreted into the growth media, the proteins were precipitated from 200 µl of these media using desoxycholate/trichloroacetic acid according to standard procedures. The pellet was redissolved in 2× concentrated Laemmli loading buffer and the solutions were pH-corrected using Tris. SDS-PAGE was performed and followed by semidry electroblotting to nitrocellulose membranes. For Western Blotting, the 9E10 anti-Myc and the anti-HA mouse monoclonals (Boehringer Mannheim) were used at a concentration of 1 µg/ml, and the rabbit anti-PDI antiserum (Stressgen) was used at a dilution of 1/500. The secondary antibodies were goat anti-mouse IgG conjugated to alkaline phosphatase for the monoclonals and goat anti-rabbit IgG conjugated to peroxidase for the polyclonal (secondary antibodies from Sigma). Detection was performed using the NBT/BCIP system for alkaline phosphatase and the Renaissance substrate (NENBiosciences) for peroxidase. Imaging of the latter blot result was done on a Lumilager imaging device (Boehringer Mannheim).

Figure 4:
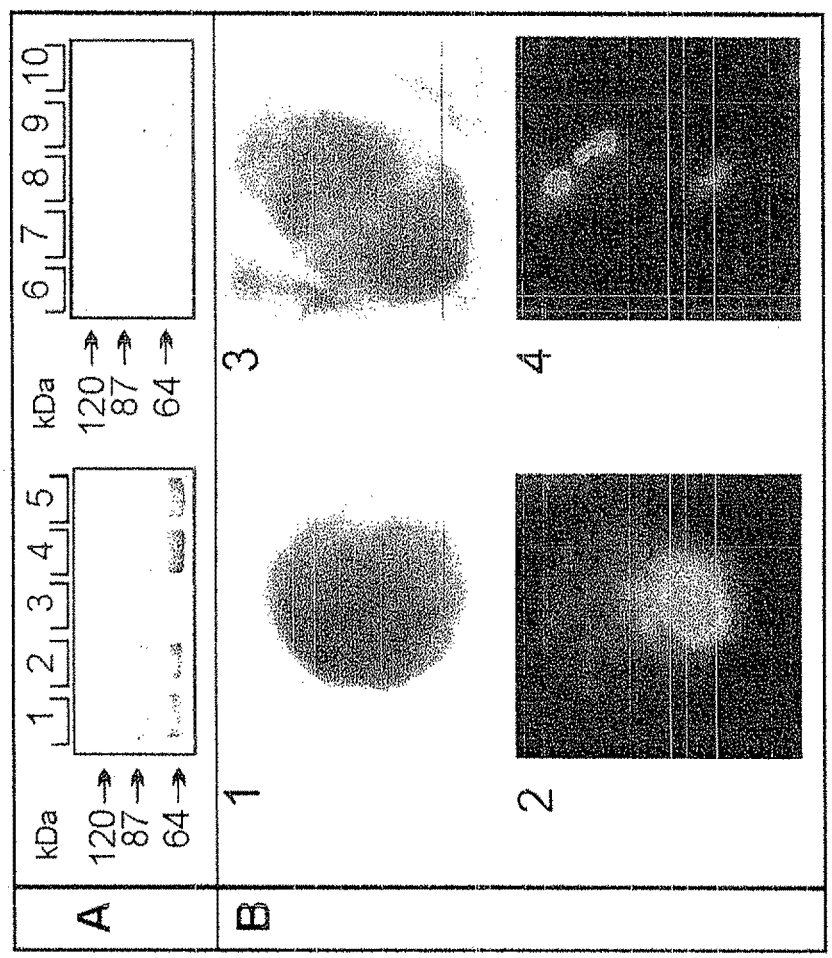
FIG. 4 demonstrates the intracellular localization of the MycHDEL-tagged *Trichoderma reesei* α-1,2-mannosidase and indicates ER-targeting by immunofluorescence analysis. Panel A Western blotting. Yeast strains were grown in 10 ml YPG cultures to an $OD_{600}$=10, diluted fivefold and grown in YPM for 48 h. 1/50th of the culture medium and 1/65th of the cells were analysed by SDS-PAGE and Western blotting with the mouse monoclonal 9E10 anti-Myc antibody. The position of molecular weight marker proteins are indicated with arrows. Lanes 1-5: cellular lysates. 1,2: pGAPZMFManMycHDEL transformants. 3: non-transformed PPY120H (negative control). 4,5: pPICZBMFManMycHDEL transformants. Lanes 6-10: culture media. 6: non transformed PPY120H (negative control). 7,8: pGAPZMFManMycHDEL transformants. 9,10: pPICZBMFManMycHDEL transformants. Panel B Immunofluorescence microscopy. 1: phase contrast image of a *P. pastoris* cell (strain PPY120H transformed with pGAPZMFManHDEL) at 1000× magnification. The nucleus is visible as an ellipse in the lower right quadrant of the cell. 2: same cell as in 1, but in fluorescence microscopy mode to show localization of the *T. reesei* mannosidase-Myc-HDEL protein. The protein is mainly localized in a circular distribution around the nucleus (nuclear envelope), which is typical for an endoplasmic reticulum steady-state distribution. 3: phase contrast image of a *P. pastoris* cell (strain PPY12OH transformed with pGAPZMFManHDEL) at 1000× magnification. 4: same cell in fluorescence microscopy to show localization of the Golgi marker protein OCH1-HA in *P. pastoris* strain PPY12OH. The dot-like distribution throughout the cytoplasm, with 3-4 dots per cell is typical for cis-Golgi distribution in *P. pastoris*.

The results shown in FIG. 4 indicated that the great majority of the HDEL (SEQ ID NO: 1)-tagged protein was retained intracellularly, both when expressed from the strong constitutive GAP promoter and when expressed from the strong inducible AOXI promoter.

1.4 Localization of α-1,2-mannosidase

Isopycnic sucrose density gradient centrifugation—To determine the localization of the HDEL (SEQ ID NO: 1)-tagged mannosidase, subcellular fractionation was carried out using cells expressing the mannosidase-Myc-HDEL from the strong constitutive GAP promoter.

Briefly, 0.5 g of wet weight yeast cells were lysed using 4×1 min vortexing with 4.5 g glass beads in 1 ml lysis-buffer (50 mM Tris-HCL pH 7.5 containing 0.6 M sorbitol, 10 mM β-mercaptoethanol and 5 mM MgCl$_2$). Between vortexing periods, the mixture was placed on ice for 5 min, The supernatant was collected and the glass beads were washed once with lysis-buffer, and the supernatant of this washing step was added to the first supernatant. This lysate was subjected to a differential centrifugation procedure. The P10000 pellet was solubilized in 0.5 ml of a 60% sucrose solution in lysis buffer. This solution was placed at the bottom of an Ultraclear ultracentrifuge tube (Beckman) of 14×89 mm. Subsequently, 1.5 ml each of sucrose solutions of 55, 50, 45, 42.5, 40, and 37.5% were carefully layered over each other. The tube was filled to the edge with 35% sucrose. Isopycnic sucrose gradient centrifugation was performed for 14 h at 180,000 g in a Beckman SW 41 rotor in a Beckman Model L8-70 preparative ultracentrifuge. After completion, 1 ml fractions were collected from the top and partially dialysed from excess sucrose, evaporated to dryness in a vacuum centrifuge. After redissolving the pellet in Laemmli buffer, the samples were subjected to SDS-PAGE in triplicate and the Western blots were treated with anti-HA, anti-Myc or anti-PDI ("PDI" for Protein Disulfide Isomerase), respectively.

Figure 5:
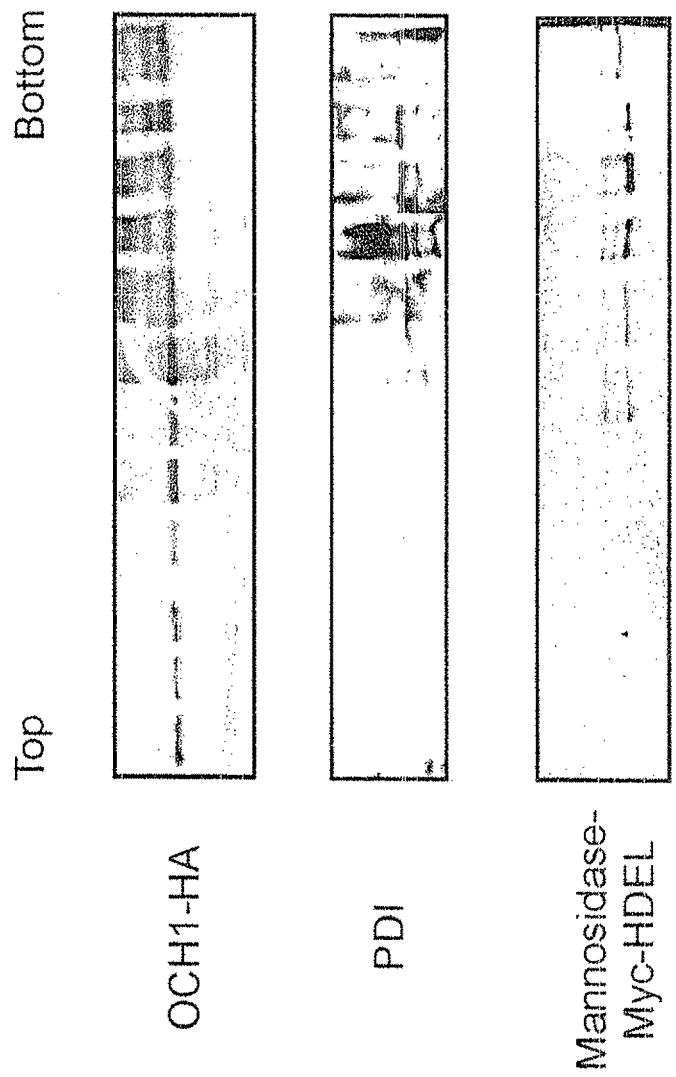
FIG. 5 depicts the co-sedimentation of mannosidase-MycHDEL with Protein Disulfide Isomerase in sucrose density gradient centrifugation. The top panel shows the distribution over the different fractions of the sucrose gradient of the OCH1-HA Golgi marker protein. The middle panel shows this distribution for the Protein Disulfide Isomerase endoplasmic reticulum marker protein. Finally, the bottom panel shows the distribution of the MycHDEL-tagged *Trichoderma reesei* α-1,2-mannosidase over the same fractions. It is concluded that the mannosidase-MycHDEL almost exactly matches the distribution of the ER marker PDI and thus mainly resides in the ER of the *Pichia pastoris* yeast cells.

The results illustrated almost exact cosedimentation of the MFManMycHDEL protein with the Protein Disulfide Isomerase marker protein (which is also targeted with a HDEL (SEQ ID NO: 1) signal sequence) (FIG. 5). In the same assay, the HA-tagged OCH1 was distributed over the whole gradient, with the highest abundance in fractions having a density lower than that of the fractions containing the mannosidase and the PDI. This result indicated that the mannosidase was targeted to the expected location (the ER-Golgi boundary) by the addition of an HDEL (SEQ ID NO: 1) signal. In contrast, the mannosidase without HDEL (SEQ ID NO: 1), expressed from inducible alcohol oxidase I promoter (which was of comparable strength as the GAP promoter), was secreted at a high level of about 20 mg/l.

Immunofluorescence microscopy—To confirm the correct targeting of the mannosidase-Myc-HDEL, an immunofluorescence microscopy experiment was performed.

Briefly, yeast cultures were grown to OD$_{600}$ in YPD (for pGAPZMFManMycHDEL) or in YMP following a YPGlycerol growth phase for pPICZBMFManMycHDEL. Formaldehyde was added to the yeast cultures to a final concentration of 4% and incubated for 10 min at room temperature. Cells were pelleted and resuspended in 50 mM potassium phosphate buffer pH 6.5 containing 1 mM MgCl$_2$ and 4% formaldehyde and incubated for 2 h at room temperature. After pelleting, the cells were resuspended to an OD$_{600}$=10 in 100 mM potassium phosphate buffer pH 7.5 containing 1 mM MgCl$_2$ and EDTA-free Complete™ protease inhibitor cocktail (Boehringer Mannheim). To 100 μl of cell suspension, 0.6 μl of β-mercapto-ethanol and 20 μl of 20,000 U/ml Zymolyase 100T (ICN) were added, followed by a 25 minute incubation with gentle shaking. The cells were washed twice in the incubation buffer and added to poly-lysine coated cover slips (these are prepared using adhesive rings normally in use for reinforcing perforations in paper). Excess liquid was blotted with a cotton swab and the cells were allowed to dry at 20° C. All blocking, antibody incubation and washing steps are performed in PBS containing 0.05% bovine serum albumin. Primary antibodies are used at 2 μg/μl and secondary antibodies conjugated to flurophores (Molecular probes) were used at 5 μg/μl. The nucleus was stained with the nucleic acid stain HOECHST 33258. After fixation and cell wall permeabilization, the integrity of the yeast cell morphology was checked in phase contrast microscopy and after immunostaining, the slides were examined under a Zeiss Axiophot fluororesensce microscope equipped with a Kodak digital camera. Images were processed using Macprobe 4.0 software and prepared with Corel Photopaint 9.0.

The Golgi marker protein OCH1-HA gave the typical Golgi staining pattern described in the literature (speckle-like staining). Staining with the 9E10 monoclonal anti-Myc antibody, recognizing mannosidase-Myc-HDEL, gave a perinuclear staining pattern with some disparate staining in the cytoplasm, highly indicative for an ER targeting (FIG. 4).

Based on the foregoing experiments, it is concluded that the *Trichoderma reesei* mannosidase-Myc-HDEL was targeted to the ER-Golgi boundary.

EXAMPLE 2

Co-Expression of Mannosidase-HDEL with Recombinant Glycoproteins

Co-Expression of Mannosidase-HDEL with the *Trypanosoma cruzi* Trans-Sialidase

The cloning of a *Trypanosoma cruzi* trans-sialidase gene coding for an active trans-sialidase member without the C-terminal repeat domain has been described by Laroy et al. (*Protein Expression and Purification* 20: 389, 2000) which is incorporated herein by reference. The sequence of this *Trypanosoma cruzi* trans-sialidase gene is available through NCBI Genbank under the Accession No. AJ276679. For expression in *P. pastoris*, the entire gene was cloned in pHILD2 (Invitrogen, San Diego, Calif.), creating pHILD2-TS. To allow better secretion, pPIC9-TS was created in which trans-sialidase was linked to the prepro secretion signal of the yeast α-mating factor. Plasmids pPIC9-TSE and pCAGGS-prepro-TSE were created where the epitope E-tag was added to the C-terminal of the trans-sialidase to allow easy detection and purification. The construction of pHILD2-TS, pPIC9-TSE and pCAGGS-prepro-TSE has been described by Laroy et al. (2000), incorporated herein by reference. The vectors used in the construction were made available through for pCAGGS (No. LMBP 2453), Invitrogen, San Diego, Calif. for pHILD2 and pPIC9, and Pharmacia Biotech for pCANTAB-5E.

Plasmid pPIC9-TSE was linearized with SstI and was transformed into *P. pastoris* GS115 (his4) strain by electroporation according to the manufacturer's instructions (Invitrogen). One of the transformants was further transformed with plasmid pGAPZMFManHDEL, establishing a strain co-expressing Mannosidase-HDEL and the *Trypanosoma cruzi* trans-sialidase.

Fermentation and protein purification was according to the procedures described by Laroy et al. (2000).

Purified trans-sialidase was subject to carbohydrate analysis according to Callewaert et al., *Glycobiology* 11, 4, 275-281, 2001. Briefly, the glycoproteins were bound to the PVDF membrane in the wells of a 96-well plate, reduced, alkylated and submitted to peptide-N-glycosidase F deglycosylation. The glycans were derivatised with 8-amino-1,3,6-pyrenetrisulfonic acid by reductive amination. Subsequently, the excess free label was removed using Sephadex G10-packed spin columns and the glycans were analysed by electrophoresis on a 36 cm sequencing gel on an ABI 377A DNA-sequencer and detected using the built-in argon laser. Digests with 3 mU/ml purified *T. reesei* α-1,2-mannosidase (described by Maras et al., *J. Biotechnol.* 77, 255-63, 2000) were also performed in 20 mM sodium acetate pH-5.0. The glycans derived from 1 μg of the purified recombinant glycoproteins were used as the substrate. 1 U of the α-1,2-mannosidase is defined as the amount of enzyme that releases 1 µmol of mannose from baker's yeast mannan per minute at 37° C. and pH-5.0.

Figure 6:
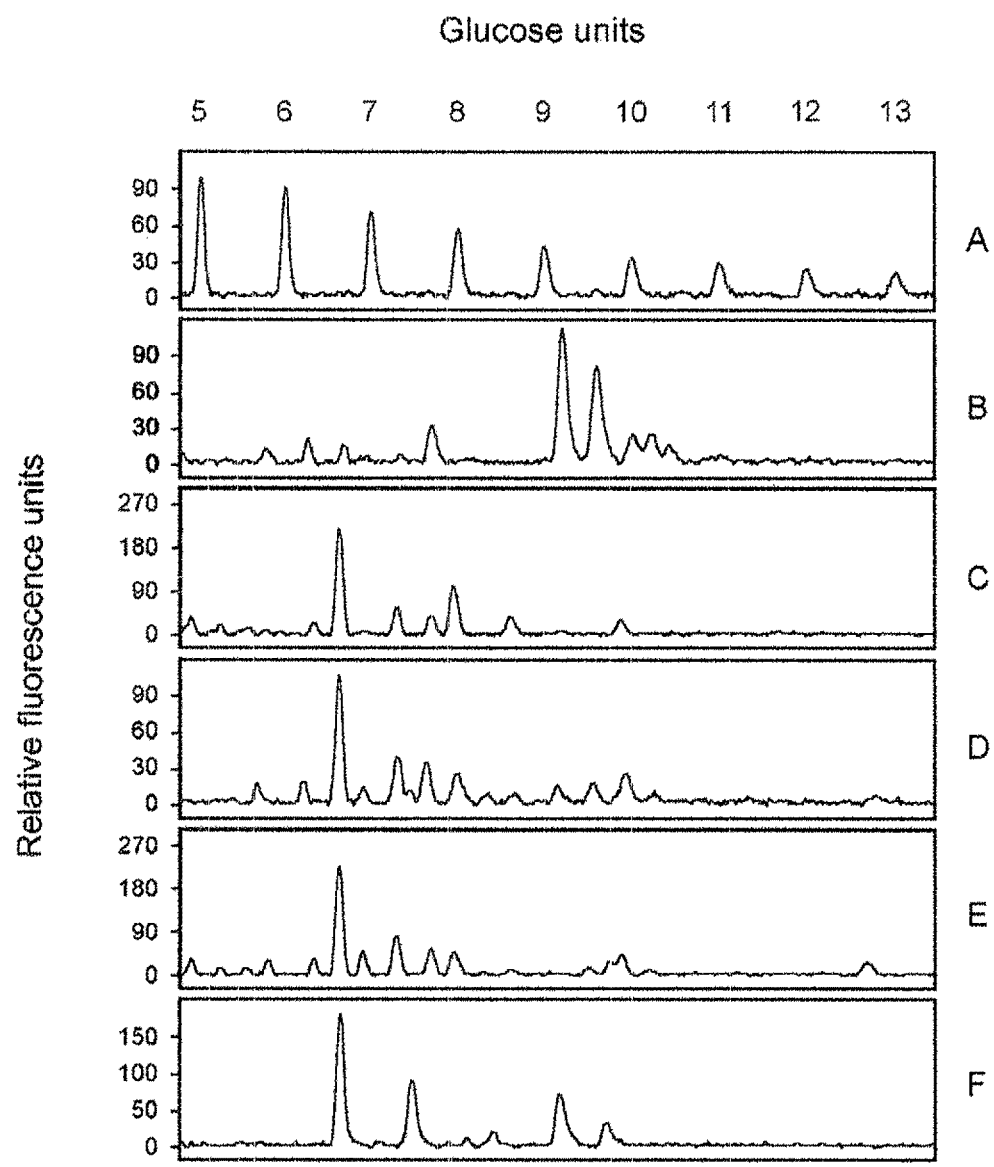
FIG. 6 depicts the N-glycan analysis of *Trypanosoma cruzi* trans-sialidase coexpressed with *Trichoderma reesei* mannosidase-HDEL. Panel A: malto-oligosaccharide size reference ladder. Sizes of the glycans are expressed in Glucose Units (GU) by comparison of their electrophoretic mobility to the mobility of these malto-oligosaccharides. Panel B: N-glycans derived from recombinant *Trypanosoma cruzi* trans-sialidase expressed in *Pichia pastoris*. The peak at GU=9, 2 corresponds to $Man_8GlcNAc_2$. Panel C: same analytes as panel 2, but after overnight treatment with 3 U/ml purified recombinant *T. reesei* α-1,2-mannosidase. Panel D: N-glycans derived from recombinant trans-sialidase co-expressed in *Pichia pastoris* with *T. reesei* mannosidase-HDEL (under control of the GAP promotor). The peak at GU=7, 6 corresponds to the $Man_5GlcNAc_2$ peak in the profile of RNase B (Panel F). Panel E: same analytes as panel D, but after overnight treatment with 3 mU/ml purified recombinant *T. reesei* α-1,2-mannosidase. Panel F: N-glycans derived from bovine RNase B. These glycans consist of $Man_5GlcNAc_2$ to $Man_8GlcNAc_2$. Different isomers are resolved, accounting for the number of peaks for $Man_7GlcNAc_2$.

As can be seen in FIG. 6, panel B, the major N-glycan on trans-sialidase was $Man_8GlcNAc_2$ (Compare with panel F, representing an analysis of the N-glycans of bovine RNAseB. The one but last peak in this profile is $Man_8GlcNAc_2$, the first peak is $Man_5GlcNAc_2$). In vitro, this glycan was digestible to $Man_5GlcNAc_2$ with α-1,2-mannosidase (FIG. 6, panel C). In the N-glycan profile of the trans-sialidase co-expressed with mannosidase-HDEL, the major peak corresponded to $Man_5GlcNAc_2$ (FIG. 6, panel D).

Co-Expression of Mannosidase-HDEL with the Influenza A Virus Haemagglutinin

The Influenza A virus haemagglutinin was known to be glycosylated in *Pichia pastoris* with high-mannose N-glycans containing 9-12 mannose residues (Saelens et al. *Eur. J. Biochem.* 260: 166-175, 1999). The effect of a co-expressed mannosidase on the N-glycans of the haemagglutinin was assessed in an N-glycan profiling method described below. In addition, to compare the efficiency of the *Trichoderma* enzyme (having a temperature optimum of 60° C.) with a mammalian mannosidase having a temperature optimum of 37° C., the catalytic domain of the mouse mannosidase IB from a mouse cDNA-library was cloned and tagged with a HDEL signal by PCR amplification. This ORF was cloned after the prepro-signal sequence of the *S. cerevisiae* α-mating factor under the control of the GAP promoter. Expression of the mannosidase-HDEL transgenes on the mRNA level was confirmed by qualitative Northern blotting.

The haemagglutinin was expressed and purified from a non-mannosidase expressing control strain and from a strains co-expressing the *Trichoderma reesei* mannosidase-HDEL or the mouse mannosidase IB-HDEL according to the procedure described by Kulakosky et al. *Glycobiology* 8: 741-745 (1998). The purified haemagglutin was subjected to PNGase F digestion as described by Saelens et al. *Eur. J. Biochem.* 260: 166-175, 1999. The proteins and glycans were precipitated with 3 volumes of ice-cold acetone and the glycans were extracted from the pellet with 60% methanol. Following vacuum evaporation, the glycans were labeled with 8-amino-1,3,6 pyrenetrisulfonic acid by adding 1 µl of a 1:1 mixture of 20 mM APTS in 1.2M citric acid and 1M $N_aCNBH_3$ in DMSO and incubating for 16 h at 37° C. at the bottom of a 250 µl PCR-tube, The reaction was stopped by the addition of 10 µl deionized water and the mixture was loaded on a 1.2 cm Sephadex G10 bed packed to dryness in a microspin-column by centrifugation in a swinging bucket rotor, which provided for a flat resin surface. After loading, 50 µl deionised water was carefully added to the resin bed and the spin column was briefly centrifuged for 5 seconds at 750 g in a tabletop centrifuge. This elution process was repeated twice and all the eluates were pooled and evaporated to dryness in a Speedvac vacuum centrifuge (Savant). The labeled glycans were reconstituted in 1.5 µl gel loading buffer containing 50% formamide and 0.5 µl Genescan 500™, labeled with rhodamine (Perkin Elmer Bioscience), serving as an internal reference standard. This mixture was loaded on a DNA-sequencing gel containing 10% of a 19:1 mixture of acrylamide:bisacrylamide (Biorad, Hercules, Calif., USA) and made up in the standard DNA-sequencing buffer (89 mM Tris, 89 mM borate, 2.2 mM EDTA). Polymerization of the gel was catalyzed by the addition of 200 µl 10% ammononiumpersulfate solution in water and 20 µl TEMED. The gel was of the standard 36 cm well-to-read length and was run on an Applied Biosystems Model 373A DNA-sequencing apparatus. Pre-running of the gel was done at 1000 V for 15 min. and after loading, the gel was electrophoresed for 8 h at 1250 V without heating. This methodology gives a limit of detection of 10 fmol per peak. The data were analysed with Genescan 3.0 software.

Figure 7:
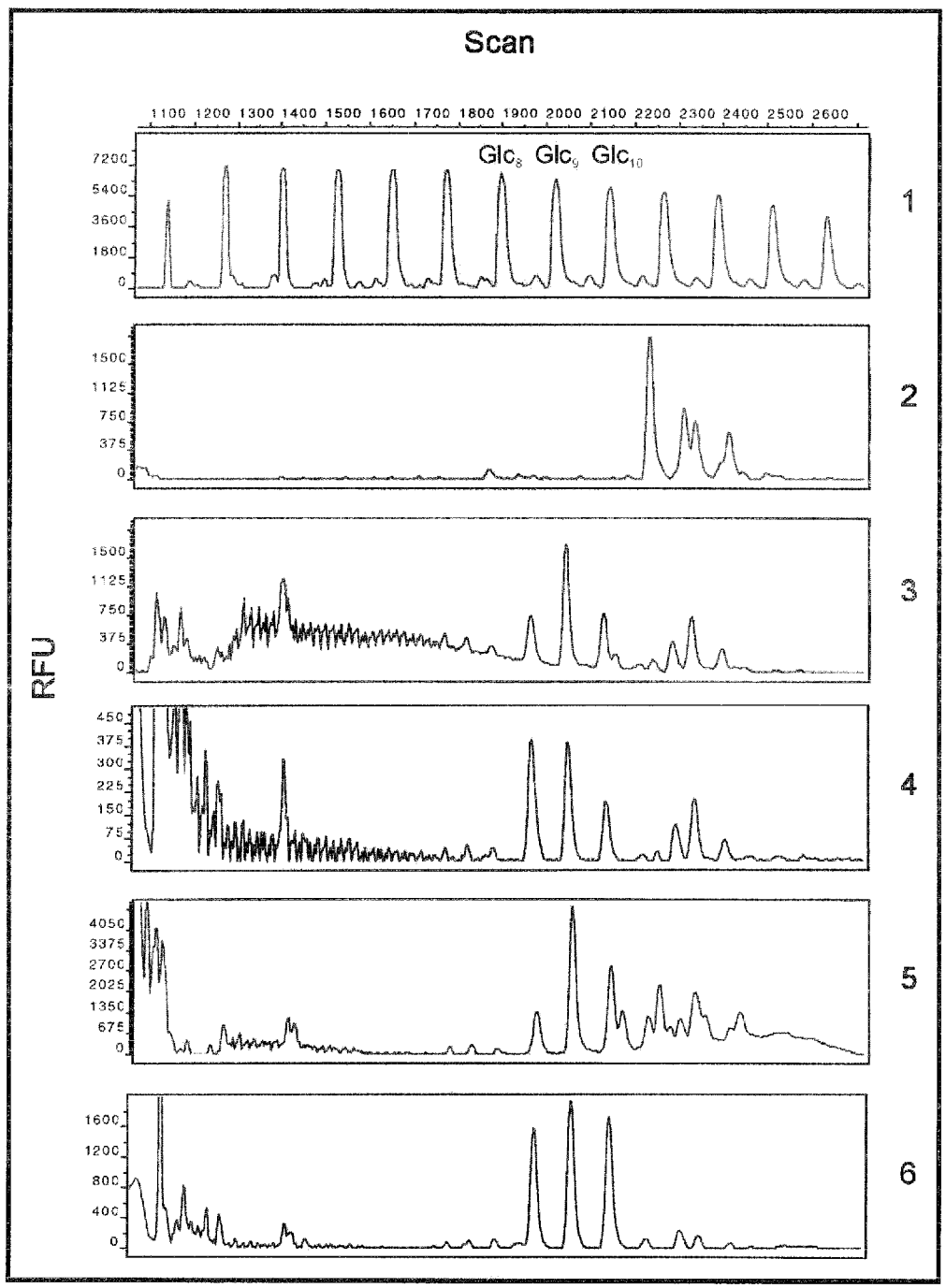
FIG. 7 depicts the processing of influenza haemagglutinin N-glycans by HDEL (SEQ ID NO: 1)-tagged *Trichoderma reesei* α-1,2-mannosidase and the HDEL (SEQ ID NO: 1)-tagged catalytic domain of murine α-1,2-mannosidase IB. The $Man_5GlcNAc_2$ reference oligosaccharide runs at scan 1850 in this analysis (not shown). Panel 1: malto-oligosaccharide size reference ladder. Panel 2: N-glycans derived from recombinant influenza haemagglutinin expressed in *Pichia pastoris*. The peak at scan 2250 corresponds to $Man_9GlcNAc_2$. Panel 3: N-glycans derived from recombinant haemagglutinin co-expressed in *Pichia pastoris* with *T. reesei* mannosidase-HDEL (under control of the GAP promotor). The peak at scan 1950 corresponds to $Man_6GlcNAc_2$. Panel 4: Same analytes as for panel 3, but after overnight treatment with 30 mU purified recombinant *T. reesei* α-1,2-mannosidase. Panel 5: N-glycans derived from recombinant haemagglutinin co-expressed in *Pichia pastoris* with mouse mannosidase IB-HDEL (under control of the GAP promotor). Panel 6: same analytes as for panel 5, but after overnight treatment with 30 mU purified recombinant *T. reesei* α-1,2-mannosidase.

As shown in FIG. 7, the *Trichoderma reesei* α-1,2-mannosidase provided the most complete reduction in the number of α-1,2-mannoses present on the N-glycans. The N-glycan processing by mouse mannosidase IB-HDEL was less efficient than by the *Trichoderma reesei* α-1,2-mannosidase.

Despite the efficient removal of α-1,2-mannoses from the N-glycans of haemagglutinin, no $Man_5GlcNAc_2$ was obtained. Even after digestion of the N-glycans with 3 mU of purified *Trichoderma reesei* α-1,2-mannosidase, only $Man_6GlcNAc_2$ was obtained as the smallest sugar chain. These results indicated that the remaining residues were possibly α-1,6-linked mannoses, originating from the initiating OCH1 α-1,6-mannosyltransferase enzymatic activities. OCH1 was observed to be localized to very early part of the Golgi apparatus and could act on the N-glycans of haemagglutinin before complete digestion of the $Man_8GlcNAc_2$ precursor to $Man_5GlcNAc_2$ by the mannosidases-HDEL. Thus, for proteins whose glycans are efficiently modified by the α-1,6-mannosyltransferase, an inactivation of the OCH1 gene coding for the transferase would be desirable in order to obtain proteins with $Man_5GlcNAc_2$.

EXAMPLE 3

Inactivation of the *Pichia* Och1 Gene

A *Pichia pastoris* sequence was found in the GenBank under Accession No. E12456 and was described in Japanese Patent Application No. 07145005, incorporated herein by reference. This sequence shows all typical features of an α-1,6-mannosyltransferase and is most homologous to the *S. cerevisiae* OCH1, thus referred to herein as the *Pichia pastoris* Och1 gene.

Figure 8:
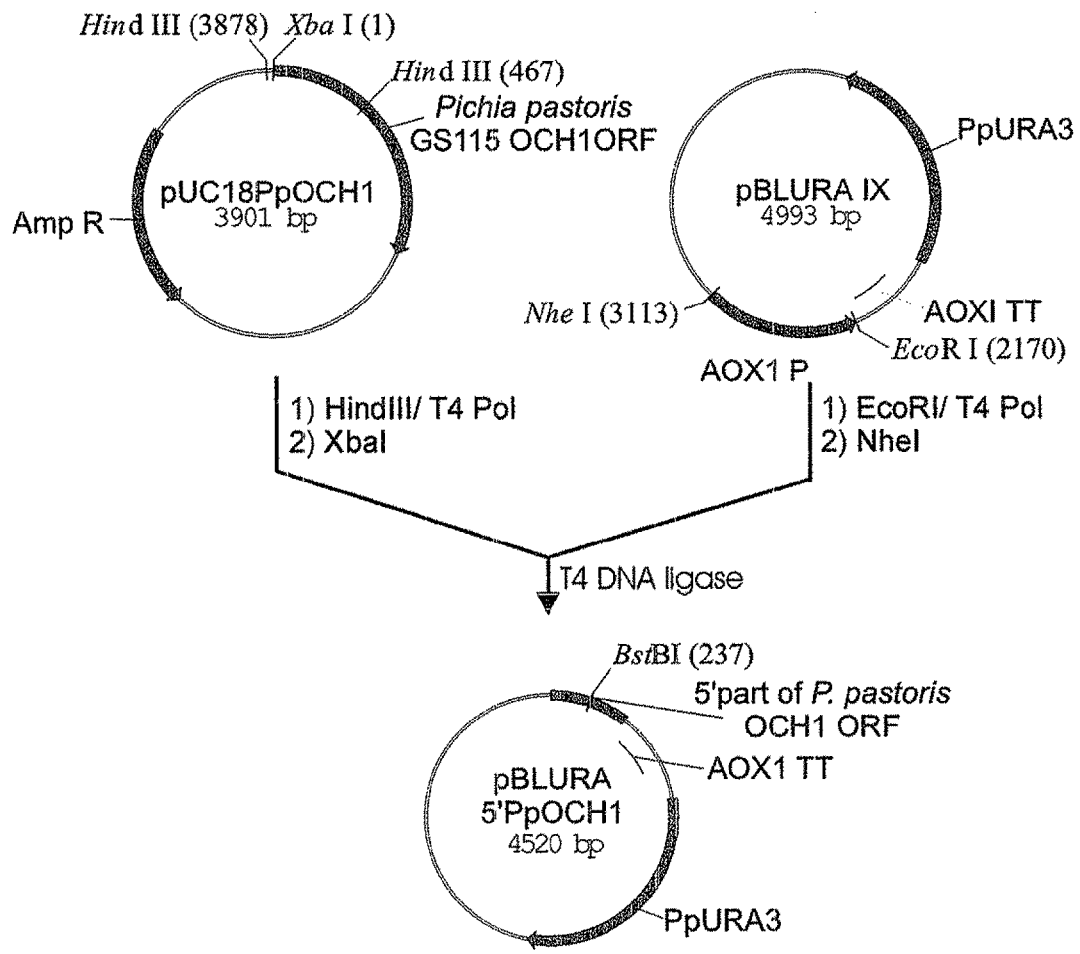
FIG. 8 graphically depicts vector pBLURA5'PpOCH1 and the way in which it was constructed.

First, the full ORF of the *Pichia pastoris* Och1 gene was PCR cloned in pUC18 to obtain plasmid pUC18pOch1. pUC18pOch1 was cut with HindIII, blunt-ended with T4 polymerase, then cut with XbaI, releasing a fragment containing the 5' part of the *Pichia pastoris* Och1 gene. This fragment was ligated into the vector pBLURA IX (available from the Keck Graduate Institute, Dr. James Cregg, which had been cut with Eco RI, blunt-ended with T4 polymerase, and then cut with Nhe I. This ligation generated pBLURA5'PpPCHI, as shown in FIG. 8.

Figure 9:
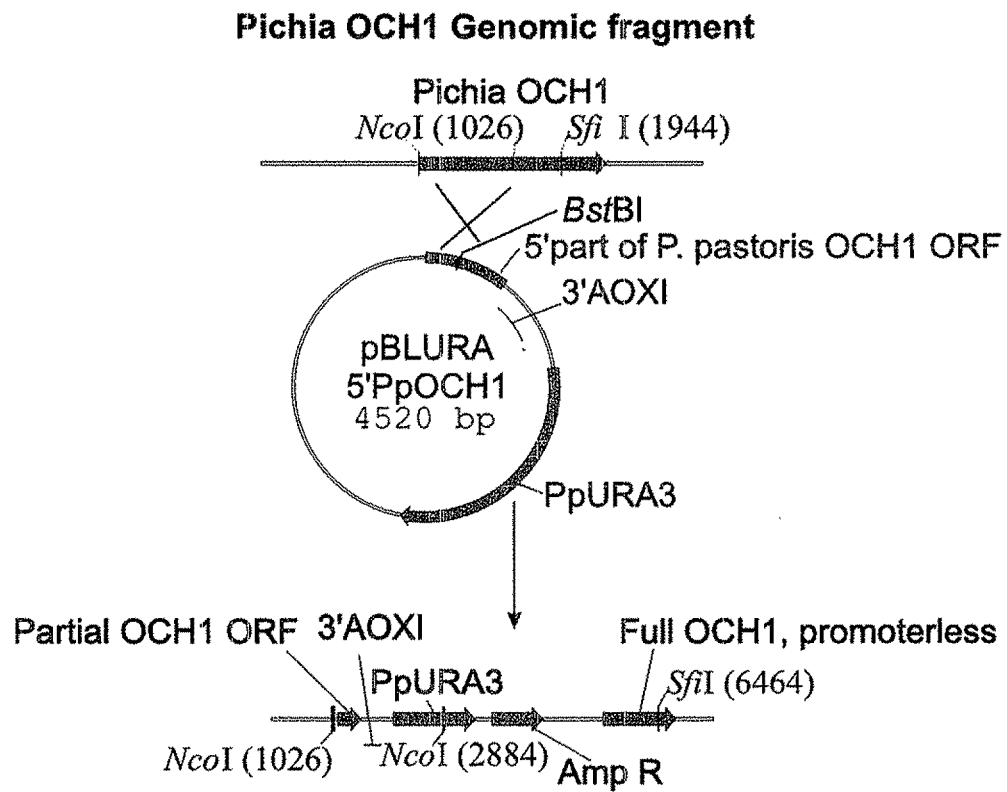
FIG. 9 depicts the scheme for disrupting the *Pichia pastoris* OCH1 gene by single homologous recombination using pBLURA5'PpOCH1.

Disruption of this *Pichia* OCH1 gene in the *Pichia* genome was achieved by single homologous recombination using pBLURA5'PpOCH1, as illustrated in FIG. 9. As a result of the single homologous recombination, the Och1 gene on the *Pichia* chromosome was replaced with two Och1 sequences: one consisted only about the first one third of the full Och1 ORF, the other had a full Och1 ORF without a Och1 promoter. Single homologous recombination was achieved as follows. Cells of the *Pichia* strain yGC4 were transformed by electroporation with pBLURA5'PpOCH1 which had been linearized with the single cutter Bst BI. About 500 transformants were obtained on minimal medium containing 1M sorbitol, biotin, arginine, adenine and histidine and incubation at 27° C. Thirty-two of these transformants were picked and re-selected under the same conditions. Twelve clones were further analyzed for correct genomic integration of the cassette by PCR. Seven of the twelve URA prototrophic clones contained the cassette in the correct locus.

Figure 10:
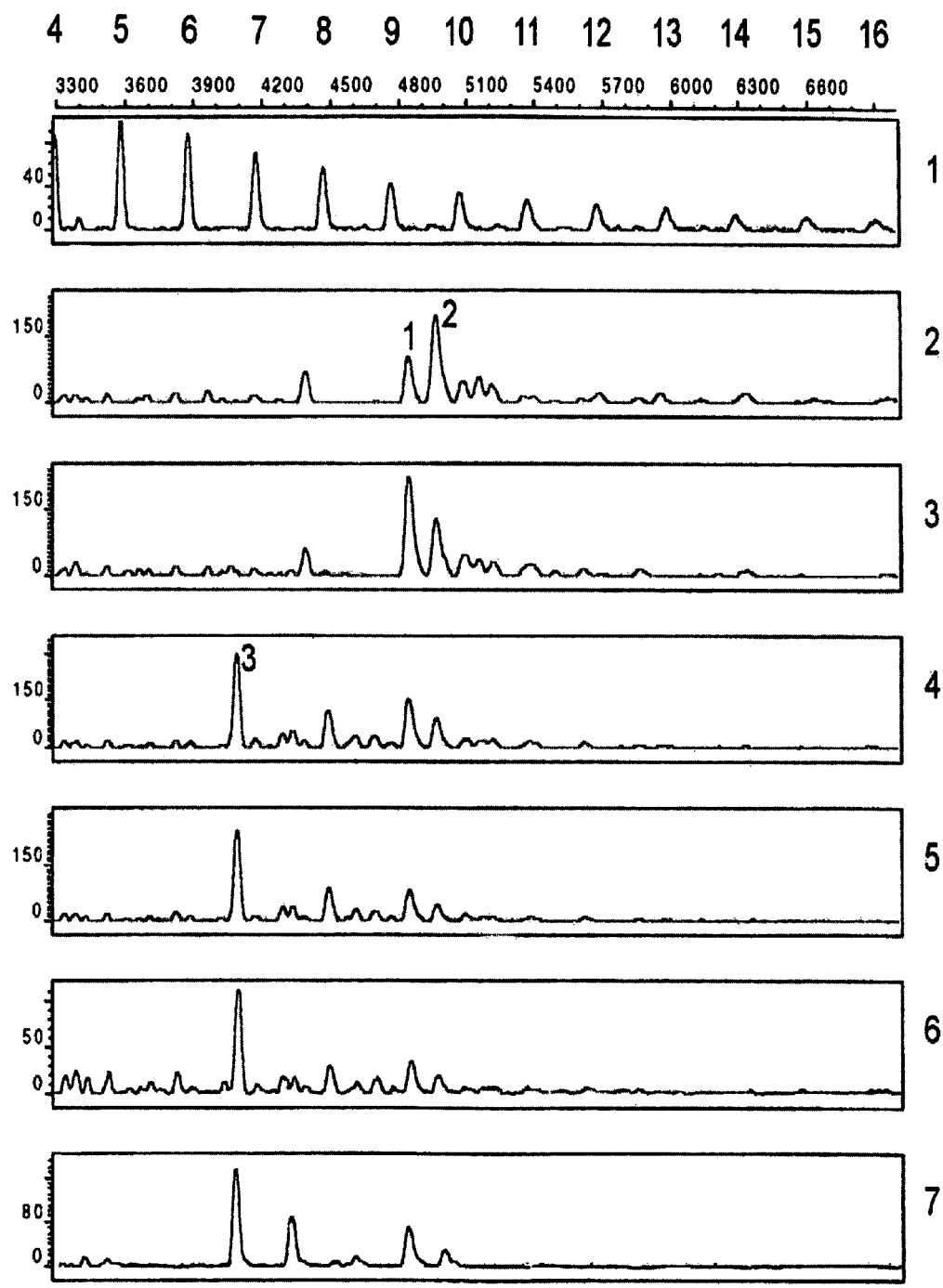
FIG. 10 depicts the cell wall glycoprotein N-glycan analysis of the Och1-inactivated clone and three clones derived from this Och1-inactivated clone by transformation with pGAPZMFManHDEL. Panel 1 shows the analysis of a mixture of malto-oligosaccharides, the degree of polymerisation of which is given by the numbers on the very top of the figure. This analysis serves as a size reference for the other panels. On the vertical axis of all panels, peak intensity in relative fluorescence units is given. Panel 2-6: analysis of the cell wall glycoprotein N-glycans of the following strains: Panel 2, non-engineered *P. pastoris* strain yGC4; Panel 3, yGC4 transformed with pBLURA5'PpOch1; 4-6, three clones of the strain of Panel 3, supplementarily transformed with pGAPZMFManHDEL. Panel 7: the N-glycans derived from bovine RNaseB, consisting of a mixture of $Man_{5-9}GlcNAc_2$. As can be seen from comparison between panel 2 and 3 and reference to panel 7, transformation with pBLURA5'PpOch1 leads to a strongly increased abundance of the $Man_8GlcNAc_2$ substrate N-glycan (named peak 1 in Panel 2) of OCH1p. Peak 2 represents the $Man_9GlcNAc_2$ product of OCH1p. Furthermore, upon supplementary transformation of pGAPZMFManHDEL, the major glycan on the cell wall glycoproteins of three independent clones is the $Man_5GlcNAc_2$ end product (peak 3 in panel 4) of *T. reesei* α-1,2-mannosidase digestion of the $Man_8GlcNAc_2$ substrate.
Figure 11:
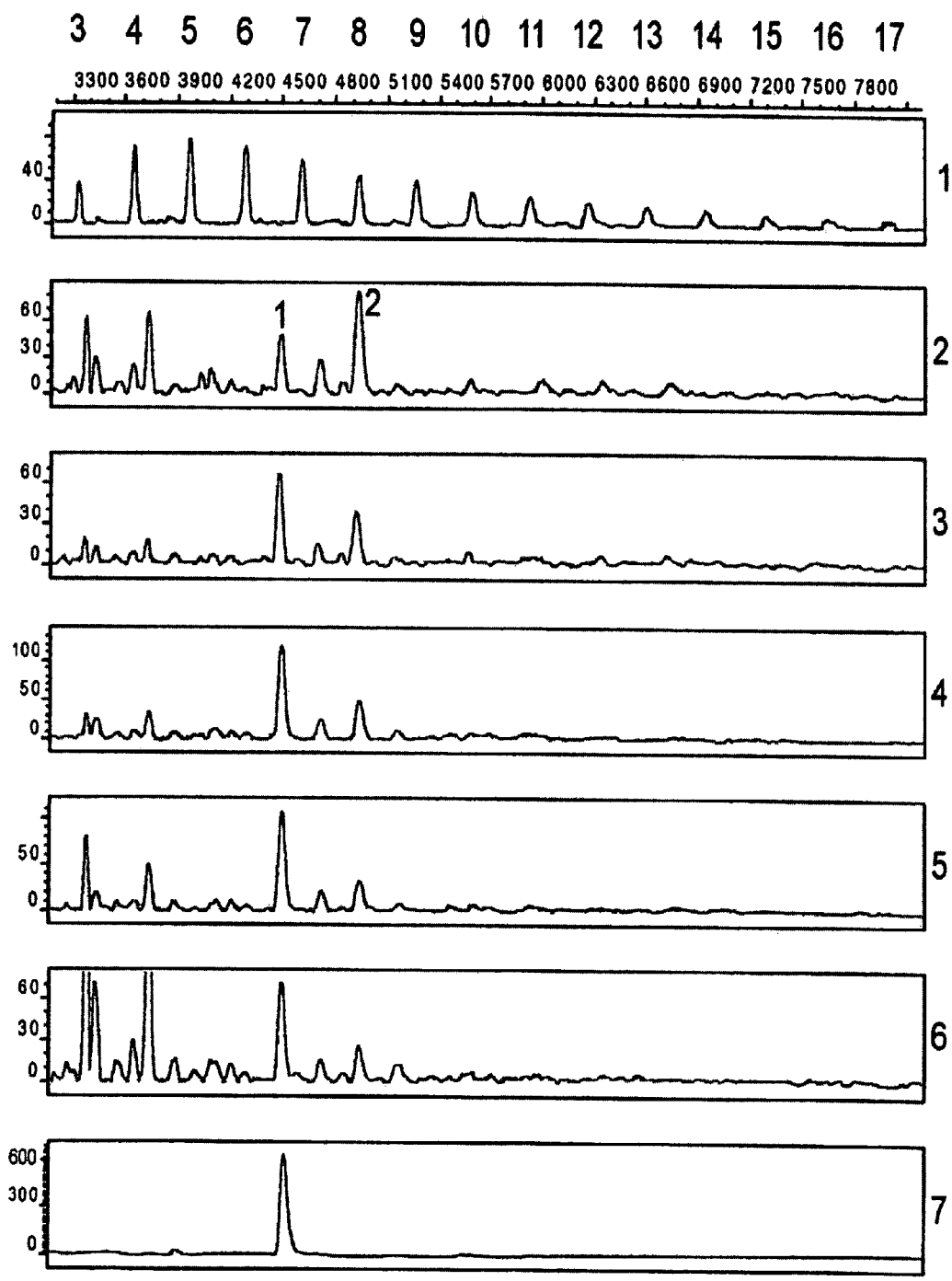
FIG. 11 depicts the analysis of exactly the same glycan mixtures as in FIG. 10, but after an in vitro digest with 3 mU/ml purified *Trichoderma reesei* α-1,2-mannosidase, overnight in 20 mM sodium acetate pH=5.0. Axis assignment is the same as in FIG. 10. More $Man_5GlcNAc_2$ is formed in the pBLURA5'PpOch1 transformed strain (Panel 3) than in the parent strain (Panel 2). Peaks in all panels before scan 3900 come from contaminants and should be ignored in the analysis.
Figure 12:
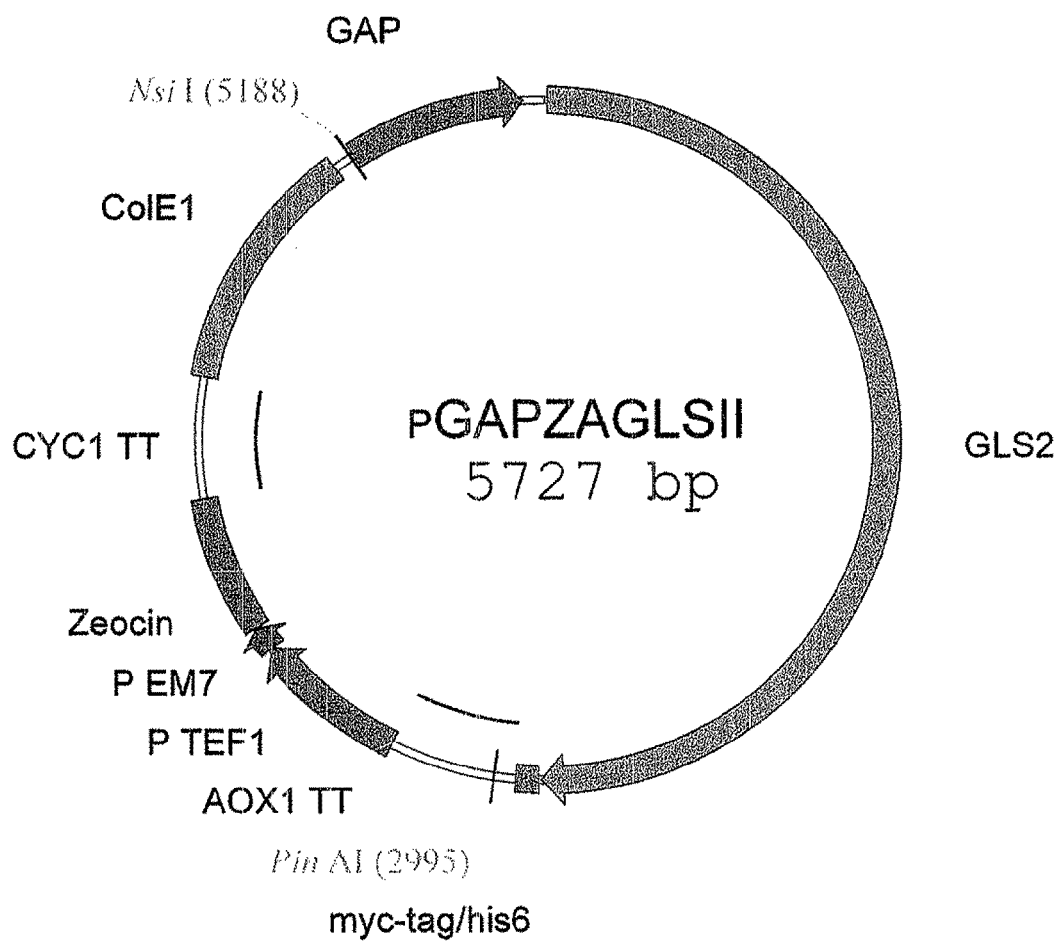
FIG. 12 depicts the expression vector pGAPZAGLSII (SEQ ID NO: 18). P TEF1: promotor of S. cerevisiae transcription elongation factor gene. P Em7: synthetic prokaryotic promotor. Zeocin: zeocine resistance marker gene. CYC1 TT: transcription terminator of S. cerevisiae cytochrome C1 gene. Col E1: bacterial origin of replication. GAP: promotor of the P. pastoris GAP gene. GLS2: S. cerevisiae glucosidase II gene. AOX1 TT: transcription terminator of the P. pastoris AOX1 gene
Figure 13:
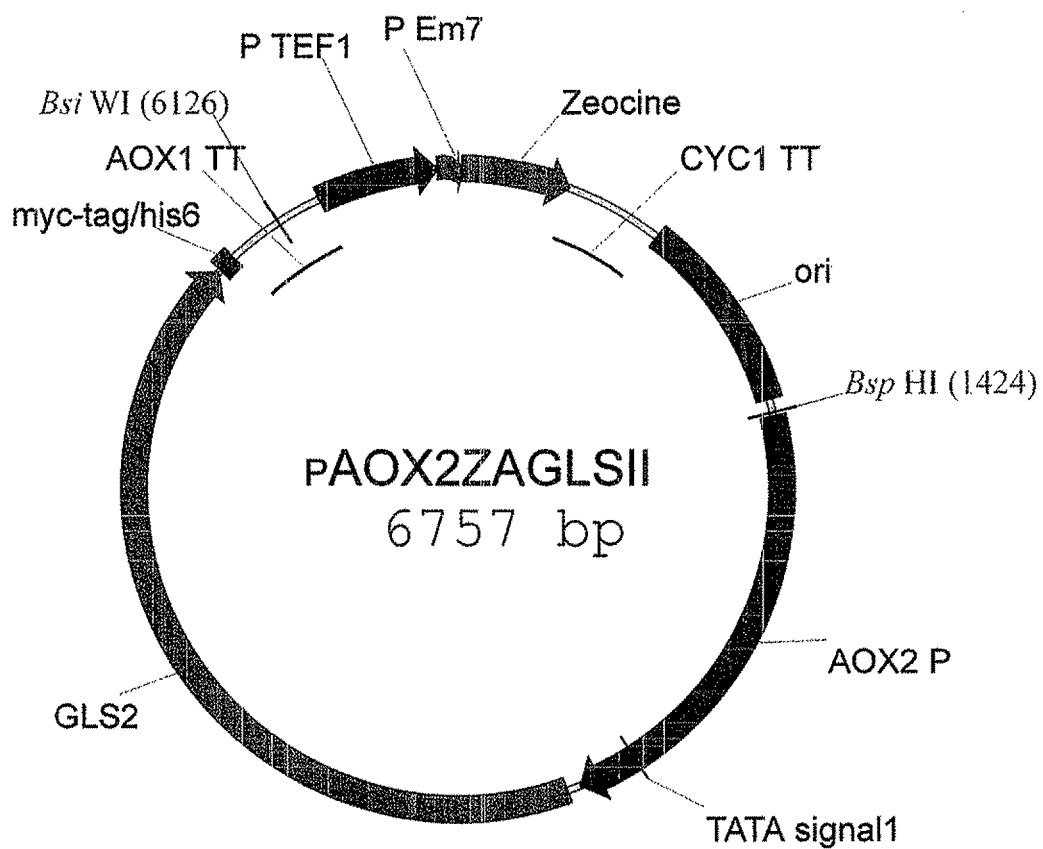
FIG. 13 depicts the expression vector pAOX2ZAGLSII (SEQ ID NO: 16). P TEF1: promotor of S. cerevisiae transcription elongation factor gene. P Em7: synthetic prokaryotic promotor. Zeocin: zeocine resistance marker gene. CYC1 TT: transcription terminator of S. cerevisiae cytochrome C1 gene. Col E1: bacterial origin of replication. AOX2 P: promotor of the P. pastoris AOX2 gene. GLS2: S. cerevisiae glucosidase II gene. AOX1 TT: transcription terminator of the P. pastoris AOX1 gene
Figure 14:
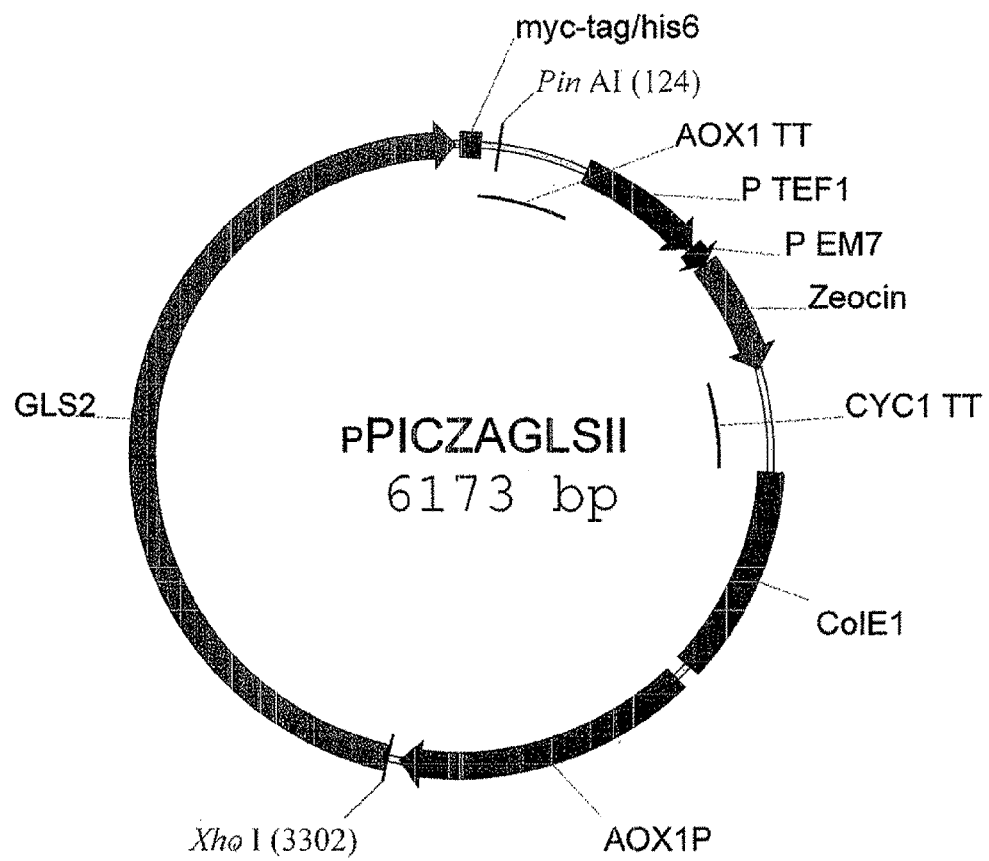
FIG. 14 depicts the expression vector pPICZAGLSII (SEQ ID NO: 20). P TEF1: promotor of S. cerevisiae transcription elongation factor gene. P Em7: synthetic prokaryotic promotor. Zeocin: zeocine resistance marker gene. CYC1 TT: transcription terminator of S. cerevisiae cytochrome C1 gene. Col E1: origin of replication. AOX1 P: promotor of the P. pastoris AOX1 gene. GLS2: S. cerevisiae glucosidase II gene. AOX1 TT: transcription terminator of the P. pastoris AOX1 gene
Figure 15:
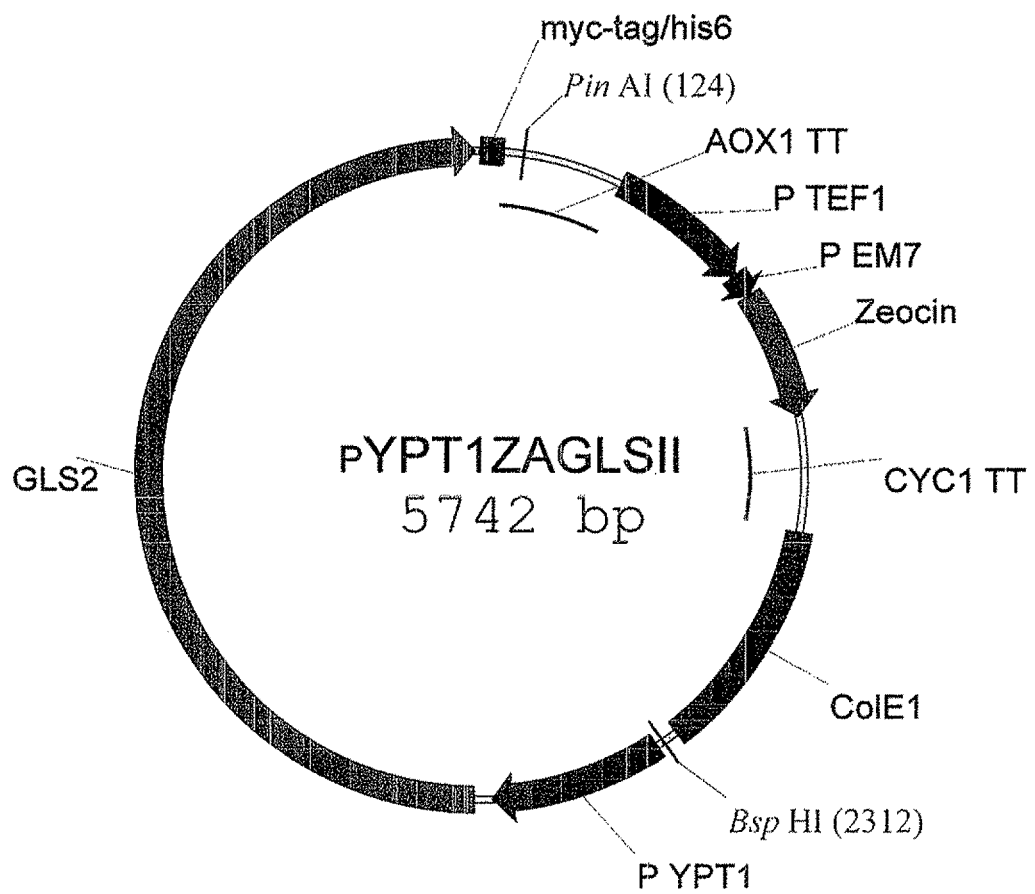
FIG. 15 depicts the expression vector pYPTIZAGLSII (SEQ ID NO: 22). P TEF1: promotor of S. cerevisiae transcription elongation factor gene. P Em7: synthetic prokaryotic promotor. Zeocin: zeocine resistance marker gene. CYC1 TT: transcription terminator of S. cerevisiae cytochrome C1 gene. Col E1: origin of replication. P YPT1: promotor of the P. pastoris YPT1 gene. GLS2: S. cerevisiae glucosidase II gene. AOX1 TT: transcription terminator of the P. pastoris AOX1 gene.
Figure 16:
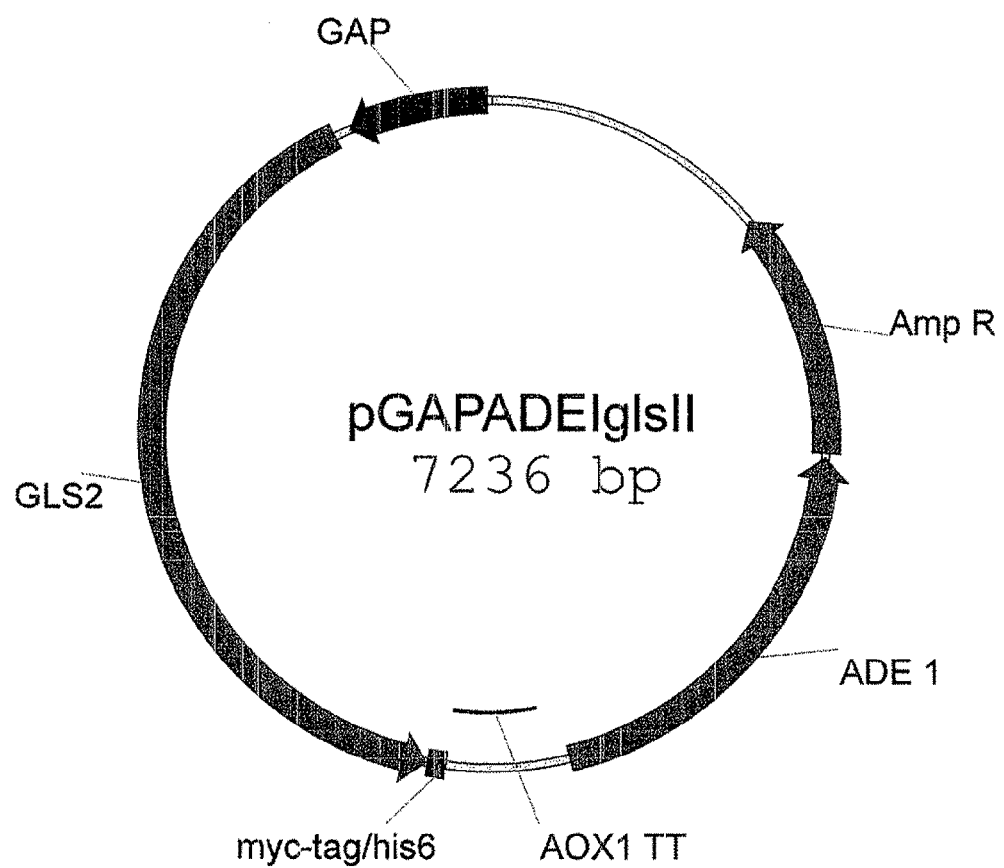
FIG. 16 depicts the expression vector pGAPADE1glsII (SEQ ID NO: 19). Amp R: Ampillicin resistance marker gene. ADE1: P. pastoris ADE1 selection marker gene. GAP: promotor of the P. Pastoris GAP gene. GLS2: S. cerevisiae glucosidase II gene. AOX1 TT: transcription terminator of the P. pastoris AOX1 gene
Figure 17:
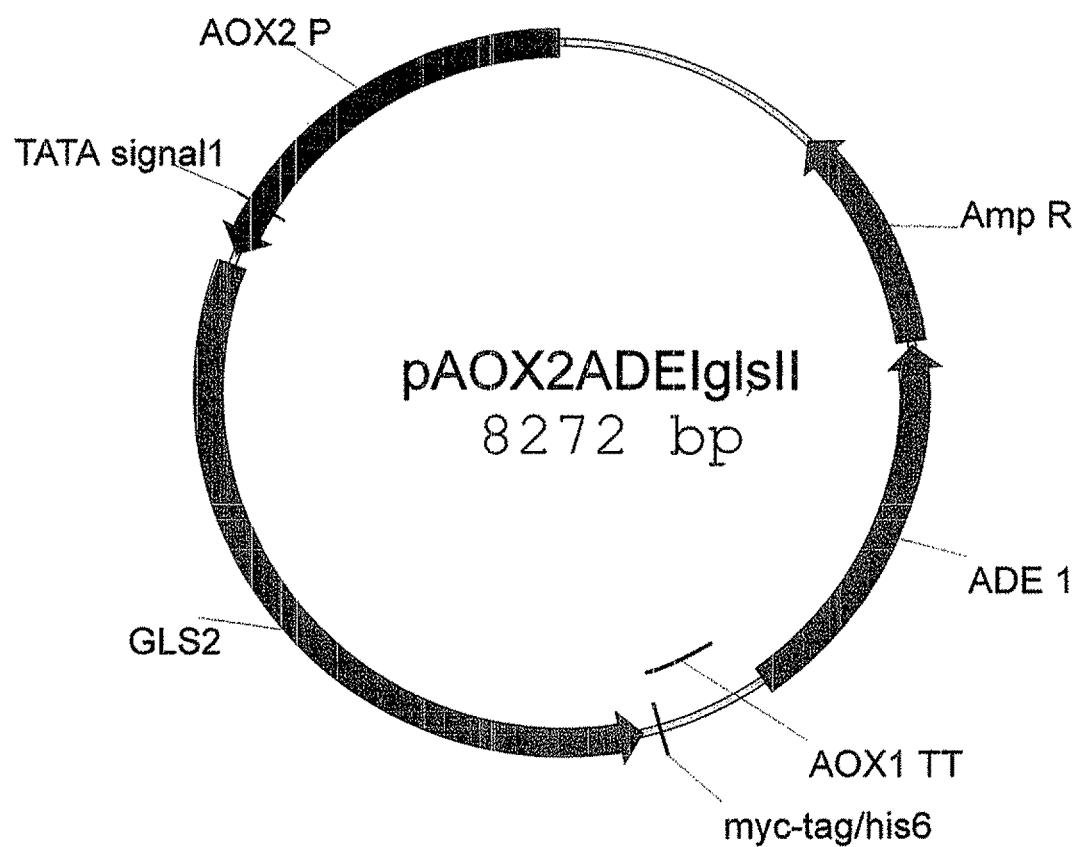
FIG. 17 depicts the expression vector pAOX2ADE1glsII (SEQ ID NO: 17). Amp R: Ampillicin resistance marker gene. ADE1: P. pastoris ADE1 selection marker gene. AOX2 P: promotor of the P. pastoris AOX2 gene. GLS2: S. cerevisiae glucosidase II gene. AOX1 TT: transcription terminator of the P. pastoris AOX1 gene.
Figure 18:
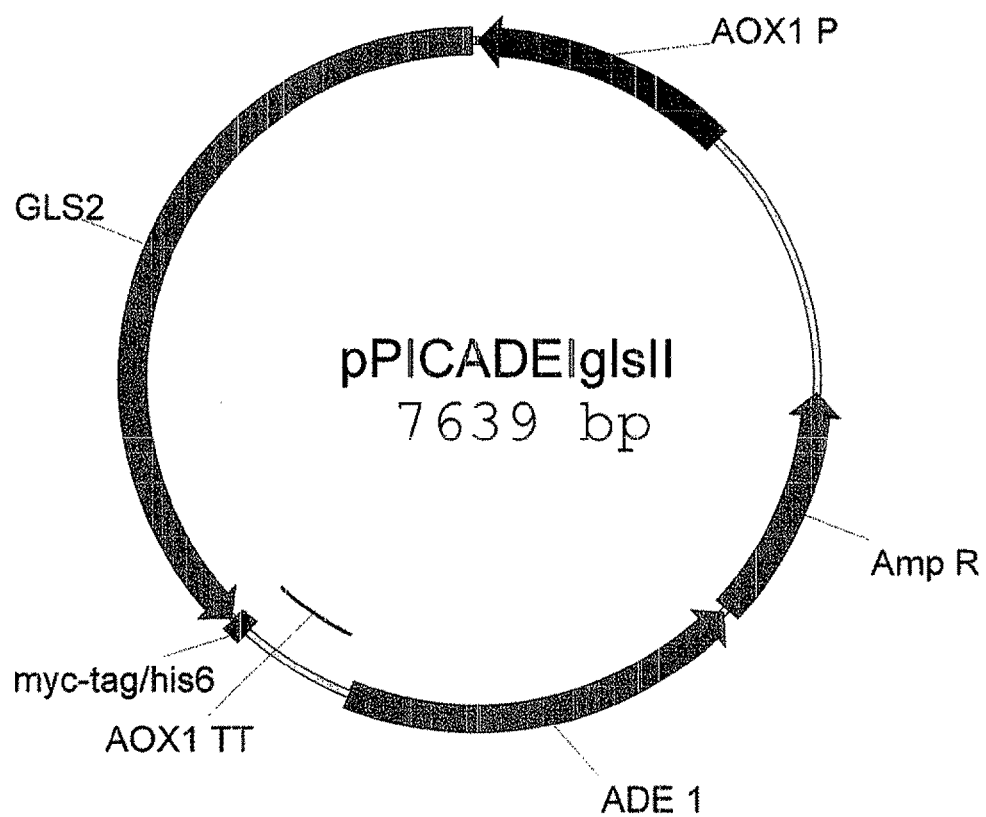
FIG. 18 depicts the expression vector pPICADE1glsII (SEQ ID NO: 21). Amp R: Ampillicin resistance marker gene. ADE1: P. pastoris ADE1 selection marker gene. AOX1 P: promotor of the P. pastoris AOX1 gene. GLS2: S. cerevisiae glucosidase II gene. AOX1 TT: transcription terminator of the P. pastoris AOX1 gene.
Figure 19:
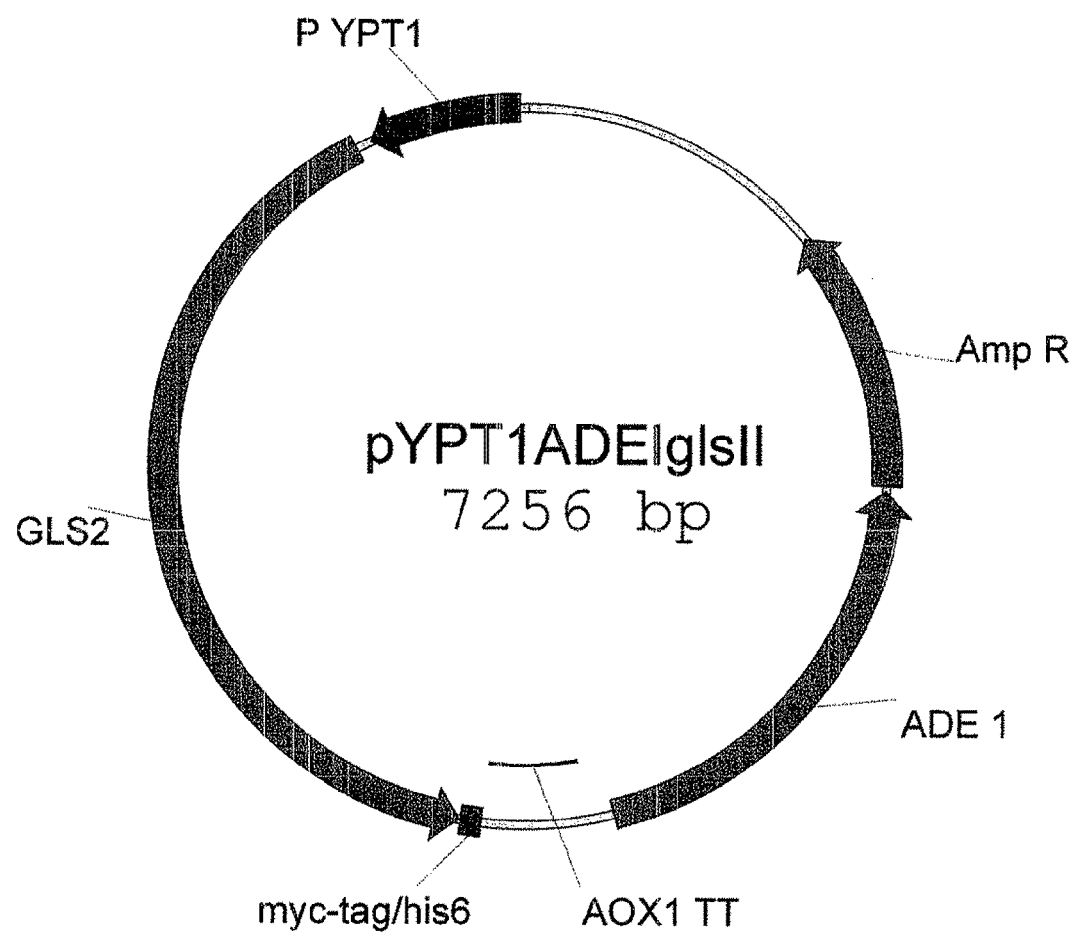
FIG. 19 depicts the expression vector pYPT1ADE1glsII (SEQ ID NO: 23). Amp R: Ampillicin resistance marker gene. ADE1: P. pastoris ADE1 selection marker gene. P YPT1: promotor of the P. pastoris YPT1 gene. GLS2: S. cerevisiae glucosidase II gene. AOX1 TT: transcription terminator of the P. pastoris AOX1 gene.

One of the Och1-inactivated clones was also further transformed with pGAPZMFManHDEL to produce "supertransformants". Both the Och1-inactivated clone and three supertransformants also expressing the ManHDEL were evaluated in cell wall glycan analysis as follows. Yeast cells were grown in 10 ml YPD to an $OD_{600}=2$ and mannoproteins were prepared by autoclaving the yeast cells in 20 mM sodium citrate buffer pH7 for 90 min at 120° C. and recovery of the supernatant after centrifugation. Proteins were precipitated from this supernatant with 3 volumes of cold methanol. The protein preparation obtained in this way was used for N-glycan analysis using DSA-FACE as described by Callewaert et al. (2001) *Glycobiology* 11, 275-281. As shown in FIG. 10, there was an increased amount of $Man_8GlcNAc_2$ glycan in the Och1-inactivated clone as compared to parent strain yGC4, indicative of a reduced activity of the Och1 enzyme. In all three supertransformants which also expressed the HDEL (SEQ ID NO: 1)-tagged α-1,2 mannosidase, the production of $Man_5GlcNAc_2$ was observed. Furthermore, upon digestion of the same glycan mixtures with 3 mU/ml purified recombinant *Trichoderma reesei* α-1,2-mannosidase, more $Man_5GlcNAc_2$ was formed in the strain transformed with pBLURA5'PpOCH1 than in the parent strain (FIG. 11, compare panel 2 and 3).

These results confirmed that the lack of a production of $Man_5$ glycans on recombinantly produced proteins such as haemagglutinin from cells expressing α-1,2-mannosidase were due to the activity of the Och1 protein. These results further indicate that the production of glycoproteins with $Man_5$ glycans could be facilitated by the inactivation of the Och1 gene.

EXAMPLE 4

Expression of Glucosidase II in *Pichia pastoris*

4.1 Amplification of the GLSII Alpha Subunit ORF from *S. cerevisiae*.

Genomic DNA was prepared from the *S. cerevisiae* strain INVS (α, leu2-3, 112 his3Δ1, trpl-289, ura3-52), using the Nucleon kit (Amersham). A touch-down PCR reaction was performed using this genomic DNA as template and the LA TaKaRa polymerase (ImTec Diagnostics). The sequence of the PCR primers was based on the known sequence of the *S. cerevisiae* GLSII ORF:

```
Sense primer:
                                    (SEQ ID NO: 12)
5' CCG CTC GAG ATG GTC CTT TTG AAA TGG CTC 3'
       Xho I Antisense primer:
                                    (SEQ ID NO: 13)
5' CCG GGC CCA AAA ATA ACT TCC CAA TCT TCA G 3'
       Apa I
```

4.2 Cloning of the *S. cerevisiae* Glucosidase II ORF into *Pichia pastoris* Expression Vectors.

Construction of the glucosidase II expression vectors—The PCR fragment was digested with Xho I/Apa I and ligated into the pGAPZA vector (Invitrogen), thereby placing the ORF under the transcriptional control of the GAP promoter. Using this strategy, the myc and the His6 tag were placed in frame to the C-terminus of Glucosidase II, creating pGAPZAGLSII. The complete ORF of pGAPZAGLSII was then sequenced to ensure that no mutations were generated in the PCR reaction. The sequence of the vector pGAPZAGLSII was set forth in SEQ ID NO: 18. The GLSII ORF from the pGAPZAGLSII vector was cloned into vector pPICZA (Invitrogen) to create pPICZAGLSII, thereby placing the ORF under the transcriptional control of the AOXI promoter. The GLSII ORF from the pGAPZAGLSII vector was cloned into vector pAOX2ZA, thereby placing the ORF under the transcriptional control of the AOX2 promoter. This vector was created by replacing the multi cloning site of vector pAOX2ZB with the multi cloning site of pPICZA. Vector pAOX2ZB was generated by replacing the AOX1 promotor of pPICZB by the AOX2 promotor region of the AOX2 gene (Martinet et al., Biotechnology Letters 21). The AOX2 promotor region was generated by PCR on *Pichia* genomic DNA with the sense primer 5'GACGAGATCTTTTTTTCAGAC-CATATGACCGG 3' (SEQ ID NO: 26) and the antisense primer 5'GCGGAATTCTTTTCTCAGTTGATTTGTTTGT 3' (SEQ ID NO: 27). The GLSII ORF from the pGAPZGLSII vector was cloned into vector pYPTIZA to create pYPTIZA-GLSII, thereby placing the ORF under the transcriptional control of the YPT1 promoter. Vector pYPTZA was created by replacing the AOX1 promoter of pPICZA by the YPT1 promoter present on the plasmid pIB3 (GenBank accession number AF027960)(Sears et al., Yeast 14, pg 783-790, 1998). All constructs contain the phleomycin resistance gene. The resulting final expression vectors (pGAPZAGLSII, pAOX2ZAGLSII, pPICZAGLSII and pYPTIZAGLSII) are depicted in FIGS. 12-15.

Similar expression vectors were constructed, carrying the Ampicillin resistance marker and the *Pichia* ADE1 selection marker. In principle, the Zeocin resistance expression cassette of the plasmids pAOX2ZAGLSII, pGAPZAGLSII and pYPTIZAGLSII was replaced by the Ampicillin and *Pichia* ADE1 cassette of the vector pBLADE IX (Cregg, J. M.) to result in the vectors pAOX2ADE1glsII, pGAPADE1glsII and pYPT1ADE1 glsII. Vector pPICADE1glsII was obtained by inserting the glucosidase II open reading frame into the multiple cloning site of the vector pBLADE IX (Cregg, J. M.). The resulting final expression vectors (pGAPADE1glsII, pAOX2ADE1glsII, pPICADE1glsII and pYPTIADE1glsII) are depicted in FIGS. 16-20.

Adding the ER retention tag HDEL to Glucosidase II expression vectors—The following primers were used to generate an HDEL-containing PCR fragment:

```
Primer 1:
                                    (SEQ ID NO: 28)
5'GCG GGT CGA C/CA C/GA C/GA A/CT G/TG A/GT TTT
        Sal I    H    D    E    L    stop
AGC CTT AGA CAT GAC 3'

Primer 2:
                                    (SEQ ID NO: 29)
5'CAG GAG CAAA GCT CGT ACG AG 3'
                        Spl I
```

Figure 20:
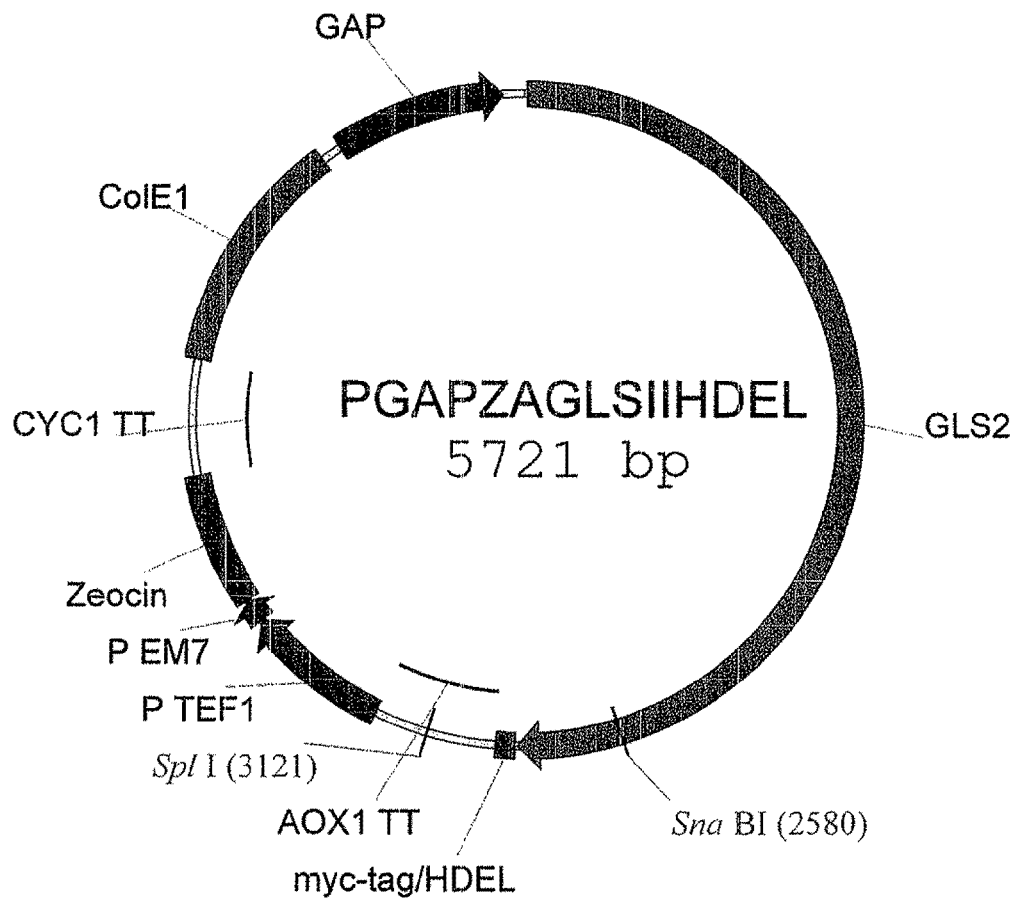
FIG. 20 depicts the expression vector pGAPZAglsIIHDEL (SEQ ID NO: 24). Amp R: Ampillicin resistance marker gene. ADE1: P. pastoris ADE1 selection marker gene. GAP: promotor of the P. pastoris GAP gene. GLS2: S. cerevisiae glucosidase II gene. AOX1 TT: transcription terminator of the P. pastoris AOX1 gene.
Figure 21:
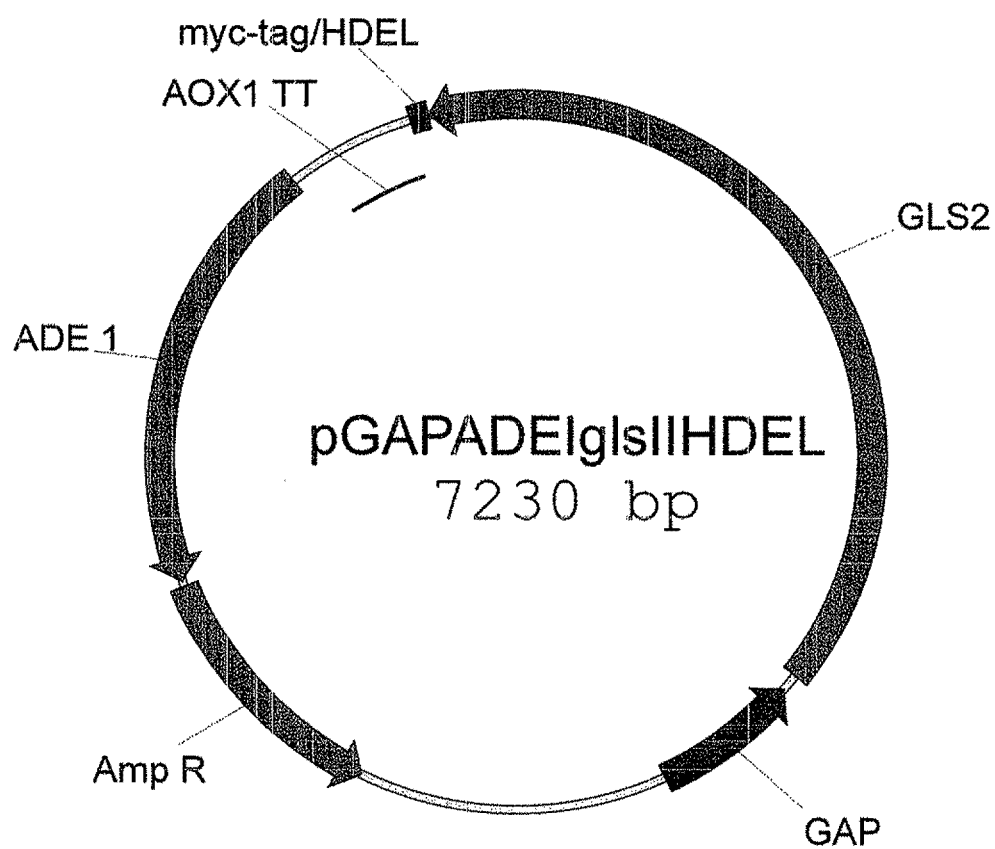
FIG. 21 depicts the expression vector pGAPADEIglsIIH-DEL (SEQ ID NO: 25). P TEF1: promotor of S. cerevisiae transcription elongation factor gene. P Em7: synthetic prokaryotic promotor. Zeocin: zeocine resistance marker gene. CYC1 TT: transcription terminator of S. cerevisiae cytochrome C1 gene. Col E1: bacterial origin of replication. GAP: promotor of the P. pastoris GAP gene. GLS2: S. cerevisiae glucosidase II gene. AOX1 TT: transcription terminator of the P. pastoris AOX1 gene.

PCR was performed on pGAPZAGLSII with Taq pol., at 60° C. The PCR fragment of 225 bp was cut with Sal I/Spl I and ligated into the Sal I/Spl I opened pGAPZAGLSII vector, creating plasmid pGAPZAglsIIHDEL. The sequence of plasmid pGAPZAglsIIHDEL is set forth in SEQ ID NO: 24. The construction strategy and the resulting final expression vectors (pGAPZAglsIIHDEL and pGAPADE1glsIIHDEL) are depicted in FIGS. 20-21.

4.3 Transformation of a *Pichia pastoris* Strain.

Transformation was performed using the conventional electroporation techniques, as described by Invitrogen. Cells of the *Pichia pastoris* strain PPY12-OH were transformed with pGAPZGLSII which had been cut with the single cutter Avr II. Transformants were selected based on their resistance to zeocin.

Genomic Analysis of the Transformants—

Genomic DNA was prepared from some zeocin resistant *Pichia* transformants. A PCR reaction was performed on the genomic DNA in order to determine whether or not the glucosidase II gene was integrated into the yeast genome. PCR was performed using Tag DNA polymerase (Boehinger) (2.5 mM $MgCl_2$, 55° C. for annealing). The primers were the same as the ones we used for the amplification of the ORF on *S. cerevisiae* genomic DNA. pGAPZAGLSII transformants were confirmed by the presence of a specific PCR product indicative of the glucosidase II ORF.

4.4 Expression and Secretion of the *S. cerevisiae* Glucosidase II Alpha Subunit in *Pichia Pastoris*

Analysis at the Transcriptional Level—

RNA was prepared from the transformants which scored positive after the genomic analysis. RNA was prepared using acid phenol. From each sample, 15 μg of RNA was loaded on a formaldehyde agarose gel. After electrophoresis the RNA was blotted on a Hybond N membrane. The membrane was hybridizing using a radioactive probe, which consists of a 344 bp glucosidase II specific fragment, corresponding to the 3' region of the glucosidase II ORF. No signals were detected with non-transformed control strains, whereas clear signals were observed with transformants.

Analysis at the Protein Level Using a Double Membrane Assay—

A nitrocellulose membrane was placed on a buffered dextrose medium (BMDY). On top of that nitrocellulose membrane, a cellulose acetate membrane was placed. *Pichia* transformants of pGAPZAGLSII were streaked on the cellulose acetate and grown for a few days. The yeast cells remained on the cellulose acetate, while the secreted proteins crossed this membrane. As such the secreted protein was captured onto the nitrocellulose membrane. After a few days the cellulose acetate, containing the yeast colonies, was removed. The nitrocellulose membrane was analyzed for the presence of glucosidase II using anti-myc antibody. Most of the transformants gave a clear signal as compared to a faint, hardly visible signal with the WT, non-transformed strain.

Extracellular Expression—

PPY12-OH transformants of the construct pGAPZAGLSII (mychis6) (strains 12, 14 and 18) and transformants of the construct pGAPZAGLSII(myc)HDEL (strains H1, H2 and H3) were grown for 2 days on 2×10 ml BMDY medium. These 6 transformants earlier scored positive both on the genomic level (PCR on gDNA) and on the RNA level (Northern blot). The culture medium was collected by centrifugation and concentrated with Vivaspin columns to about 1 ml. Proteins from this concentrate were precipitated with TCA, resuspended in Laemmli buffer and loaded for SDS-PAGE analysis. Proteins were blotted to nitrocellulose membrane. The blot was incubated overnight with anti-myc Ab. The secondary Ab was linked to peroxidase. Using the Renaissance luminiscence detection kit (NEN) and a light sensitive film (Kodak), a strong band at about 110 kDa was observed for the transformants 12, 14 and 18, indicating that GLSII was expressed and secreted from these transformants. No signal was obtained for the transformants H1-3, which indicate that the HDEL (SEQ ID NO: 1) tag, which was added C-terminally to the GLSII ORF, resulted in an ER localization of the protein, preventing GLSII to be secreted into the growth medium.

Intracellular Expression—

The 6 transformants and the WT strain were grown for 2 days in 500 ml BMDY. The cells were collected by centrifugation, washed, resuspended into a minimal volume (50 mM Tris.HCl pH 7.5, 5% glycerol) and broken using glass beads. The cell debris was removed through several centrifugation steps (low speed centrifugation (2000-3000 g)). Membranes were obtained from the supernatant through ultracentrifugation. The pellets were resuspended in Laemmli buffer and loaded for SDS-PAGE analysis. The proteins were blotted on a nitrocellulose membrane. The intracellular GLSII expression was checked using anti-myc Ab and peroxidase conjugated secondary Ab. Following the luminescence detection, a band at about 110 kDA was observed with the GLSIIHDEL tranformants (H1 and H3, faint signal for H2), but not with the WT and GLSII expression strains. These results clearly indicate the intracellular presence of the recombinant GLSII when expressed with a C-terminal HDEL (SEQ ID NO: 1) tag. No GLSII was detected intracellularly when this tag was not present.

4.5 Purification and Activity Assays of the Recombinant Glucosidase II Alpha Submit A GLSII assay was set up as follows and was tested using a commercially available yeast alpha-glucosidase (Sigma) as a positive control.

Figure 22:
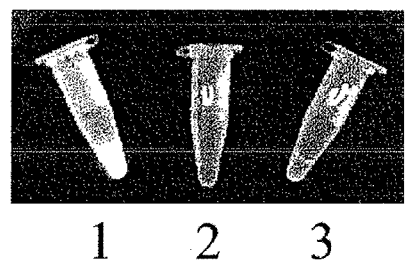
FIG. 22 depicts the test of the GLSII activity assay using a commercially available yeast alpha-glucosidase (Sigma: Cat. No. G-5003). The assay mixture contains phosphate-citrate buffer pH 6.8, mannose, 2-deoxy-D-glucose, the substrate 4-methylumbellyferyl-alpha-D-glucopyranoside and alpha-glucosidase from Sigma. 1: assay mixture illuminated with UV-light after overnight incubation at 37° C.; 2: same as 1, but this time, the assay mixture lacks the alpha-glucosidase; 3: same as 1, but this time, the assay mixture lacks the substrate.

Composition: 70 μl 80 mM phosphate-citrate buffer pH 6.8, 7 μl 250 mM mannose, 3.5 μl 250 mM 2-deoxy-D-glucose, 0.8 μl 4-MeUmbelliferyl-alpha-D-glucopyranoside (1 μM). Three assays were performed: one with 1 unit commercial enzyme, one without the enzyme and one with the enzyme but without the substrate. The assay mixture was incubated overnight at 30° C. When illuminated with UV, only the reaction mixture with both the enzyme and the substrate showed fluorescence (FIG. 22). This indicates that the assay was very specific in detecting the activity of the alpha-glucosidase.

Figure 23:
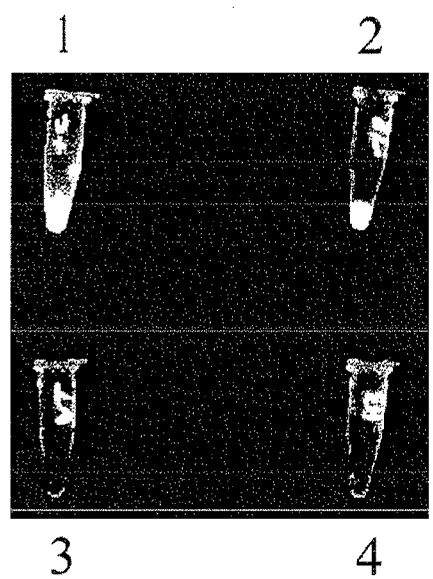
FIG. 23 depicts the results of the activity of recombinantly expressed GLSII from Pichia pastoris. All assay mixtures were incubated overnight at 37° C. and afterwards illuminated with UV-light. 1: assay with yeast alpha-glucosidase (Sigma: Cat. No. G-5003); 2: assay with the purified medium of strain 18 (PPY12-OH transformed with pGAPZAGLSII); 3: assay with purified medium of the WT PPY12-OH strain; 4: assay with the purified medium of strain H3 (PPY12-OH transformed with pGAPZAglsIIHDEL).

WT PPY12-OH, strain 18 and strain H3 were grown during 2 days in 2×10 ml growth medium. Cells were spun down and medium was adjusted to 300 mM NaCl and 10 mM imidazol and concentrated with Vivaspin columns to 0.5-1 ml. Medium was loaded onto a Ni-NTA spin column (Qiagen) and the purification was performed according to the manufactures recommendations. Protein was eluted from the column in 2×100 μl elution buffer (50 mM NaH$_2$PO$_4$, 300 mM NaCl, 250 mM imidazol pH 8.0). From each eluate, 20 μl was assayed for its glucosidase II activity. 0.33 units of the commercial enzyme diluted in 20 μl of the elution buffer was used as a positive control. Fluorescence was observed with the positive control and the elute of strain 18, the strain which secreted the enzyme into the growth medium. These results indicate that the recombinant *S. cerevisiae* GLSII alpha subunit, secreted by *Pichia pastoris*, was a functionally active enzyme. The activity was not seen in the WT (untransformed) strain, nor in strain H3 as the GLSII was expressed intracellularly (FIG. 23). These results also indicate that the beta subunit is not necessary for the functionality of the alpha part of the protein.

EXAMPLE 5

Creating *Pichia* Strains Expressing Both Glucosidase II and Mannosidase

Strain GS115 was transformed with pGAPZGLSII and pGAPZglsIIHDEL. Transformants were selected on YPD-Szeo.

Strain yGC4 was transformed with the following constructs, respectively:

(1) pGAPADEglsII and pGAPADEglsIIHDEL, selection on synthetic sorbitol medium without adenine;

(2) pGAPZMFManHDEL: selection on YPDSzeo; and (3) pGAPZMFManHDEL/pGAPADEglsIIHDEL: selection on synthetic sorbitol medium without adenine and with zeocin.

Strain yGC4 with OCH1 knock-in and expressing MFmannosidaseHDEL was transformed with pGAPADEglsII and pGAPADEglsIIHDEL. Selection of transformants was done on synthetic sorbitol medium without adenine and uracil.

For all transformations, colonies were obtained. Transformants with the expression vector(s) integrated into the genome, determined by PCR, were obtained. Expression of GLSII from some of these transformants was observed.

We claim:

1. A genetically engineered *Pichia pastoris* strain, which lacks a functional enzyme involved in production of high mannose structures, and expresses at least one exogenous enzyme for production of the N-glycan, $Man_5GlcNAc_2$, wherein said enzyme involved in production of high mannose structures is α-1,6-mannosyltransferase encoded by the OCH1 gene, wherein said at least one enzyme for production of $Man_5GlcNAc_2$ is α-1,2-mannosidase or an enzymatically active fragment thereof which is expressed from an expression vector transformed into said strain, and said α-1,2-mannosidase or said enzymatically active fragment thereof is targeted to the endoplasmic reticulum (ER), and wherein said OCH1 gene is disrupted in said strain and the OCH1 gene disruption is the sole genetic disruption of genes coding for Golgi mannosyl transferases acting in N-glycosylation of said strain, and wherein the strain produces $Man_5GlcNAc_2$ as a result of expression of said α-1,2-mannosidase or said enzymatically active fragment and the OCH1 gene disruption.

2. The strain of claim 1, wherein said α-1,2-mannosidase is of a fungal origin or a mammalian origin.

3. The strain of claim 1, wherein the targeting of said-α-1,2-mannosidase to the ER is achieved by engineering said α-1,2-mannosidase to include the ER retention signal as set forth in SEQ ID NO: 1.

4. The strain of claim 1, wherein said α-1,2-mannosidase is *T. reesei* α-1,2-mannosidase, and said strain produces $Man_5GlcNAc_2$ as a predominant N-glycan structure or a predominant intermediate N-glycan structure.

5. A method for producing a glycoprotein with reduced hyperglycosylation in *Pichia pastoris*, comprising providing a strain according to claim 1; and producing said glycoprotein in said strain.

6. The method of claim 5, wherein said α-1,2-mannosidase is of a fungal origin or a mammalian origin.

7. The method of claim 5, wherein the targeting of said α-1,2-mannosidase to the ER is achieved by engineering said α-1,2-mannosidase to include the ER retention signal as set forth in SEQ ID NO: 1.

8. The method of claim 5, wherein said α-1,2-mannosidase is *T. reesei* α-1,2-mannosidase, and said strain produces $Man_5GlcNAc_2$ as a predominant N-glycan structure or a predominant intermediate N-glycan structure.

9. The strain of claim 1, wherein the expression vector has been integrated into the genome of said strain.

10. The strain of claim 1, wherein the expression vector is a replicative vector.

11. The method of claim 5, wherein the expression vector has been integrated into the genome of said strain.

12. The method of claim 5, wherein the expression vector is a replicative vector.

* * * * *